US012193684B2

(12) United States Patent
Viola et al.

(10) Patent No.: US 12,193,684 B2
(45) Date of Patent: Jan. 14, 2025

(54) CUTTING GUIDE SYSTEMS AND METHODS

(71) Applicant: Chain Orthopedics, LLC, Bogota, NJ (US)

(72) Inventors: Paul Viola, Bogota, NJ (US); Richard Thomas Briganti, Bala Cynwyd, PA (US); Timothy J. Langloss, Berwyn, PA (US)

(73) Assignee: Chain Orthopedics, LLC, Bogota, NJ (US)

( * ) Notice: Subject to any disclaimer, the term of this patent is extended or adjusted under 35 U.S.C. 154(b) by 0 days.

(21) Appl. No.: 17/590,192

(22) Filed: Feb. 1, 2022

(65) Prior Publication Data
US 2022/0273315 A1    Sep. 1, 2022

Related U.S. Application Data

(60) Provisional application No. 63/195,994, filed on Jun. 2, 2021, provisional application No. 63/154,367, filed on Feb. 26, 2021.

(51) Int. Cl.
*A61B 17/15* (2006.01)
*A61B 17/00* (2006.01)

(52) U.S. Cl.
CPC .. *A61B 17/154* (2013.01); *A61B 2017/00075* (2013.01); *A61B 2017/00477* (2013.01)

(58) Field of Classification Search
CPC .................................................. A61B 17/154
See application file for complete search history.

(56) References Cited

U.S. PATENT DOCUMENTS 614,003 A    11/1898    Johnson
1,178,362 A    4/1916    Wall
(Continued)

FOREIGN PATENT DOCUMENTS

CN    1827275 A    9/2006
DE    2611720 A1    9/1977
(Continued)

OTHER PUBLICATIONS

Alessi, A., et al., "The Functionality of a Novel Robotic Surgical Assistant for Total Knee Arthroplasty: A Case Series," Case Reports in Orthopedics, vol. 2021, Article ID 6659707, 18 pages (Mar. 17, 2021).
(Continued)

*Primary Examiner* — Sameh R Boles
(74) *Attorney, Agent, or Firm* — Potomac Law Group, PLLC; Douglas E. Ringel

(57) ABSTRACT

Cutting guide systems for adjusting and stabilizing cutting devices are disclosed. Example cutting guide systems may be used in orthopedic surgery. In some examples, a cutting guide system comprises a support mount, a joint, and a cutting instrument support, wherein the joint permits the cutting instrument support to be adjusted with respect to the support mount. The joint may permit the cutting instrument support to be rotated about at least two axes. The joint may be lockable to hold the position of the cutting instrument support. A cutting instrument may be pivotable and/or movable in a longitudinal direction with respect to the cutting instrument support. In some examples, a cutting guide system comprises a track, wherein a cutting instrument support is connected to the track in a manner that permits the cutting instrument support to move along a path. Methods of using cutting guide systems are also disclosed.

35 Claims, 46 Drawing Sheets

(56) References Cited

U.S. PATENT DOCUMENTS

| | | | |
|---|---|---|---|
| 2,007,806 A | 7/1935 | Logan | |
| 2,117,586 A | 5/1938 | Willson | |
| 2,308,847 A | 1/1943 | Wolf | |
| 2,380,753 A | 7/1945 | Hard af Segerstad | |
| 2,427,580 A | 9/1947 | Stryker | |
| 2,638,944 A | 5/1953 | Woleslagle | |
| 2,649,871 A | 8/1953 | Desbaret | |
| 3,910,147 A | 10/1975 | Heyerdahl | |
| 4,316,327 A | 2/1982 | Scott et al. | |
| 4,457,307 A * | 7/1984 | Stillwell | A61B 17/154 606/88 |
| 4,492,140 A | 1/1985 | Pano | |
| 4,562,761 A | 1/1986 | Alexander | |
| 4,683,659 A | 8/1987 | Wunsch et al. | |
| 4,807,366 A | 2/1989 | Masato et al. | |
| 5,209,216 A | 5/1993 | Mogi | |
| 5,226,404 A | 7/1993 | Mogi et al. | |
| 5,345,686 A | 9/1994 | Zimmermann | |
| 5,725,530 A | 3/1998 | Popken | |
| 5,826,343 A | 10/1998 | Mollberg, Jr. | |
| 6,178,960 B1 | 1/2001 | Svensson | |
| 6,564,459 B1 | 5/2003 | Steinbrueck et al. | |
| 6,694,623 B1 | 2/2004 | Haughey | |
| 6,782,627 B2 | 8/2004 | Hermes et al. | |
| 7,155,832 B2 | 1/2007 | Warfel et al. | |
| 7,743,513 B1 | 6/2010 | Fisher et al. | |
| 8,398,640 B2 | 3/2013 | Hawkins et al. | |
| 8,498,744 B2 | 7/2013 | Odermatt et al. | |
| 9,339,878 B2 | 5/2016 | Fuchs | |
| 9,367,062 B2 | 6/2016 | Volpert | |
| 9,457,489 B2 | 10/2016 | Fuchs | |
| 9,539,717 B2 | 1/2017 | Fuchs | |
| 9,579,783 B2 | 2/2017 | Wirnitzer et al. | |
| 9,610,698 B2 | 4/2017 | Fuchs | |
| 9,616,512 B1 | 4/2017 | Viola | |
| 9,701,037 B2 | 7/2017 | Zieger et al. | |
| 9,707,677 B2 | 7/2017 | Zieger et al. | |
| 9,724,841 B2 | 8/2017 | Engelfried et al. | |
| 9,744,606 B2 | 8/2017 | Engelfried et al. | |
| 9,744,684 B2 | 8/2017 | Fuchs | |
| 9,744,686 B2 | 8/2017 | Engelfried et al. | |
| 9,789,625 B2 | 10/2017 | Engelfried et al. | |
| 9,789,627 B2 | 10/2017 | Engelfried et al. | |
| 9,844,824 B2 | 12/2017 | Fuchs | |
| 9,937,573 B2 | 4/2018 | Haldar | |
| 9,962,854 B2 | 5/2018 | Hug et al. | |
| 10,052,785 B2 | 8/2018 | Fuchs et al. | |
| 10,160,135 B2 | 12/2018 | Bozic | |
| 10,173,339 B2 | 1/2019 | Fuchs et al. | |
| 10,350,782 B2 | 7/2019 | Engelfried et al. | |
| 10,384,367 B2 | 8/2019 | Engelfried et al. | |
| 10,391,568 B2 | 8/2019 | Fuchs | |
| 10,406,714 B2 | 9/2019 | Duerr et al. | |
| 10,486,326 B2 | 11/2019 | Fuchs | |
| 10,500,656 B2 | 12/2019 | Lutz et al. | |
| 10,639,731 B2 | 5/2020 | Engelfried et al. | |
| 10,695,939 B2 | 6/2020 | Fuchs et al. | |
| 11,192,271 B2 | 12/2021 | Roden et al. | |
| 2003/0045883 A1 | 3/2003 | Chow et al. | |
| 2005/0028375 A1 | 2/2005 | Stones et al. | |
| 2006/0009796 A1 * | 1/2006 | Carusillo | B27B 19/006 606/178 |
| 2006/0122616 A1 | 6/2006 | Bennett et al. | |
| 2006/0200161 A1 | 9/2006 | Plaskos et al. | |
| 2006/0229649 A1 | 10/2006 | Levesque et al. | |
| 2007/0123896 A1 * | 5/2007 | Wyss | A61B 17/15 606/87 |
| 2008/0033443 A1 * | 2/2008 | Sikora | A61B 17/157 606/87 |
| 2008/0140081 A1 * | 6/2008 | Heavener | A61B 17/155 606/87 |
| 2011/0005088 A1 | 1/2011 | Pellenc | |
| 2011/0314682 A1 | 12/2011 | Maag et al. | |
| 2012/0279074 A1 | 11/2012 | Ruth | |
| 2013/0228058 A1 | 9/2013 | Gruber et al. | |
| 2014/0059868 A1 | 3/2014 | Engelfried et al. | |
| 2014/0060279 A1 | 3/2014 | Fuchs | |
| 2014/0083884 A1 | 3/2014 | Everett | |
| 2014/0106915 A1 | 4/2014 | Kistler et al. | |
| 2014/0123504 A1 | 5/2014 | Fuchs | |
| 2014/0123827 A1 | 5/2014 | Fuchs et al. | |
| 2014/0193039 A1 | 7/2014 | Wexler | |
| 2015/0122102 A1 | 5/2015 | Engelfried et al. | |
| 2016/0052158 A1 | 2/2016 | Luedtke | |
| 2017/0320227 A1 | 11/2017 | Engelfried et al. | |
| 2018/0162007 A1 | 6/2018 | Engelfried et al. | |
| 2018/0339387 A1 | 11/2018 | Kahle et al. | |
| 2019/0223393 A1 | 7/2019 | Blevens et al. | |
| 2019/0388158 A1 * | 12/2019 | Mahfouz | A61B 17/1764 |
| 2020/0001493 A1 | 1/2020 | Engelfried et al. | |
| 2020/0038978 A1 | 2/2020 | Fuchs | |
| 2021/0235626 A1 | 8/2021 | Gerstenberger et al. | |
| 2021/0334995 A1 | 10/2021 | Spence et al. | |
| 2022/0032489 A1 | 2/2022 | Viola et al. | |

FOREIGN PATENT DOCUMENTS

| | | |
|---|---|---|
| EP | 2990170 A1 | 3/2016 |
| EP | 2866987 B1 | 4/2020 |
| EP | 2866988 B1 | 5/2020 |
| ES | 1154011 U | 4/2016 |
| GB | 2354481 A | 3/2001 |
| KR | 2020200002598 U | 12/2020 |
| WO | 2014001066 A1 | 1/2014 |
| WO | 2022026535 A1 | 2/2022 |

OTHER PUBLICATIONS

Bosch Media Service, "Quick, easy and powerful sawing in house and garden: New 'NanoBlade' saw from Bosch for DIY enthusiasts," Robert Bosch GmbH (https://www.bosch-presse.de/pressportal/de/en/18-volt-akku-saege-erweitert-das-programm-148813.html), 7 pages (2018).

Bosch Stories, "Small chain, big impact; NanoBlade: a technology which revolutionizes sawing," Robert Bosch GmbH (https://www.bosch.com/stories/nanoblade-small-chain-big-impact/), 10 pages (undated).

BuildingPoint Central, "Why Use 3D Laser Scanning in Home Building and Renovations," https://buildingpointcentral.com/why-use-3d-laser-scanning-in-home-building-and-renovations/, 11 pages (Sep. 13, 2021).

Cobot Nation, "Cobot Nation Partners with Cognex to Utilize Machine Vision with Collaborative Robots," 3 pages (Aug. 18, 2021).

Halanski, M.A., "How to Avoid Cast Saw Complications," Journal of Pediatric Orthopaedics, 36:S1-S5 (2016).

Intellijoint Surgical, "Intellijoint Surgical Launches New Smart Navigation Solution for Total Knee Replacements—Intellijoint Knee," 5 pages (Mar. 3, 2020).

International Search Report and Written Opinion for International Application No. PCT/US2021/043433 dated Dec. 13, 2021.

International Search Report and Written Opinion for International Application No. PCT/US2022/014679, dated Jul. 1, 2022.

International Search Report and Written Opinion for International Application No. PCT/US2022/028792, Dated Aug. 12, 2022.

MAKO TKA Surgical Guide, PN 210469 Rev 00, 64 pages (2016).

Newmarker, C., "CORI Handheld Robotics System Launches with Smith+Nephew Real Intelligence Line," https://www.therobotreport.com/cori-handheld-robotics-system-launched-smithandnephew/, 5 pages (Jul. 14, 2020).

Parratte, S., et al., "Accuracy of a New Robotically Assisted Technique for Total Knee Arthroplasty: A Cadaveric Study," J Arthroplasty, 34 (11), pp. 2799-2803 (2019).

Schwarzkopf, R., "The use of imageless navigation to quantify cutting error in total knee arthroplasty," Knee Surgery & Related Research 33:43, 9 pages (2021).

Stryker Surgical, "The Stryker Precision Oscillating Tip Saw," product brochure, 2 pages (2006).

(56) References Cited

OTHER PUBLICATIONS

Weytoll, "Weytoll 4 Inch Electric Drill Modified to Electric Chainsaw Tool Attachment Electric Chainsaws Accessory Practical Modification Tool Set Woodworking Cutting Tool," listing from amazon.com, 14 pages (available from May 30, 2022).

Zimmer Biomet, "ROSA Knee System Surgical Technique V 1.1," 60 pages (2020).

* cited by examiner

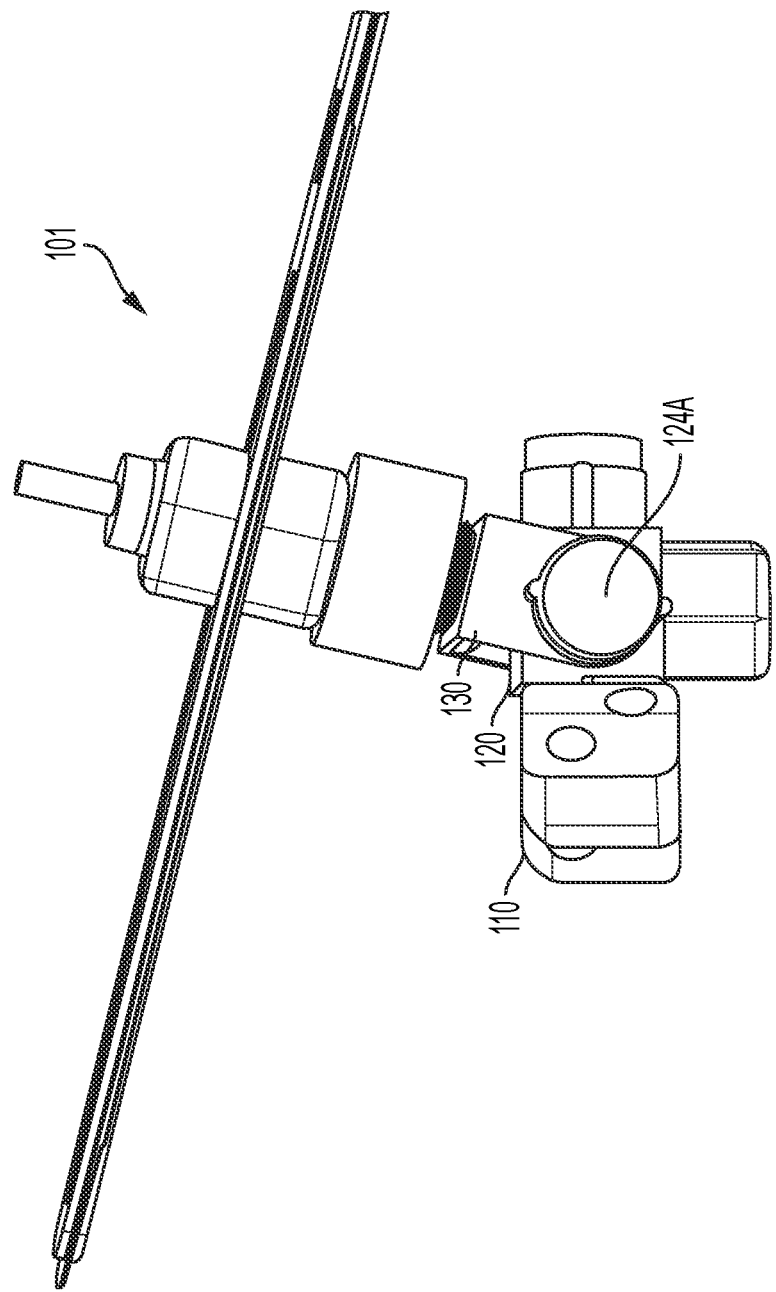

CUTTING GUIDE SYSTEMS AND METHODS

CROSS-REFERENCE TO RELATED APPLICATIONS

This application claims priority to U.S. Provisional Patent Application No. 63/154,367, filed Feb. 26, 2021, entitled "Cutting Guide Systems," and U.S. Provisional Patent Application No. 63/195,994, filed Jun. 2, 2021, entitled "Cutting Guide Systems and Methods." The entire contents of these applications are incorporated herein by reference.

This application is also related to U.S. Provisional Patent Application No. 63/058,216, filed Jul. 29, 2020, entitled "Thin Single Width Chain Saw," U.S. Provisional Patent Application No. 63/085,290, filed Sep. 30, 2020, entitled "Thin Single Width Chain Saw," U.S. Provisional Patent Application No. 63/147,033, filed Feb. 8, 2021, entitled "Chain Saws and Components for Chain Saws," U.S. Provisional Patent Application No. 63/154,379, filed Feb. 26, 2021, entitled "Systems and Methods for Manufacturing Saws and Saw Components," U.S. Provisional Patent Application No. 63/209,525, filed Jun. 11, 2021, entitled "Devices for Maintaining Tension in Chain Saws," U.S. Provisional Patent Application No. 63/209,540, filed Jun. 11, 2021, entitled "Systems for Robotic Surgery," U.S. Non-Provisional patent application Ser. No. 17/443,646, filed Jul. 27, 2021, entitled "Chain Saws, Components for Chain Saws, and Systems for Operating Saws," and International Application No. PCT/US2021/043433, filed Jul. 28, 2021, entitled "Chain Saws, Components for Chain Saws, and Systems for Operating Saws." The entire contents of these applications are incorporated herein by reference.

TECHNICAL FIELD

The present disclosure is directed to cutting guide systems, methods of making and assembling cutting guide systems, and methods of using cutting guide systems.

BACKGROUND

Many people suffer from orthopedic conditions in which the cutting of bone or other tissue is required or useful. As an example, many people suffer from serious joint problems that require surgical procedures to implant artificial joints. Every year physicians implant millions of artificial joints in procedures that require the patient's bone to be modified to accept the implant. The most common joint procedure is knee replacement. The modification of bone in knee replacements involves making a series of flat cuts at the ends of the two main adjacent long bones that will be joined by the implant. Ideally these cuts are made precisely complementary to the shape of the implant. A flat surface of healthy bone opposed to the analogous surface of the implant results in the strongest healing of the connection, with less chance of complications or implant failure.

Sawing bone or other tissue during surgical procedures has requirements beyond those in other sawing applications. Specifically, in surgical procedures, the saw must be sterile, the saw bar needs to be easy to control by the surgeon, and vibration and loud sounds need to be minimized. In addition, the saw must perform the cutting in a way that does not generate excessive heat, the procedure must not deposit metal particles or other contaminants in the surgical field, and the procedure must result in cutting hard bone or other tissue while minimizing injury to adjacent soft tissue, among other considerations.

The cuts made by a bone saw are ideally flat in the plane of the bar and straight at the cut borders. This is needed to allow optimal healing when two bone surfaces are opposed, or one bone surface is opposed to an implant surface. Surfaces that are not in the same plane, or uneven surfaces, form empty gaps which may take a long time to heal or may never heal. Some saws tend to experience drifting away from the intended plane of the saw bar, called skiving, which is undesirable. Also, some saws have cutting elements that tend to experience a grabbing action that results in unguided movement of the bar, which is also undesirable.

In a surgical procedure, a bone saw is controlled by a surgeon in an operating room environment. Preferably the saw produces minimal vibration so that it can be easily controlled by the surgeon. This is important for multiple reasons. Bones are typically next to important and delicate soft tissue such as blood vessels and nerves, and uncontrolled movement can result in damage to such tissue. Also, uncontrolled movement can result in less desirable cuts.

Historically, for knee implant surgery, when very simplistic resurfacing of the articulating surfaces of the distal femur and proximal tibia and even the patella was performed (over 40 years ago), the cuts were made free hand in an iterative process of cutting and sizing of the bone to fit and align implants. Eventually, cutting blocks were employed that were fixed to the bone after being oriented and positioned to natural anatomical markers for depth of cut, flexion/extension, and varus/valgus positioning. The cutting blocks guide the saw blades to make cuts for knee implantations. This type of cutting block system is still used today, with tens of thousands of orthopedic sets of instruments used throughout the world. Generally, cutting blocks have specific sizes for the different sizes of knee implants, analogous to different sizes of shoes for people.

Chain saws have long been used in applications such as wood cutting; however, until now they have not been successfully deployed for common surgical use. This is due to many technical challenges of the chain saw for the specific requirements of bone or other surgery. U.S. Pat. No. 9,616,512 to Viola discloses a chain saw for cutting bone. The disclosure of U.S. Pat. No. 9,616,512 is hereby incorporated by reference herein in its entirety. U.S. Provisional Patent Application No. 63/058,216, filed Jul. 29, 2020, entitled "Thin Single Width Chain Saw," U.S. Provisional Patent Application No. 63/085,290, filed Sep. 30, 2020, entitled "Thin Single Width Chain Saw," U.S. Provisional Patent Application No. 63/147,033, filed Feb. 8, 2021, entitled "Chain Saws and Components for Chain Saws," U.S. Provisional Patent Application No. 63/154,379, filed Feb. 26, 2021, entitled "Systems and Methods for Manufacturing Saws and Saw Components," U.S. Provisional Patent Application No. 63/209,525, filed Jun. 11, 2021, entitled "Devices for Maintaining Tension in Chain Saws," U.S. Provisional Patent Application No. 63/209,540, filed Jun. 11, 2021, entitled "Systems for Robotic Surgery," U.S. Non-Provisional patent application Ser. No. 17/443,646, filed Jul. 27, 2021, entitled "Chain Saws, Components for Chain Saws, and Systems for Operating Saws," and International Application No. PCT/US2021/043433, filed Jul. 28, 2021, entitled "Chain Saws, Components for Chain Saws, and Systems for Operating Saws," the disclosures of which are incorporated by reference herein in their entirety, disclose chain saws, components for chain saws, methods of making chain saws and components, and methods of using chain saws and components.

There is a need for improvements in the cutting of bone and other objects, including in other fields (such as, e.g., construction). It would be advantageous to achieve one or more of the following advantages: lower cost, easier use, more precise alignment, more precise cuts, lower cutting time, lower procedure time, lower recovery time, and/or better outcomes.

SUMMARY

The present disclosure is directed to cutting guide systems for adjusting and stabilizing cutting devices. Certain embodiments of cutting guide systems disclosed herein may be used for adjusting and stabilizing cutting devices in orthopedic surgery, such as orthopedic knee surgery, spinal surgery, or other orthopedic surgery. Certain embodiments of cutting guide systems disclosed herein may be used for adjusting and stabilizing bone or tissue cutting devices, such as chain saws and other types of bone or tissue cutting saws. Certain embodiments of cutting guide systems disclosed herein may be used for adjusting and stabilizing cutting devices in other fields, such as construction. Certain embodiments of cutting guide systems disclosed herein may be used for adjusting and stabilizing devices for cutting wood, drywall, plastic, and other materials, such as chain saws and other types of cutting instruments.

In some examples, a cutting guide system for stabilizing a cutting instrument comprises a support mount attachable in a fixed relation with respect to an object to be cut by the cutting instrument, a joint, and a cutting instrument support, wherein the joint is adapted to permit the cutting instrument support to be adjusted with respect to the support mount. The joint may be adapted to permit the cutting instrument support to be rotated about at least two axes.

In some examples, the joint may comprise a ball and socket. The ball and socket may be lockable with respect to each other. The cutting instrument support may comprise a stem connected to the ball or the socket.

In some examples, the joint may comprise a first hinge comprising a first rod and a first opening, wherein the first rod is positioned in the first opening for relative rotational movement between the first rod and the first opening, allowing a first adjusting guide to pivot about a first axis with respect to the support mount. The first adjusting guide and the support mount may be lockable with respect to each other. The cutting guide system may further comprise a first transducer adapted to detect an amount of rotation of the first adjusting guide about the first axis.

In some examples, the joint may also comprise a second hinge comprising a second rod and a second opening, wherein the second rod is positioned in the second opening for relative rotational movement between the second rod and the second opening, allowing a second adjusting guide to pivot about a second axis with respect to the first adjusting guide. The second adjusting guide and the first adjusting guide may be lockable with respect to each other. The cutting guide system may further comprise a second transducer adapted to detect an amount of rotation of the second adjusting guide about the second axis.

In some examples, the cutting instrument support is adapted to support a cutting instrument such that the cutting instrument is pivotable with respect to the cutting instrument support. In some examples, the cutting instrument support may be adapted to support a cutting instrument such that the cutting instrument is movable back and forth in a longitudinal direction with respect to the cutting instrument support.

In some examples, the cutting instrument support may comprise a stem. The cutting instrument support may further comprise a first saw clamp and a second saw clamp. The position of the cutting instrument along a longitudinal axis of the stem may be adjustable. The position of the cutting instrument along the longitudinal axis of the stem may be lockable.

In some examples, the cutting instrument support may comprise a saw mount, wherein a position of the saw mount with respect to an adjusting guide is adjustable. The position of the saw mount with respect to the adjusting guide may be lockable.

In some examples, the stem is adapted to extend through a slot in the cutting instrument, such that the cutting instrument is pivotable with respect to the stem, and such that the cutting instrument is movable back and forth in a longitudinal direction with respect to the stem.

In some examples, the cutting instrument may comprise a saw. The cutting instrument may comprise a chain saw.

In some examples, the cutting guide system may further comprise a guide mount for positioning a cut mount block, wherein a position of the guide mount with respect to an adjusting guide is adjustable in a longitudinal direction. The cut mount block may be adapted to be fastened to the object to be cut by the cutting instrument. The cutting guide system may further comprise an adapter for mounting a cutting instrument on the cut mount block.

In some examples, a cutting guide system for stabilizing a cutting instrument comprises a track defining a path and a cutting instrument support, wherein the cutting instrument support is connected to the track in a manner that stabilizes the cutting instrument support with respect to the track while permitting the cutting instrument support to move in the direction of the path of the track.

In some examples, one of the track and the cutting instrument support may comprise a channel and the other of the track and the cutting instrument support may comprise a projection that fits within the channel, preventing separation of the cutting instrument support from the track, while permitting the cutting instrument support to move in the direction of the path of the track.

In some examples, the cutting instrument support comprises a stem, a first saw clamp, and a second saw clamp. The position of the cutting instrument along a longitudinal axis of the stem may be adjustable and lockable. The stem may be adapted to extend through a slot in the cutting instrument, such that the cutting instrument is pivotable with respect to the stem, and such that the cutting instrument is movable back and forth in a longitudinal direction with respect to the stem.

In some examples, a method of stabilizing a cutting instrument comprises: (i) attaching a support mount of a cutting guide system in a fixed relation with respect to an object to be cut by the cutting instrument, wherein the cutting guide system further comprises a joint and a cutting instrument support, and (ii) adjusting a position of the cutting instrument support with respect to the support mount by moving the cutting guide system at the joint. The method may further comprise, after adjusting the position of the cutting instrument support with respect to the support mount by moving the cutting guide system at the joint, locking the position of the cutting instrument support with respect to the support mount. The joint may comprise a ball and socket. The joint may comprise: (i) a first hinge comprising a first rod and a first opening, wherein the first rod is positioned in the first opening for relative rotational movement between the first rod and the first opening, allowing a first adjusting guide to pivot about a first axis with respect to the support mount, and (ii) a second hinge comprising a second rod and a second opening, wherein the second rod is positioned in the second opening for relative rotational movement between the second rod and the second opening, allowing a second adjusting guide to pivot about a second axis with respect to the first adjusting guide. The cutting instrument may be pivotable with respect to the cutting instrument support and movable back and forth in a longitudinal direction with respect to the cutting instrument support.

Further examples and features of embodiments of the invention will be evident from the drawings and detailed description.

BRIEF DESCRIPTION OF THE DRAWINGS

The accompanying drawings illustrate examples of devices, components, and methods disclosed herein and, together with the description, serve to explain the principles of the present disclosure.

FIG. 13 shows the cutting guide system of FIG. 6, with the second adjusting guide pivoted in a second direction around the second rod axis.

Figure 1:
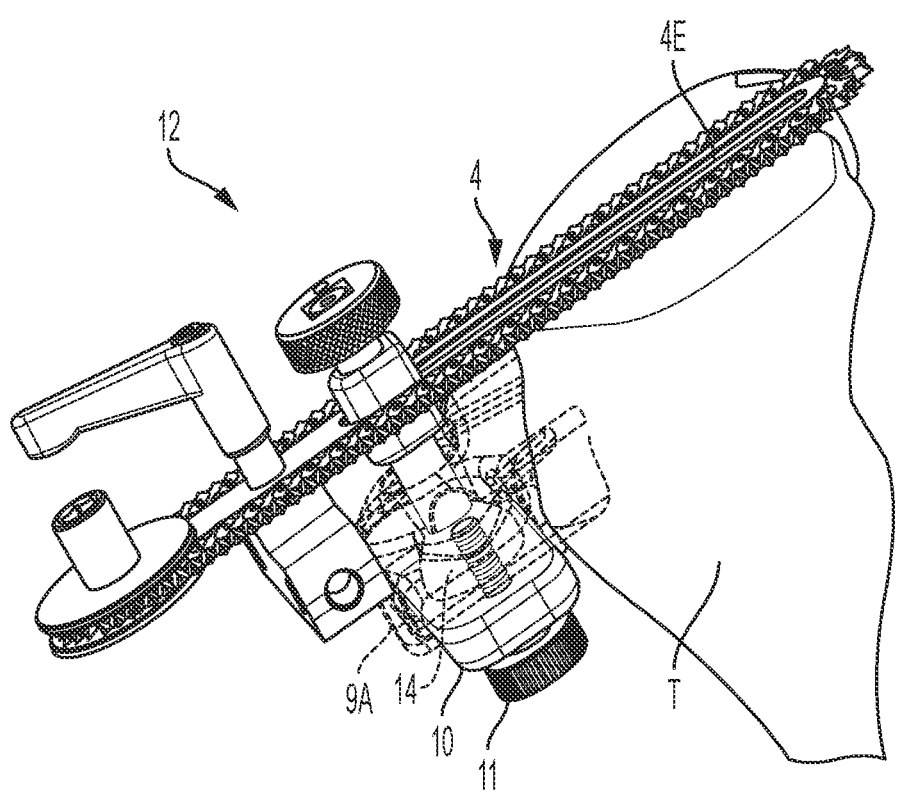
FIG. 1 shows an example of a cutting guide system in accordance with the disclosure.

The accompanying drawings may be better understood by reference to the following detailed description.

DETAILED DESCRIPTION

For the purposes of promoting an understanding of the principles of the disclosure, reference will now be made to the examples illustrated in the drawings, and specific language will be used to describe those and other examples. It will nevertheless be understood that no limitation of the scope of the claims is intended by the examples shown in the drawings or described herein. Any alterations and further modifications to the illustrated or described systems, devices, components, or methods, and any further application of the principles of the present disclosure, are fully contemplated as would normally occur to one skilled in the art to which the disclosure relates. In particular, the features, components, and/or steps described with respect to one implementation of the disclosure may be combined with features, components, and/or steps described with respect to other implementations of the disclosure.

The designations "first" and "second" as used herein are not meant to indicate or imply any particular positioning or other characteristic. Rather, when the designations "first" and "second" are used herein, they are used only to distinguish one component or part from another. The terms "attached," "connected," "coupled," and the like mean attachment, connection, coupling, etc., of one part to another either directly or indirectly through one or more other parts, unless direct or indirect attachment, connection, coupling, etc., is specified. The term "user" refers to one or more persons using the devices, systems, and/or methods described herein, such as one or more surgeons, physicians, operators, or other persons using the devices, systems, and/or methods.

FIG. 1 shows a first example embodiment of a cutting guide system 12. FIG. 1 shows the cutting guide system 12 attached to the proximal (upper) end of a generally vertically-oriented tibia bone T. FIG. 1 shows the cutting guide system 12 being used to guide a saw for a transverse cut being made in the tibia T in the horizontal plane of the human body.

Figure 2:
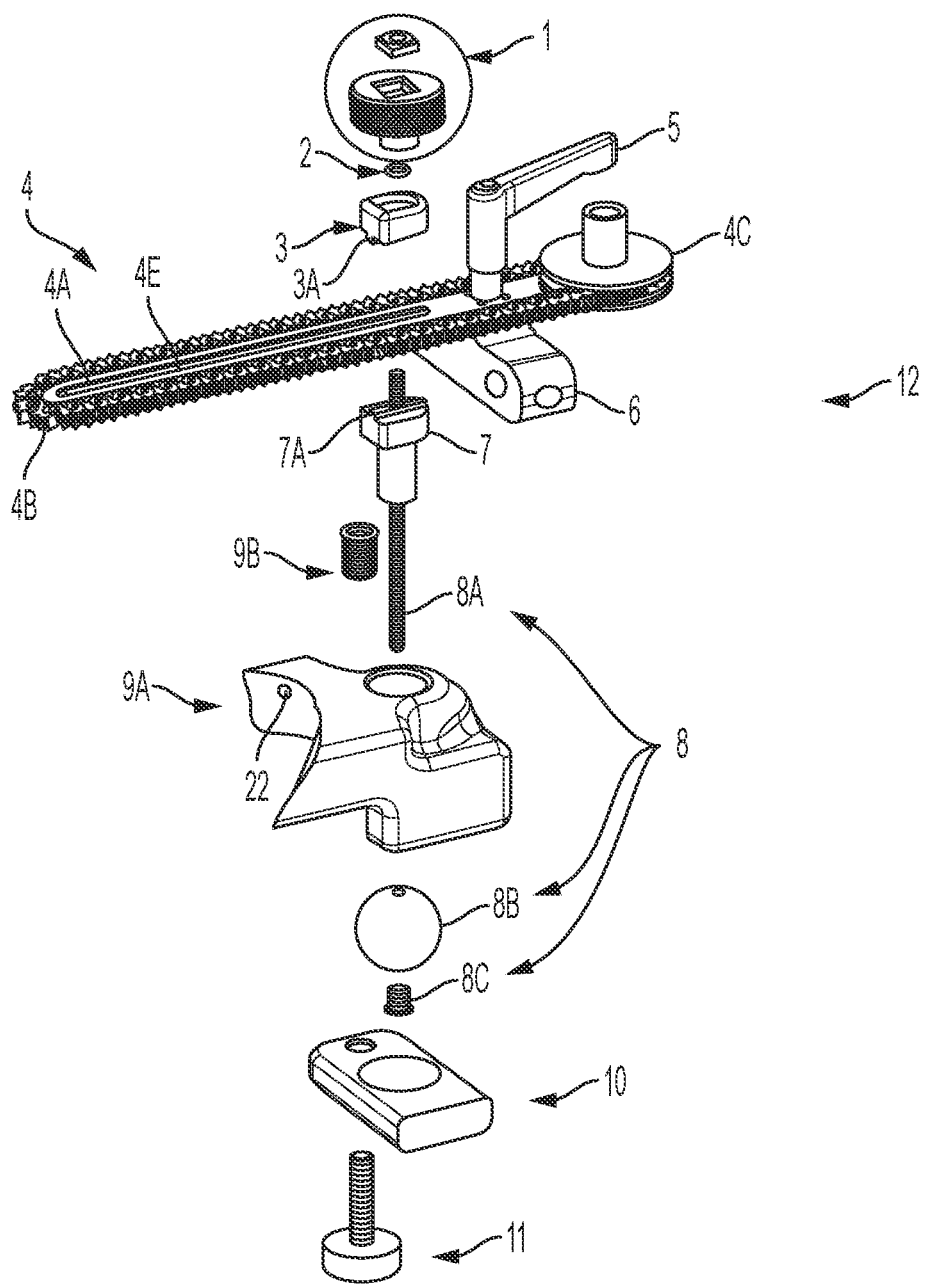
FIG. 2 shows an exploded view of the cutting guide system of FIG. 1.

FIG. 2 shows an exploded view of the cutting guide system 12, showing the individual components of the cutting guide system 12.

As shown in FIG. 1, the cutting guide system 12 includes a support mount 9A that is attachable to a bone, such as the proximal anterior tibia T. The support mount 9A may be attached to the bone in a conventional manner. For example, the support mount 9A may be attached to the bone by one or more fasteners that fit through one or more holes 22 in the support mount 9A and penetrate into the bone. The fasteners may be conventional fixation pins, trocar tipped pins, screws, and/or other fasteners. Additionally or alternatively, spikes may be located on the contacting face of the support mount 9A and may be driven into the bone to attach the support mount 9A to the bone and/or to aid in the stability and rigidity of the support mount 9A with respect to the bone. The support mount is attachable in a fixed relation with respect to the bone or other object to be cut by the cutting instrument either directly or through one or more other components.

As discussed in more detail below, when the support mount 9A is attached to the bone, the specific position as far as XYZ location and XYZ rotational orientation of the support mount 9A with respect to the bone is not critical. Without being restricted to a precise location and alignment, the user is able to position the support mount 9A onto a stable topography of the patient's bone. The proximal anterior tibia has a somewhat irregular shape due to the tibial tubercle, which is a bony eminence to anchor the quadricep patella flexion mechanism. Because the precise positioning of the support mount 9A with respect to the bone is not critical, the user can locate the support mount 9A on an area of the bone that will facilitate the stability of the support mount 9A.

FIG. 1 shows the support mount 9A as a translucent body in order to make visible the internal features, including areas sized and shaped to receive components of a ball and stem assembly 8, which in this embodiment is comprised of the parts labeled 8A, 8B, and 8C. The ball and stem assembly 8 comprises a stem 8A, a ball 8B, and in this embodiment a fastener 8C. The stem 8A extends through a bore through the ball 8B and is secured by the fastener 8C. In some embodiments the stem 8A and fastener 8C may be one component, such as a headed fastener wherein the head of the fastener does not fit through the bore that extends through the ball 8B. In some embodiments, the stem 8A and ball 8B may be manufactured as a single component, with the stem 8A and ball 8B connected together without the need for a fastener. A general overview is that the ball and stem assembly 8, when assembled, resembles an upside-down spherical lollipop.

When the cutting guide system 12 is assembled, the ball and stem assembly 8 fits in a socket of the cutting guide system 12. The socket 14 may comprise a recess in a lower block 10 and a recess in the support mount 9A. The recesses may be partially spherical (e.g., hemispherical) or any other suitable shape. The two recesses form a socket 14 in which the ball 8B fits. The ball 8B, in conjunction with the socket 14 of the cutting guide system 12 in which the ball 8B is received, serves as a swivel joint which has degrees of freedom in all planes. When positioned within the socket 14, the ball 8B of the ball and stem assembly 8 rotates as a ball joint in all degrees of freedom within the socket 14 of the cutting guide system 12. This allows the stem 8A to be oriented at various angles and to be rotated. As examples of permitted directions of movement, the joint (ball 8B and socket 14) allows the stem 8A to be pivoted to the right and left, around a first axis, and toward and away from the object to be cut (e.g., the bone), around a second axis.

The swivel joint from the ball 8B and socket 14 gives the user ultimate flexibility as to where to position the bone cuts. The ball 8B is completely free to rotate in the socket 14 formed by the recesses in the lower block 10 and the support mount 9A until the user tightens lock 11 which forces the lower block 10 toward the support mount 9A and creates a pressure against the ball 8B that prevents the ball 8B from rotating. The recesses in the lower block 10 and the support mount 9A may be sized so that they clamp the ball 8B between them when the lock 11 is deployed. In this embodiment, the lock 11 is a bolt that goes through a hole in the block 10 and screws into a threaded insert 9B that goes through a hole in the support mount 9A, or alternatively into a threaded hole of the support mount 9A. Other mechanisms may be used for the lock 11, such as other locking (fastening, clamping, or securing) mechanisms. When the user has maneuvered the ball and stem assembly 8 to the desired position, the user may then deploy the lock 11 to fix the position. If the user wants to readjust the position, the lock may be released (e.g., rotated in the reverse direction), the ball and stem assembly 8 may be repositioned, and the lock 11 may be deployed again.

The cutting guide system 12 further comprises lower saw clamp 7 and upper saw clamp 3 for securing opposite sides of the saw 4. In this example, the stem 8A (either alone or in conjunction with the lower saw clamp 7 and upper saw clamp 3) forms a cutting instrument support for supporting the saw 4 or other cutting instrument. The saw clamps 3, 7 have through-holes for accommodating the stem 8A so that the stem 8A extends through the through-holes of both saw clamps 3, 7. The positioning of the saw clamps 3, 7 along the longitudinal length of the stem 8A is adjustable. For example, the through-holes of the saw clamps 3, 7 may be sized so that they slide over the stem 8A, and an adjustable spacer may be used to adjust the position of the saw clamp 7 with respect to the support mount 9A. An example of a suitable adjustable spacer is described below.

When assembled, the lower saw clamp 7 and the upper saw clamp 3 are secured on opposite sides of a saw 4, with the stem 3A extending through a slot 4E in the saw 4. In this embodiment, the saw 4 is a chain saw assembly comprising a saw bar 4A, a chain 4B, and a drive cog assembly 4C. The illustrated chain saw assembly may be attached to and driven by a handpiece (not shown). Components 5 and 6 represent components of the saw for handling the saw and/or attachment of the saw to a driving mechanism. While a chain saw is illustrated, other types of saws may be secured by the cutting guide system 12.

The saw clamp 3 and/or the saw clamp 7 may have a ridge 3A, 7A on its side that faces the saw, wherein the ridge fits within the slot 4E of the saw bar. The ridge or ridges help guide the longitudinal movement of the saw.

The saw clamp 7 may be adjusted to the desired position by the adjustable spacer as described above, then the knob 1 may be rotated to force the saw clamp 3 against saw clamp 7. The knob 1 may have an internally threaded nut or bore that mates with a threaded outer surface of the stem 8A, such that rotation of the knob 1 causes the knob 1 to move down the stem 8A, thereby forcing the saw clamp 3 toward the saw clamp 7 to secure the saw 4. A spring 2 may be used to bias saw clamp 3 toward saw clamp 7 to help secure the saw 4 between saw clamp 3 and saw clamp 7. The securement of the saw between the saw clamps 3, 7 prevents the saw from moving up or down the stem 8A, while still allowing the saw bar 4A to move in a direction parallel to the length of the saw bar slot 4E, by advancing forward or pulling back. In the example of FIG. 1, advancing the saw bar 4A forward with respect to the support mount 9A comprises moving the saw bar 4A posteriorly, while pulling the saw bar 4A back comprises moving the saw bar 4A anteriorly. Thus, the cutting instrument (e.g., saw) is movable back and forth in a longitudinal direction with respect to the cutting instrument support (e.g., stem 8A).

In some embodiments, the saw clamps 3, 7 may be rotatable around the stem 8A. In this arrangement, the saw can rotate in a plane about the stem 8A, wherein the axis of the stem 8A is the axis of rotation. This allows the user to move the saw not only in the forward and back direction but also rotationally in a plane about the axis of the stem 8A. Thus, the cutting instrument (e.g., saw) may be pivotable with respect to the cutting instrument support (e.g., stem 8A).

In use, the cutting guide system 12 allows for simple securement of the cutting guide system 12 to the bone, simple positioning of the saw 4 with respect to the bone, and simple readjustment of that positioning if needed. The user first attaches the support mount 9A to the bone. As mentioned above, the particular position and orientation of the support mount 9A with respect to the bone is not critical, allowing the user to select a securement position on the bone that allows for stable fixation. The joint (ball 8B and socket 14) permits the cutting instrument support (e.g., stem 8A) to be adjusted with respect to the support mount 9A. With the support mount 9A attached to the bone, the user maneuvers the ball and stem assembly 8 to the desired position. Then, the user deploys the lock 11 to fix that position. If the user wants to readjust the position, the lock may be released, the ball and stem assembly 8 may be repositioned, and the lock 11 may be deployed again. Then, with the ball and stem assembly 8 locked, the user may adjust the position of the saw clamps 3, 7 along the longitudinal length of the stem 8A. This position may be locked, and if the user wants to readjust, the position may be unlocked and the saw clamps 3, 7 may be repositioned.

In an example procedure, knee surgery, the positioning may include considerations such as balancing the medial and lateral collateral ligaments as well as the anterior and posterior cruciate ligaments and the capsule of the knee. The primary adjustments may be for flexion/extension and varus/valgus positioning. The final adjustments may be for the amount of bone one is cutting off. In the example of knee surgery and the tibia, this final adjustment may be for the amount of bone one is cutting off with respect to the long axis of the tibia.

Alignment guides and styluses and/or preoperative planning may be used to assist in referencing of landmarks for the proper placement for the positioning of the implants, for example for total knee arthroplasty. The goal in such knee surgery is to recreate the normal anatomical kinematics of the knee while also balancing the soft tissue structures and maintaining overall stability through range of motion.

A design as described above has additional advantages. The cutting guide system can be designed to be usable with a range of different implant sizes. Thus, the cutting guide system can replace the multiple different cutting blocks currently needed in a range of sizes, e.g., seven or eight different sizes of cutting block systems. Thus, a cutting guide system as described herein can significantly reduce required inventory and uses less hospital storage space. A cutting guide system as described herein may also be advantageous for portable military or hospital locations where an effective cutting system with fewer components may be valuable. In addition, in some embodiments, the simple design of a cutting guide system as described herein lends itself to disposable instruments.

FIG. 3 and FIGS. 4A-4F illustrate another example embodiment of a cutting guide system 30. The cutting guide system 30 includes a track 32. The track 32 may have a curved shape, such as an arc having a desired radius of curvature and length.

The track 32 may be attachable to a stem of a swivel joint, such as the stem 8A of the cutting guide system 12. Thus, for example, the cutting guide system 30 may include the following components of the cutting guide system 12: support mount 9A, one or more fasteners for attaching the support mount 9A to bone, ball and stem assembly 8 (stem 8A, ball 8B, and optional fastener 8C), lower block 10 (wherein recesses in the lower block 10 and the support mount 9A form a socket 14 for the ball 8B), lock 11 (with optional corresponding threaded insert 9B or threaded hole of the support mount 9A, or other locking mechanism). The user uses these components in the same manner as described above, i.e., attaching the support mount 9A to bone, maneuvering the ball and stem assembly 8 to place the stem 8A in the desired position, and then locking the ball and stem assembly 8 in place with the lock 11 or other locking mechanism.

In such an embodiment, the track 32 may be attached above the top of the stem 8A. The stem 8A may be shorter than illustrated in FIGS. 1-2, and the track 32 may be attached to the stem 8A either directly or through one or more other components. An adjustable spacer may be used to adjust the spacing of the track 32 with respect to the support mount 9A.

In an alternative cutting guide system, the track 32 may be attached directly to bone, or connected to a block that is attached directly to bone. The track 32 may be used with or without a swivel joint. The ends of the track 32 may be secured to the bone for stability.

The curved shape of the track 32 is shaped for the desired target location, e.g., shaped to go around the desired bone location. This allows close proximity of the track 32 to the bone as it wraps around the bone.

Figure 3:
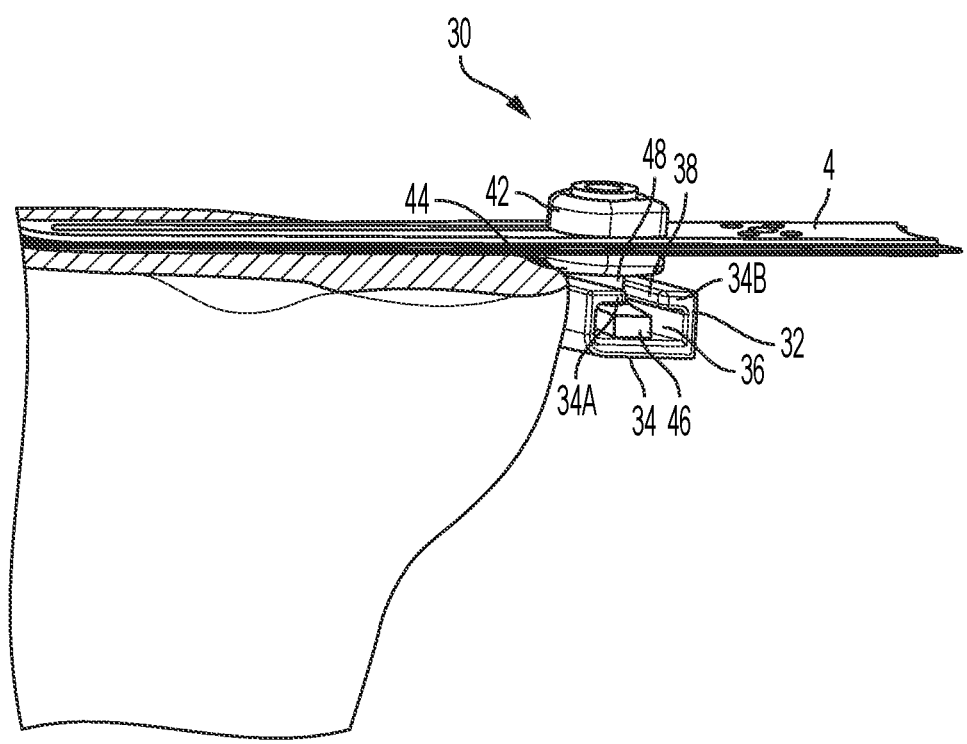
FIG. 3 shows another example of a cutting guide system in accordance with the disclosure.

As can be seen in FIG. 3, the track 32 has a wall 34 forming a channel 36. A narrow slot 38 in the upper wall accesses the channel 36, with wall portions 34A, 34B on either side of the slot 38.

The cutting guide system 30 further comprises an upper saw clamp 42 and a lower saw clamp 44 for securing opposite sides of the saw 4 and for guiding the saw 4 with respect to the track 32. The lower saw clamp 44 has a projection 46 that fits within the channel 36 of the track 32 and a stem 48 that connects the projection 46 with the main body of the lower saw clap 44. In this example, the stem 48 (either alone or in conjunction with the lower saw clamp 44 and upper saw clamp 42) forms a cutting instrument support for supporting the saw 4 or other cutting instrument. The stem 48 may extend through a slot in the cutting instrument (e.g., saw 4), such that the cutting instrument is pivotable with respect to the stem 48, and such that the cutting instrument may be movable back and forth in a longitudinal direction with respect to the stem 48. The stem 48 extends through the slot 38 in the track 32 while the projection 46 is too large to fit through the slot 38. This is like a dovetail configuration, preventing separation of the saw clamp 44 from the track 32. This arrangement keeps the saw 4 connected to the track 32 while allowing the projection 46 to slide within the channel 36. This allows lower saw clamp 44, and thereby the upper saw clamp 42 and saw 4, to move in the direction of the slot 38, which in this case follows the curved path of the track 32.

When assembled, the lower saw clamp 44 and the upper saw clamp 42 are secured on opposite sides of a saw 4. While a chain saw is illustrated, other types of saws may be secured by the cutting guide system 30. The saw bar 4A has a saw bar slot 4E in it through which the saw clamps 42, 44 connect, while allowing the saw bar 4A to move longitudinally in the direction of the saw bar slot 4E. The saw clamps 42, 44 prevent the saw 4 from moving away from the track 32 while allowing the saw 4 to move along the direction of the slot 38 of the track and also still allowing the saw bar 4A to move in a direction parallel to the length of the slot 4E in the saw bar 4A, by advancing forward or pulling back. The upper saw clamp 42 and the lower saw clamp 44 may each have a ridge, like the ridge 3A or 7A, on its side that faces the saw, wherein the ridge fits within the slot 4E of the saw bar. The ridge or ridges help guide the longitudinal movement of the saw.

Figure 4A:
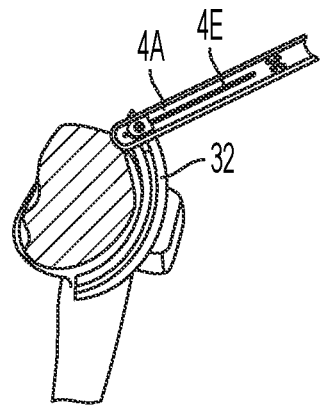
FIG. 4A shows the cutting guide system of FIG. 3, showing a saw starting a cut from the right side.
Figure 4B:
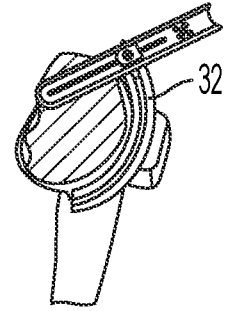
FIG. 4B shows the cutting guide system of FIG. 3, showing a saw plunging from the position of FIG. 4A.
Figure 4C:
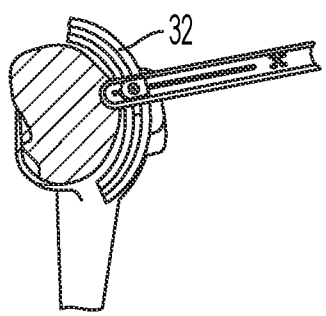
FIG. 4C shows the cutting guide system of FIG. 3, showing a saw toward the middle of the bone to be cut.
Figure 4D:
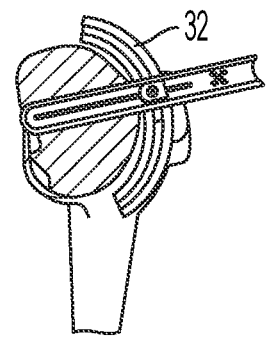
FIG. 4D shows the cutting guide system of FIG. 3, showing a saw plunging from the position of FIG. 4C.
Figure 4E:
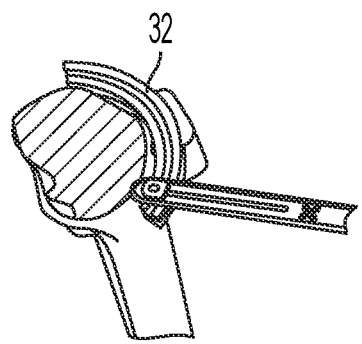
FIG. 4E shows the cutting guide system of FIG. 3, showing a saw starting a cut from the left side.
Figure 4F:
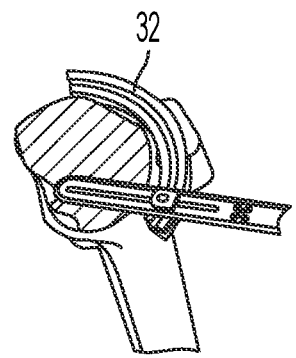
FIG. 4F shows the cutting guide system of FIG. 3, showing a saw plunging from the position of FIG. 4E.

FIGS. 4A-4F show various positions of a saw 4 using the cutting guide system 30. FIGS. 4A-F show the cut starting (FIG. 4A) and plunging from the right (FIG. 4B), sweeping towards the middle plunging in or going laterally (FIGS. 4C-D) and then continuing on all the way to the left (FIGS. 4E-F).

The cutting guide system 30 has advantages as described above with respect to cutting guide system 12 while allowing the user to cut the bone from many more positions. The track 32 defines a path, and the cutting instrument support is connected to the track in a manner that stabilizes the cutting instrument support with respect to the track 32 while permitting the cutting instrument support to move in the direction of the path of the track 32.

While FIG. 3 and FIGS. 4A-4F illustrate the track 32 having a channel 36 and the cutting instrument support having a projection 46 that fits within the channel 36, other arrangements are possible for connecting the cutting instrument support to the track in a manner that permits the cutting instrument support to move in the direction of the path of the track. For example, the cutting instrument support may have a channel (like the channel 36 of the track 32 described above) with a slot (like the slot 38), and the track may have a projection that fits within the channel, with a narrow area between the main body of the track and the projection. The narrow area fits within the slot, like a dovetail configuration, preventing separation of the cutting instrument support from the track, while allowing the cutting instrument support to move in the direction of the path of the track.

Figure 5A:
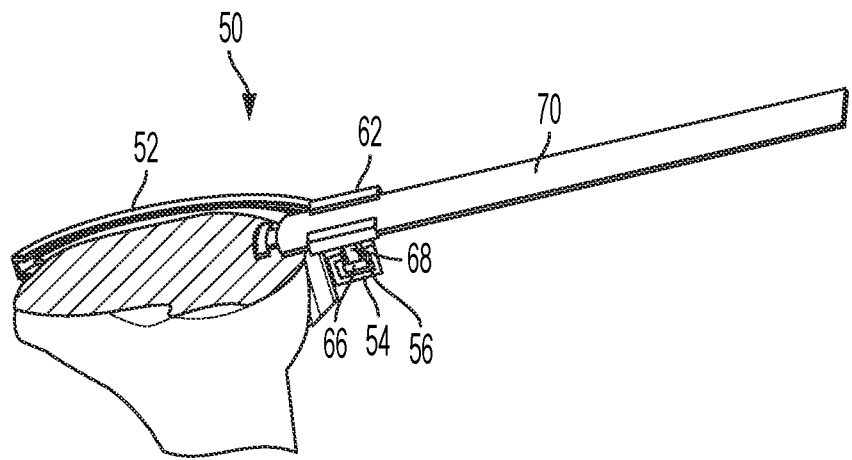
FIG. 5A shows another example of a cutting guide system in accordance with the disclosure.
Figure 5B:
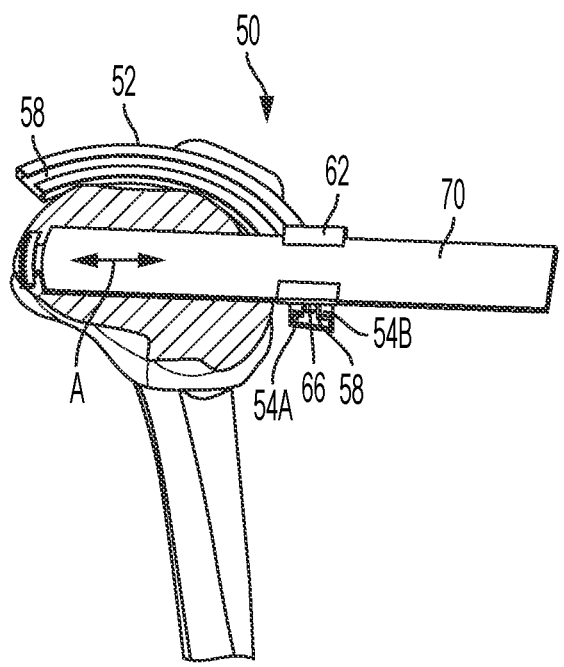
FIG. 5B shows another view of the cutting guide system of FIG. 5A.
Figure 5C:
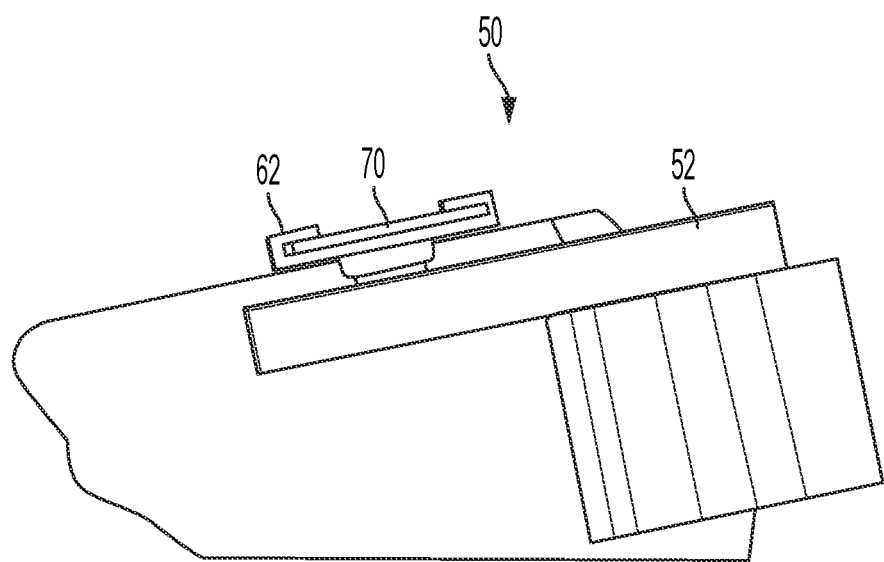
FIG. 5C shows another view of the cutting guide system of FIG. 5A.
Figure 6:
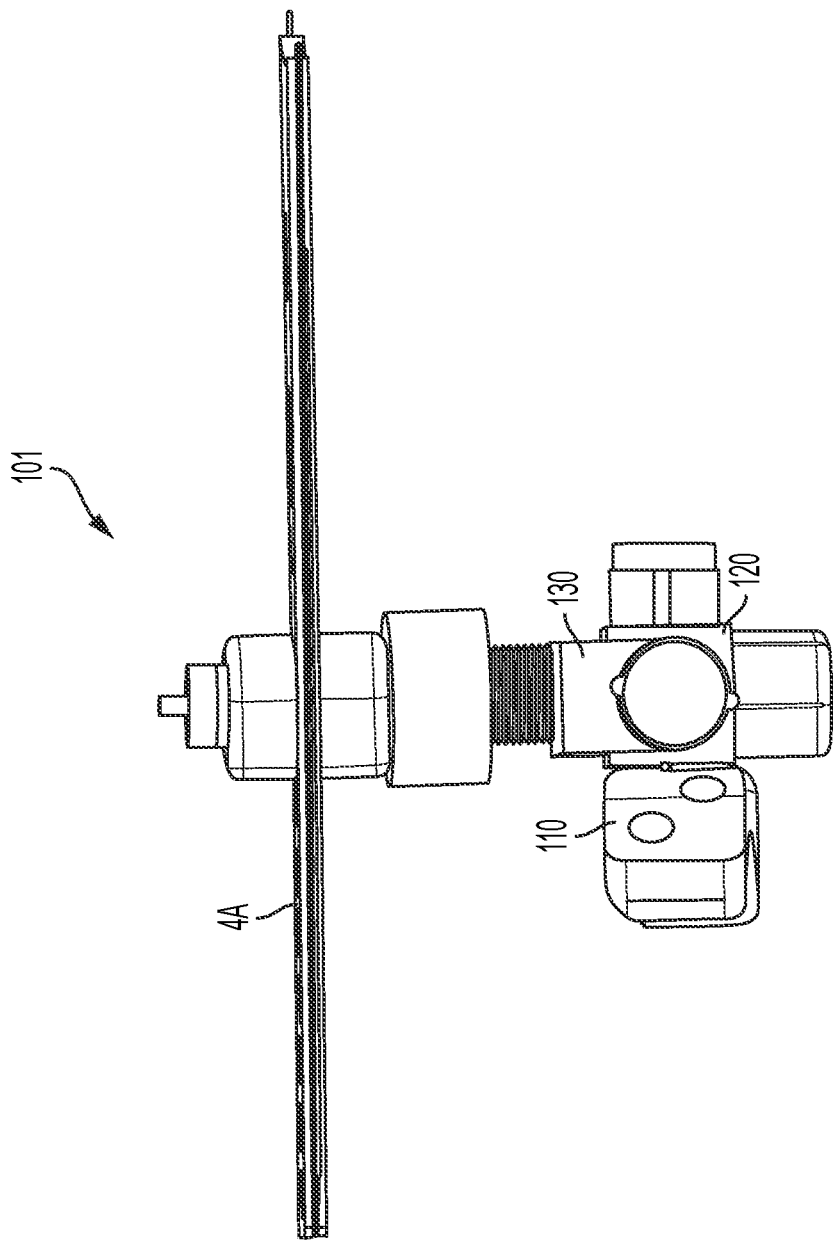
FIG. 6 shows another example of a cutting guide system in accordance with the disclosure.
Figure 7:
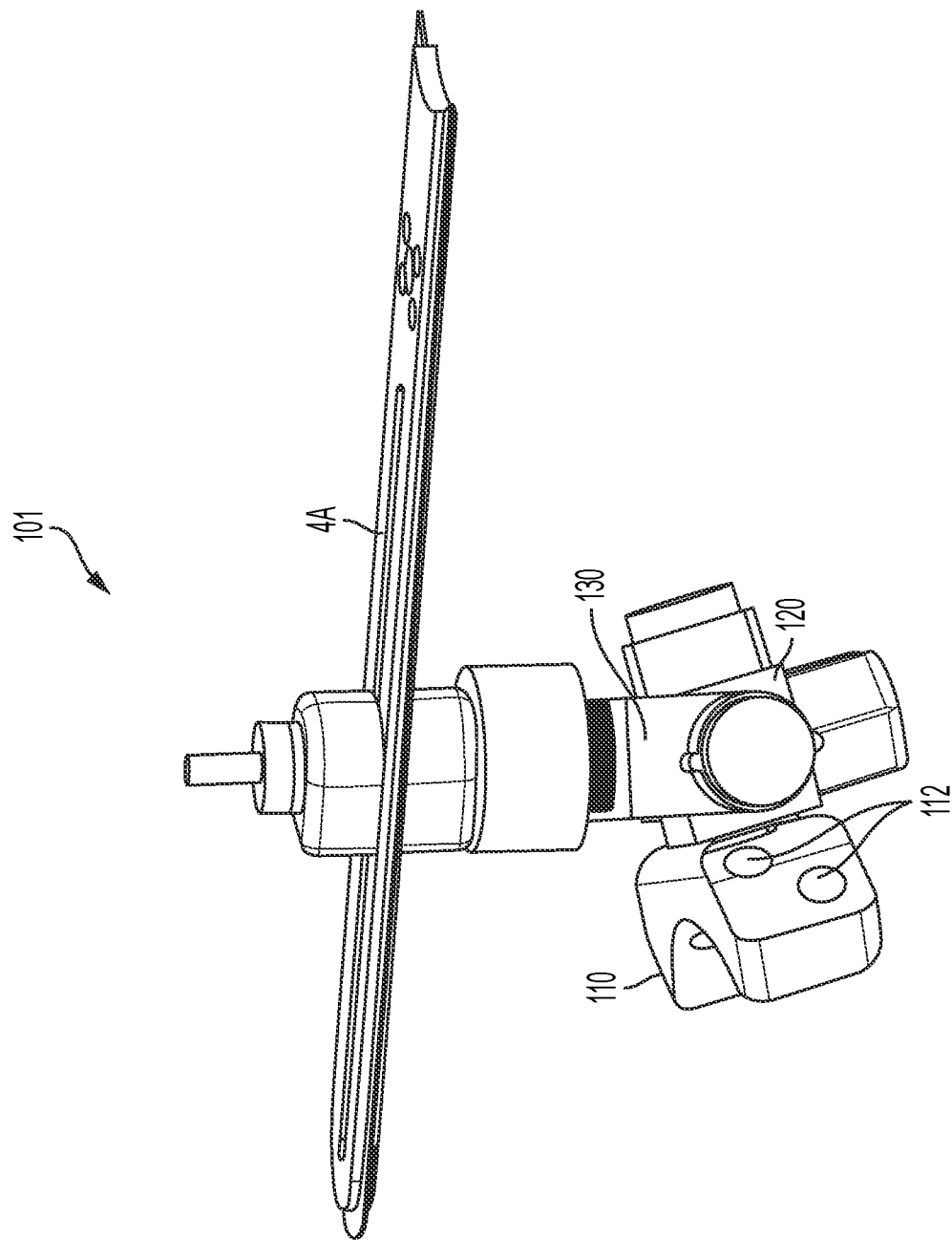
FIG. 7 shows another view of the cutting guide system of FIG. 6.
Figure 8:
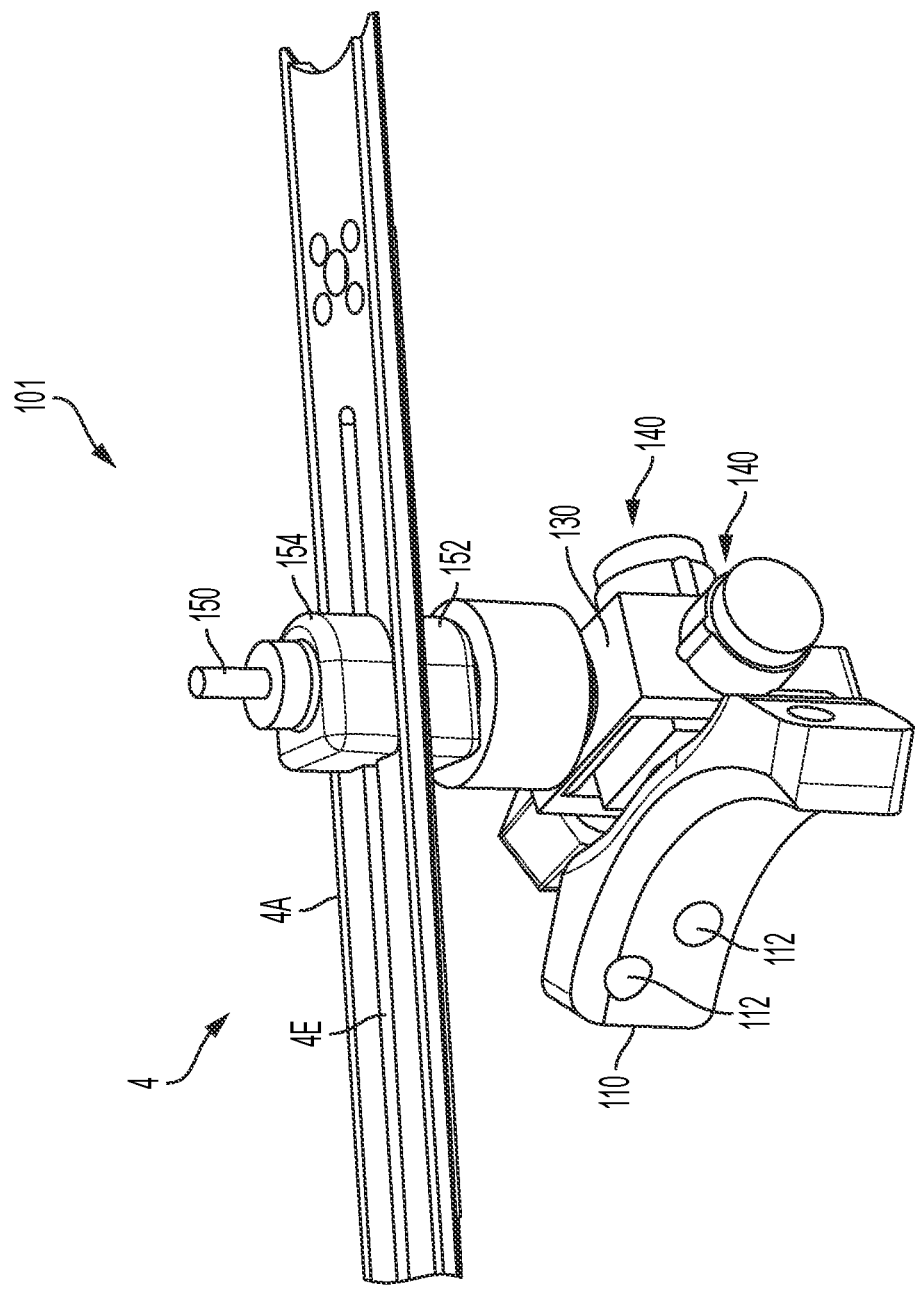
FIG. 8 shows another view of the cutting guide system of FIG. 6.
Figure 9:
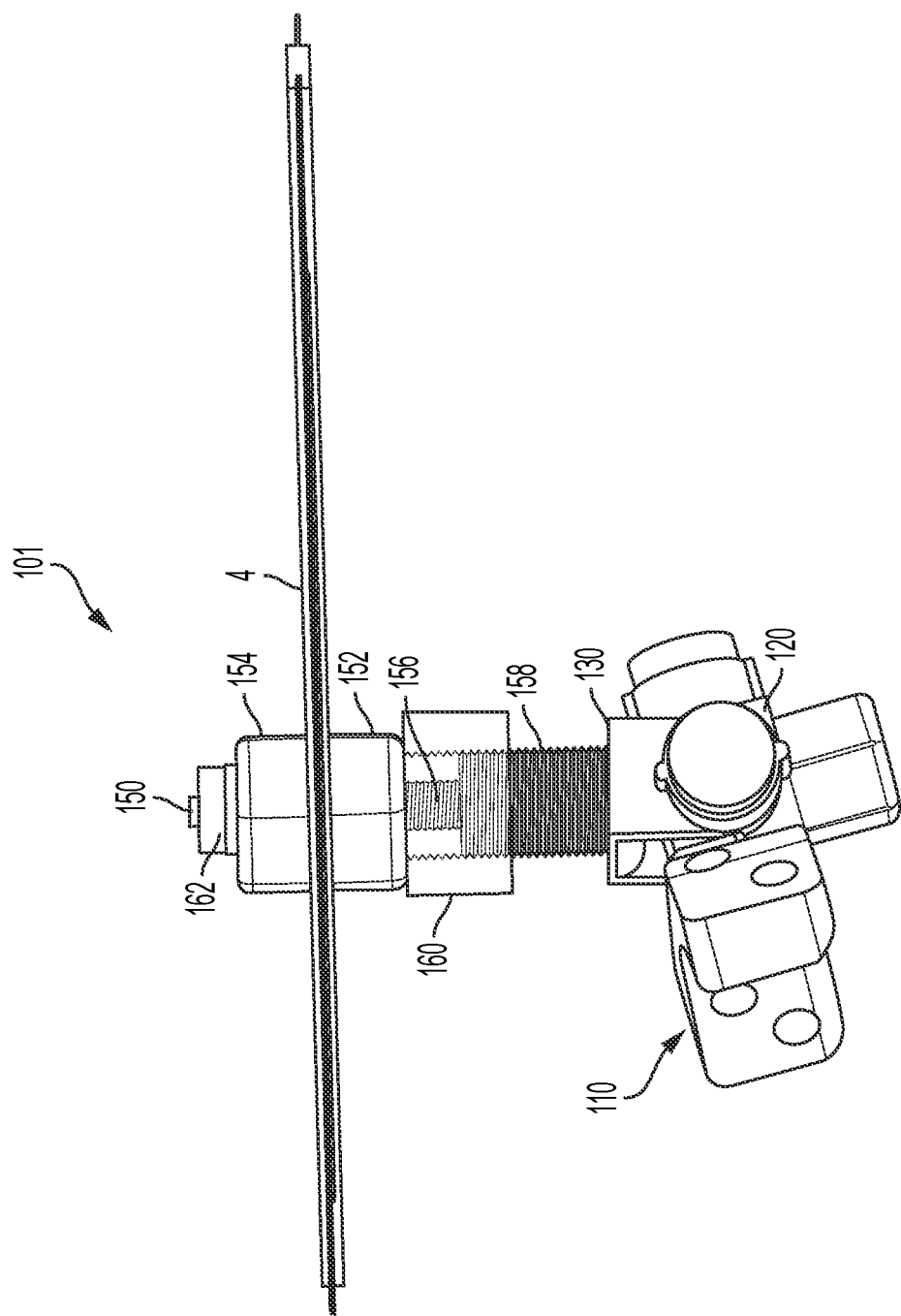
FIG. 9 shows another view of the cutting guide system of FIG. 6.

FIGS. 5A-5C illustrate another example embodiment of a cutting guide system 50. The cutting guide system 50 includes a track 52, similar to the track 32 described above. The track 52 may have a curved shape, such as an arc having a desired radius of curvature and length.

Like the track 32, the track 52 may be attachable to a stem of a swivel joint, such as the stem 8A of the cutting guide system 12. Thus, for example, the cutting guide system 50 may include the following components of the cutting guide system 12: support mount 9A, one or more fasteners for attaching the support mount 9A to bone, ball and stem assembly 8 (stem 8A, ball 8B, and optional fastener 8C), lower block 10 (wherein recesses in the lower block 10 and the support mount 9A form a socket 14 for the ball 8B), lock 11 (with optional corresponding threaded insert 9B or threaded hole of the support mount 9A, or other locking mechanism). The user uses these components in the same manner as described above, i.e., attaching the support mount 9A to bone, maneuvering the ball and stem assembly 8 to place the stem 8A in the desired position, and then locking the ball and stem assembly 8 in place with the lock 11 or other locking mechanism.

In such an embodiment, the track 52 may be attached above the top of the stem 8A, similar to the attachment of the track 32. The track 52 may be attached to the stem 8A either directly or through one or more other components. An adjustable spacer may be used to adjust the spacing of the track 52 with respect to the support mount 9A.

Similar to track 32, the track 52 may be attached directly to bone, or connected to a block that is attached directly to bone. The track 52 may be used with or without a swivel joint. The ends of the track 52 may be secured to the bone for stability.

Similar to track 32, the curved shape of the track 52 is shaped for the desired target location, e.g., shaped to go around the desired bone location. This allows close proximity of the track 52 to the bone as it wraps around the bone.

As can be seen in FIGS. 5A and 5B, the track 52 has a wall 54 forming a channel 56. A narrow slot 58 in the upper wall accesses the channel 56, with wall portions 54A, 54B on either side of the slot 58.

The cutting guide system 50 further comprises an adapter 62 for securing a saw blade 70 and for guiding the saw blade 70 with respect to the track 52. In this example, the adapter 62 forms a cutting instrument support for supporting the saw blade 70 or other cutting instrument. The cutting instrument may be movable back and forth in a longitudinal direction with respect to the adapter 62. The bottom of the adapter 62 has a projection 66 that fits within the channel 56 of the track 52 and a stem 68 that connects the projection 66 with the main body of the adapter 62. The stem 68 extends through the slot 58 while the projection 66 is too large to fit through the slot 58. This is like a dovetail configuration, preventing separation of the adapter 62 from the track 52. This arrangement keeps the saw 70 connected to the track 52 while allowing the projection 66 to slide within the channel 56. This allows adapter 62, and thereby the saw 70, to move in the direction of the slot 58, which in this case follows the curved path of the track 52.

As shown in FIG. 5C, the adapter 62 has an opening for receiving the saw 70, with sides and top wall sections for securing the saw 70, allowing the saw to move longitudinally back and forth along one axial line as shown. The illustrated saw is a precision saw blade. One example of such a saw blade is a precision saw blade available from Stryker, example part number 6526-127-105. Other types of saws may be secured by the cutting guide system 50. The adapter 62 prevents the saw 70 from moving away from the track 52 while allowing the saw to move along the direction of the slot 58 of the track 52 and also still allowing the saw bar 70 to move in a direction parallel to the length of the saw bar, designated by the arrow A in FIG. 5B, by advancing forward or pulling back.

The adapter 62 could have many different configurations, including spring-loaded, lockable, fully enclosed, and dovetail mechanisms, that would hold the saw blade in the plane of the bone cut as described. This system allows, as shown in FIG. 5B, the advancement of the saw blade without relinquishing the planar guidance.

FIG. 5B shows the saw blade 70 being controlled to produce a flat plane or cut. FIG. 5B illustrates the advancement of the cutting blade from the anterior part of the tibia towards the posterior region of the bone in preparation for a prosthetic tibial resurfacing implant. Using the cutting guide 50, the saw blade 70 may be positioned in a similar manner as shown in FIGS. 4A-4F.

FIG. 5C shows a method of the encapsulation of the blade 70 by the adapter 62. This configuration allows for controlling the blade, stabilizing the blade while still enabling the blade to advance or retract (in the direction of arrow A in FIG. 5B) depending upon the user's requirements.

Like the cutting guide system 30, the cutting guide system 50 has advantages as described above with respect to cutting guide 12 while allowing the user to cut the bone from many more positions. The track 52 defines a path, and the cutting instrument support (adapter 62) is connected to the track in a manner that stabilizes the cutting instrument support with respect to the track 52 while permitting the cutting instrument support to move in the direction of the path of the track 52.

As discussed above with respect to FIG. 3 and FIGS. 4A-4F, while FIGS. 5A-5C illustrate the track 52 having a channel 56 and the cutting instrument support having a projection 66 that fits within the channel 56, other arrangements are possible for connecting the cutting instrument support to the track in a manner that permits the cutting instrument support to move in the direction of the path of the track. For example, the cutting instrument support may have a channel (like the channel 56 of the track 52 described above) with a slot (like the slot 58), and the track may have a projection that fits within the channel, with a narrow area between the main body of the track and the projection. The narrow area fits within the slot, like a dovetail configuration, preventing separation of the cutting instrument support from the track, while allowing the cutting instrument support to move in the direction of the path of the track.

The interface between the adapter and the saw blade can take various forms. It may be spring-loaded, may be fixed or adjustable, may have coatings or comprise a plastic bushing, or may have any of various mechanisms that would isolate vibrations while at the same time allowing for smooth advancement and control of the planar cutting. One of the advantages of a system such as the cutting guide system 30 or the cutting guide system 50 is that it allows the saw blade to be held much closer to the bone. The ability to hold the saw blade closer to the material that is to be resected can significantly improve the accuracy of the bone cut as compared to current cutting blocks. The stability also aids in the safety aspect of controlling a reciprocating vibrating saw.

An additional advantage of certain cutting guide systems as described herein is that the system can provide an accessible frame of reference for visualization. For example, the user can view the top of the adapter 62. The top section of the adapter is a visually accessible frame of reference to read plunging depth marks that may be marked on the blade. With this arrangement, the user has a much more exacting and visual reference of the depth of cut.

In some embodiments, the plunging depth could be measured by an electronic linear measuring device and the measurements could be transmitted, e.g., via Bluetooth or Wi-Fi, to a workstation that has information regarding the procedure.

Persons of ordinary skill in the art will appreciate that cutting guide systems as described herein not only can guide saws without the existing cumbersome cut blocks, embodiments can be tailored to different types of saws, including chain saws and saws that only oscillate and/or reciprocate at the tip, as well as other saws. The saws can be accommodated with saw bar slots (such as saw bar slot 4E), guided with fitted adapters that secure the saw while allowing longitudinal motion (such as adapter 62), or held in another manner that secures the saw while allowing longitudinal motion consistent with the disclosure. Various such embodiments may be used with a swivel joint and/or a curved track as described herein.

Embodiments as described herein may be used in various ways. For example, they may be used manually or used with robotic platforms, wherein the saw is maneuvered robotically.

Figure 14A:
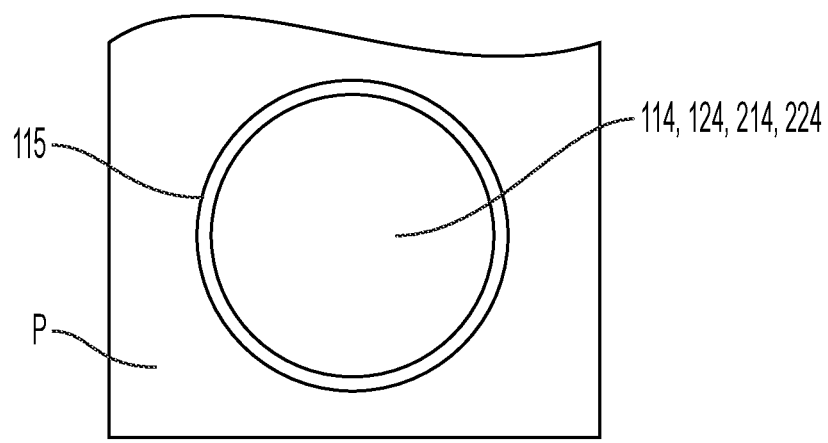
FIG. 14A shows a schematic illustration of an example of a hinge with a rod positioned in an opening for relative rotational movement between the rod and the opening.
Figure 14B:
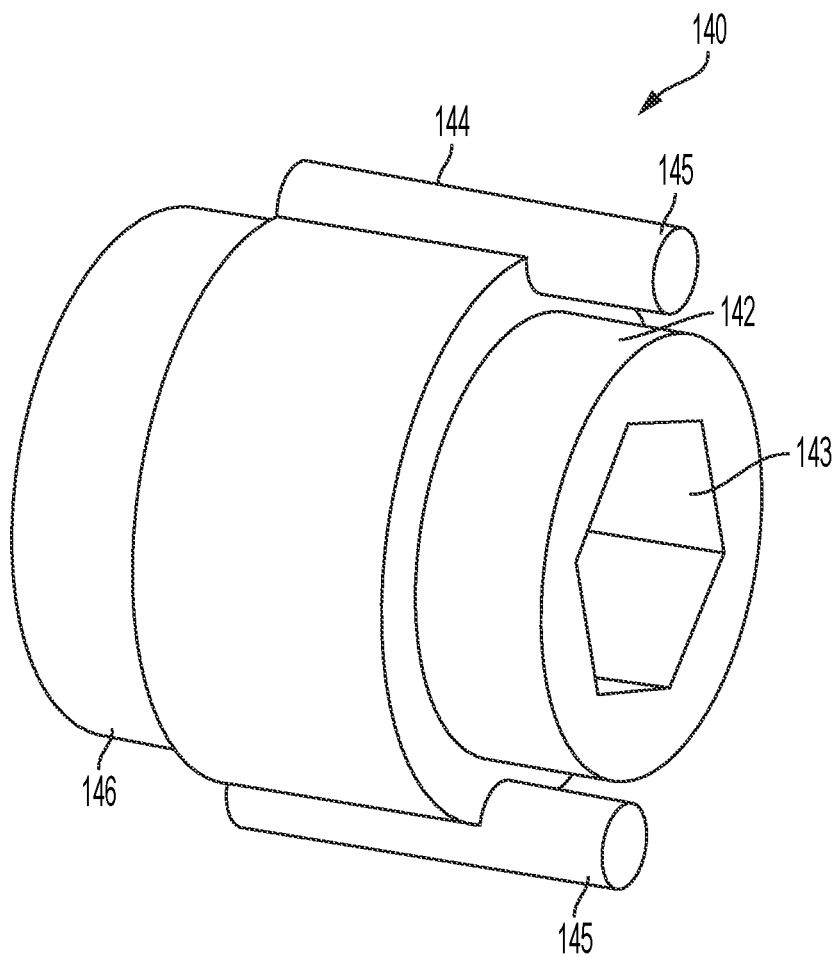
FIG. 14B shows an example transducer that may be incorporated as part of a cutting guide system in accordance with the disclosure, such as the cutting guide system of FIG. 6.
Figure 15:
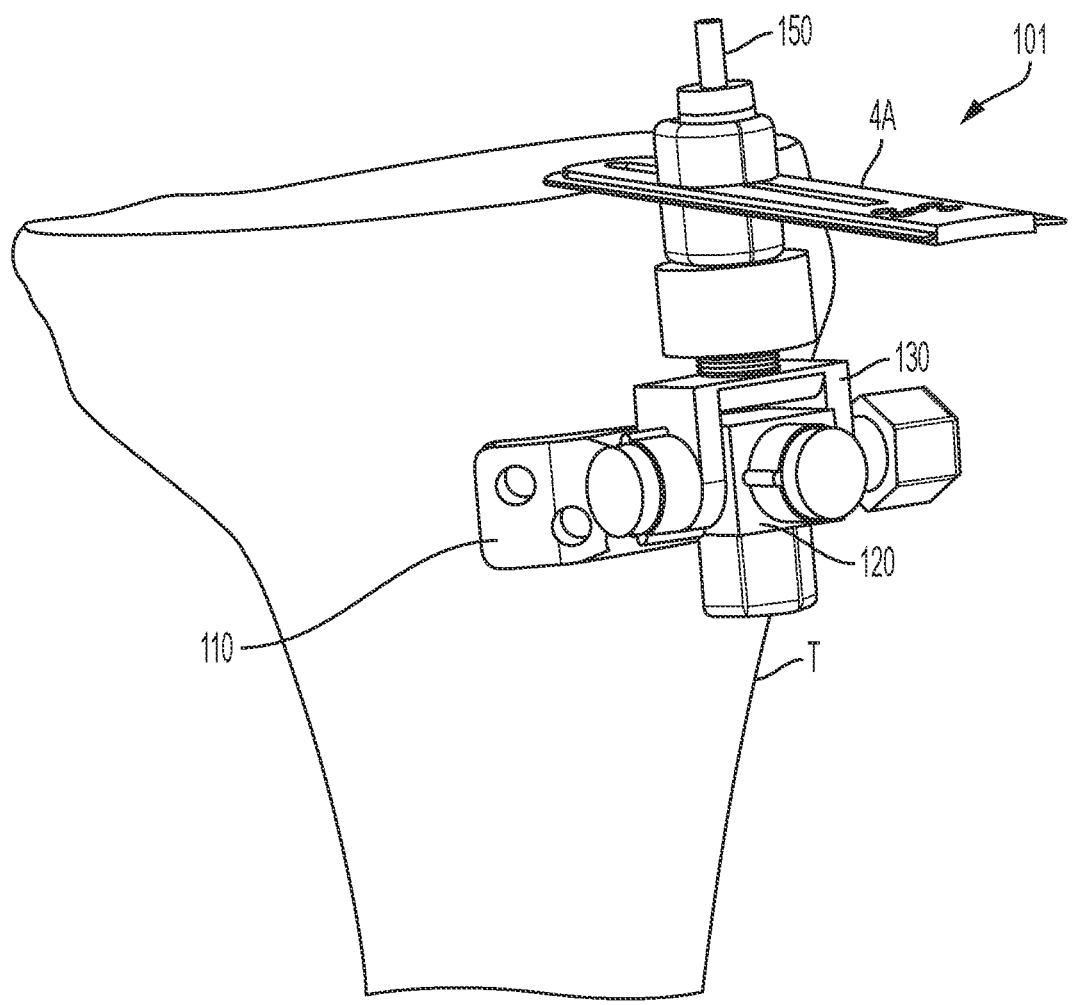
FIG. 15 shows the cutting guide system of FIG. 6 mounted for cutting a bone.

FIGS. 6 to 15 show another example embodiment of a cutting guide system 101. FIG. 15 shows the cutting guide system 101 attached to the proximal (upper) end of a tibia bone T. FIG. 15 shows the cutting guide system 101 being used to guide a saw for a transverse cut being made in the tibia T in the horizontal plane of the human body.

The cutting guide system 101 includes a support mount 110 that is attachable to a bone, such as the proximal anterior tibia T shown in FIG. 15 or another suitable bone. The support mount 110 may be attached to the bone in a conventional manner. For example, the support mount 110 may be attached to the bone by one or more fasteners that fit through one or more holes 112 in the support mount 110 and penetrate into the bone. The fasteners may be conventional fixation pins, trocar tipped pins, screws, and/or other fasteners. Additionally or alternatively, spikes may be located on the contacting face of the support mount 110 and may be driven into the bone to attach the support mount 110 to the bone and/or to aid in the stability and rigidity of the support mount 110 with respect to the bone. The support mount 110 is attachable in a fixed relation with respect to the bone or other object to be cut by the cutting instrument either directly or through one or more other components.

When the support mount 110 is attached to the bone, the specific position as far as location and rotational orientation of the support mount 110 with respect to the bone is not critical. Without being restricted to a precise location and alignment, the user is able to position the support mount 110 onto a stable topography of the patient's bone. Because the precise positioning of the support mount 110 with respect to the bone is not critical, the user can locate the support mount 110 on an area of the bone that will facilitate the stability of the support mount 110.

A first rod 114 is a part of, or is rigidly attached to, the support mount 110. When the support mount 110 is attached to bone, the first rod extends away from the bone. The axis 114A of the first rod is labeled in FIGS. 10 and 11. A first adjusting guide 120 is mounted on the first rod for rotation about the first rod and the first rod axis 114A. The first adjusting guide 120 has an opening (recess or hole) in which the first rod is positioned for relative rotational movement, allowing the first adjusting guide 120 to rotate about the first rod and the first rod axis 114A. In an alternative arrangement, the first rod may be part of, or rigidly attached to, the first adjusting guide 120, and the support mount 110 may have a corresponding opening (recess or hole) for receiving the first rod. In this alternative arrangement, the first rod rotates with the first adjusting guide 120 (i.e., the first rod rotates within the opening in the support mount 110). In either arrangement, the first adjusting guide 120 is mounted for rotation with respect to the support mount 110 around the first rod axis 114A.

A second rod 124 may be a part of, or rigidly attached to, the first adjusting guide 120, extending laterally therefrom. The axis 124A of the second rod is labeled in FIGS. 12 and 13. A second adjusting guide 130 is mounted on the second rod for rotation about the second rod and the second rod axis 124A. The second adjusting guide 130 has an opening (recess or hole) in which the second rod is positioned for relative rotational movement, allowing the second adjusting guide 130 to rotate about the second rod and the second rod axis 124A. In an alternative arrangement, the second rod may be part of, or rigidly attached to, the second adjusting guide 130, and the first adjusting guide 120 may have a corresponding opening (recess or hole) for receiving the second rod. In this alternative arrangement, the second rod rotates with the second adjusting guide 130 (i.e., the second rod rotates within the opening in the first adjusting guide 120). In either arrangement, the second adjusting guide 130 is mounted for rotation with respect to the first adjusting guide 120 around the second rod axis 124A.

The first rod and/or the second rod need not extend continuously through the part with which it is associated. For example, the second rod may comprise two rod portions extending from either side of the first adjusting guide 120 or one rod portion extending from one side of the first adjusting guide 120. The first rod and the corresponding opening in which it is positioned for relative rotation together form a first hinge, allowing the first adjusting guide 120 to pivot about the first axis 114A. The second rod and the corresponding opening in which it is positioned for relative rotation together form a second hinge, allowing the second adjusting guide 130 to pivot about the second axis 124A. In this example, the joint for positioning the cutting instrument comprises the first hinge and the second hinge. Thus, as examples of permitted directions of movement, the joint allows the cutting instrument support to be pivoted to the right and left, around the first axis 114A, and toward and away from the object to be cut (e.g., the bone), around the second axis 124A. A schematic illustration of an example of a hinge with a rod 114, 124, 214, 224 positioned in an opening 115 for relative rotational movement between the rod and the opening is shown in FIG. 14A. The rod may rotate within the opening, and/or the part P having the opening (e.g., an adjusting guide) may rotate around the rod. The wall defining the opening 115 may extend 360 degrees around the corresponding rod or less than 360 degrees (e.g., 270 degrees, 225 degrees, etc.) around the corresponding rod.

A locking mechanism 126 is associated with the first adjusting guide 120 for selectively allowing the first adjusting guide 120 to rotate about the first rod axis 114A or preventing the first adjusting guide 120 from rotating about the first rod axis 114A. In the illustrated embodiment, the locking mechanism 126 comprises a set screw 128 that can be turned to securely engage the first rod, thereby locking the first adjusting guide 120 against rotation, or turned in the opposite direction to release the first rod, thereby allowing the first adjusting guide 120 to rotate about the first rod axis 114A. Similarly, a locking mechanism 136 is associated with the second adjusting guide 130 for selectively allowing the second adjusting guide 130 to rotate about the second rod axis 124A or preventing the second adjusting guide 130 from rotating about the second rod axis 124A. In the illustrated embodiment, the locking mechanism 136 comprises a set screw 138 that can be turned to securely engage the second rod, thereby locking the second adjusting guide 130 against rotation, or turned in the opposite direction to release the second rod, thereby allowing the second adjusting guide 130 to rotate about the rod axis 124A. Other locking (fastening, clamping, or securing) mechanisms may be used for the locking mechanisms 126 and 136.

The first adjusting guide 120 and the second adjusting guide 130 may have transducers 140 associated with them. The transducers 140 are adapted to detect an amount of rotation of the adjusting guides 120, 130 about their respective axes of rotation 114A, 124A. The transducers 140 convert the rotational movement of the adjusting guides 120, 130 into an electrical signal so that the user can get an accurate measurement of the angular positions of the adjusting guides 120, 130. Thus, the transducers 140 can be electronic devices that output the angular change or position of the respective adjusting guide 120 or 130 to the user.

An example transducer 140 is shown in FIG. 14B. In this illustrated example, the transducer includes a stator 142 and a rotor 144. The stator 142 is adapted to remain rotationally fixed while the rotor 144 is adapted to rotate with the adjusting guide 120 or 130 as the adjusting guide 120 or 130 rotates about its respective rod axis 114A or 124A. The stator 142 may be coupled to the rod. For example, in the illustrated embodiment the stator has an engagement recess 143 (for example, hexagonal or another shape) for mating with a correspondingly-shaped outer surface of the rod. The rotor 144 may be coupled to the adjusting guide 120 or 130. For example, the rotor may have pins 145 that engage into corresponding holes in the adjusting guide 120 or 130 so that the rotor 144 rotates with the adjusting guide 120 or 130.

The transducer 140 may further include a housing 146 that houses the components for converting the rotational movement of the adjusting guide 120 or 130 into an electrical signal. Various mechanism may be used for this conversion. For example, the mechanism may be a potentiometer, optical encoder, capacitance-based device, or other suitable mechanism. The housing 146 may also house a battery and/or a transmitter, such as a Bluetooth transmitter or other wireless transmitter, for transmitting the signal. For example, the signal may be transmitted via Bluetooth or other transmission to a device, such as a computer, handheld device, cell phone, iPad, or surgical station, that can be read by the user.

The cutting guide system 101 further comprises a stem 150 that is attached to or integral with the second adjusting guide 130. In the illustrated example, the stem 150 extends from the top of the second adjusting guide 130 and comprises a lower section 158 having a first diameter and an upper section 156 having a second diameter, wherein the first diameter is larger than the second diameter. The lower section 158 and the upper section 156 may be threaded.

The cutting guide system 101 further comprises a lower saw clamp 152 and an upper saw clamp 154 for securing opposite sides of a saw 4. The saw clamps 152, 154 have through-holes for accommodating the stem 150 so that the stem 150 extends through the through-holes of both saw clamps 152, 154. The positioning of the saw clamps 152, 154 along the longitudinal length of the stem 150 may be adjustable (in alternative embodiments, the positioning of the saw clamps 152, 154 along the longitudinal length of the stem 150 may be fixed). For example, the through-holes of the saw clamps 152, 154 may be sized so that they slide over the stem 150, and a lower adjusting nut 160 that is in threaded engagement with the lower section 158 of the stem 150 may be used to adjust the position of the lower saw clamp 152 with respect to the second adjusting guide 130. Once the lower adjusting nut 160 and lower saw clamp 152 are in position, the upper saw clamp 154 may be tightened into position by an upper adjusting nut 162 that is in threaded engagement with the upper section 156 of the stem 150. An optional spring may be used to bias the saw clamps together to help secure the saw 4 between the saw clamps.

When assembled, the lower saw clamp 152 and the upper saw clamp 154 are secured on opposite sides of the saw 4, with the stem 150 extending through a slot 4E in the saw 4. In this example, the stem 150 (either alone or in conjunction with the lower saw clamp 152 and upper saw clamp 154) forms a cutting instrument support for supporting the saw 4 or other cutting instrument. The stem 150 may extend through a slot 4E in the cutting instrument (e.g., saw 4), such that the cutting instrument is pivotable with respect to the stem 150, and such that the cutting instrument may be movable back and forth in a longitudinal direction with respect to the stem 150. In this embodiment, the saw 4 is a chain saw assembly comprising a saw bar 4A, a chain, and a drive cog assembly. The illustrated chain saw assembly may be attached to and driven by a handpiece (not shown). While a chain saw is illustrated, other types of saws may be secured by the cutting guide system 101.

The saw clamp 152 and/or the saw clamp 154 may have a ridge on its side that faces the saw, wherein the ridge fits within the slot 4E of the saw bar. The ridge or ridges help guide the longitudinal movement of the saw.

The securement of the saw between the saw clamps 152, 154 prevents the saw from moving up or down the stem 150, while still allowing the saw bar 4A to move in a direction parallel to the length of the saw bar slot 4E, by advancing forward or pulling back. In the example of FIG. 15, advancing the saw bar 4A forward with respect to the support mount 110 comprises moving the saw bar 4A posteriorly, while pulling the saw bar 4A back comprises moving the saw bar 4A anteriorly.

In some embodiments, the saw clamps 152, 154 may be rotatable around the stem 150. In this arrangement, the saw can rotate in a plane about the stem 150, wherein the axis of the stem 150 is the axis of rotation. This allows the user to move the saw not only in the forward and back direction but also rotationally in a plane about the axis of the stem 150.

Figure 10:
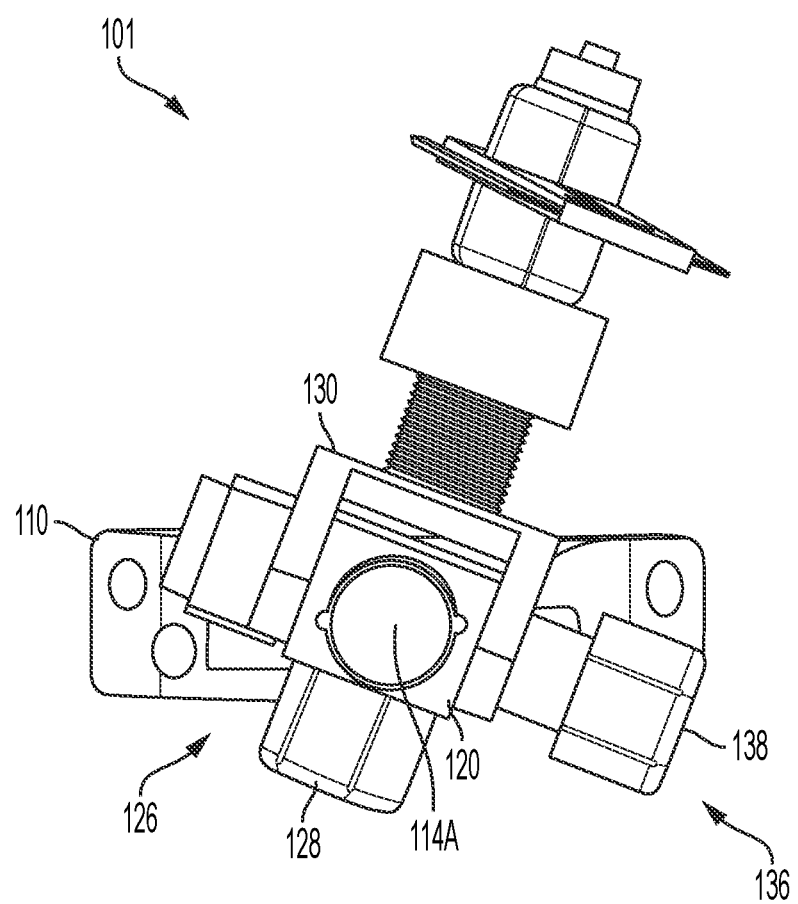
FIG. 10 shows the cutting guide system of FIG. 6, with a first adjusting guide pivoted in a first direction around a first rod axis.
Figure 11:
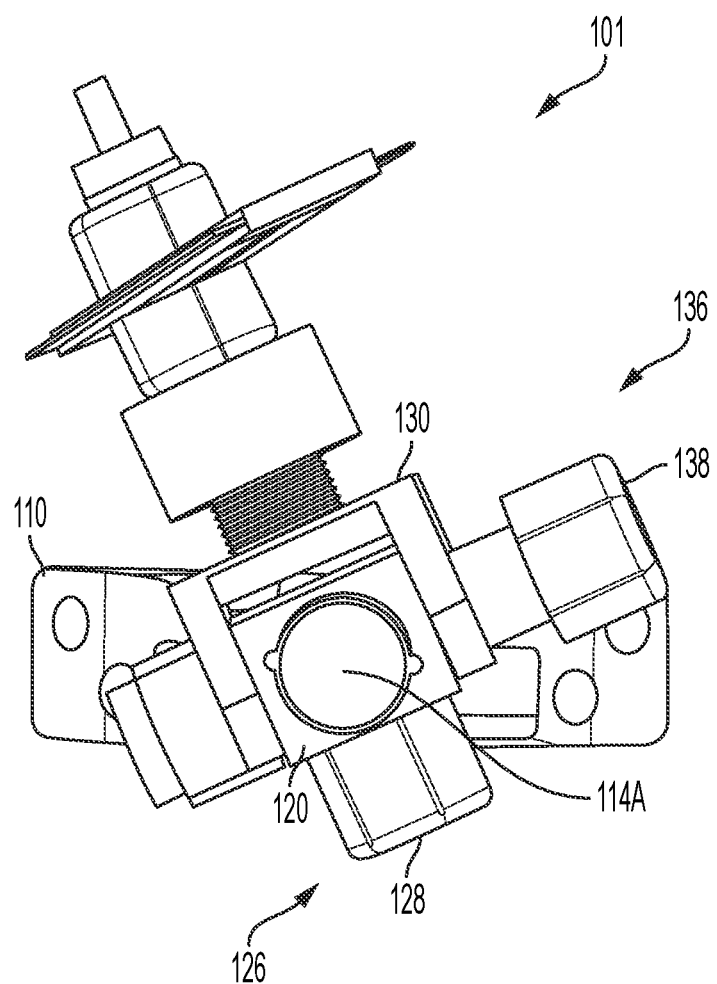
FIG. 11 shows the cutting guide system of FIG. 6, with the first adjusting guide pivoted in a second direction around the first rod axis.

An example of using the cutting guide system 101 is as follows. First, the user secures the support mount 110 to the bone. Next, the user may rotate the first adjusting guide 120 or the second adjusting guide 130 into a desired position. With a mounting as shown in FIG. 15, adjusting the first adjusting guide 120 can adjust the valgus/varus positioning, as shown in FIGS. 10 and 11. The user can evaluate the alignment visually, with or without additional alignment instruments such as alignment rods attachable to the first adjusting guide 120, with reference to anatomical landmarks, such as on the tibia or the center of the ankle. Once the first adjusting guide 120 is in the desired position, the user can lock its position using the locking mechanism 126, e.g., by tightening the set screw 128.

Figure 12:
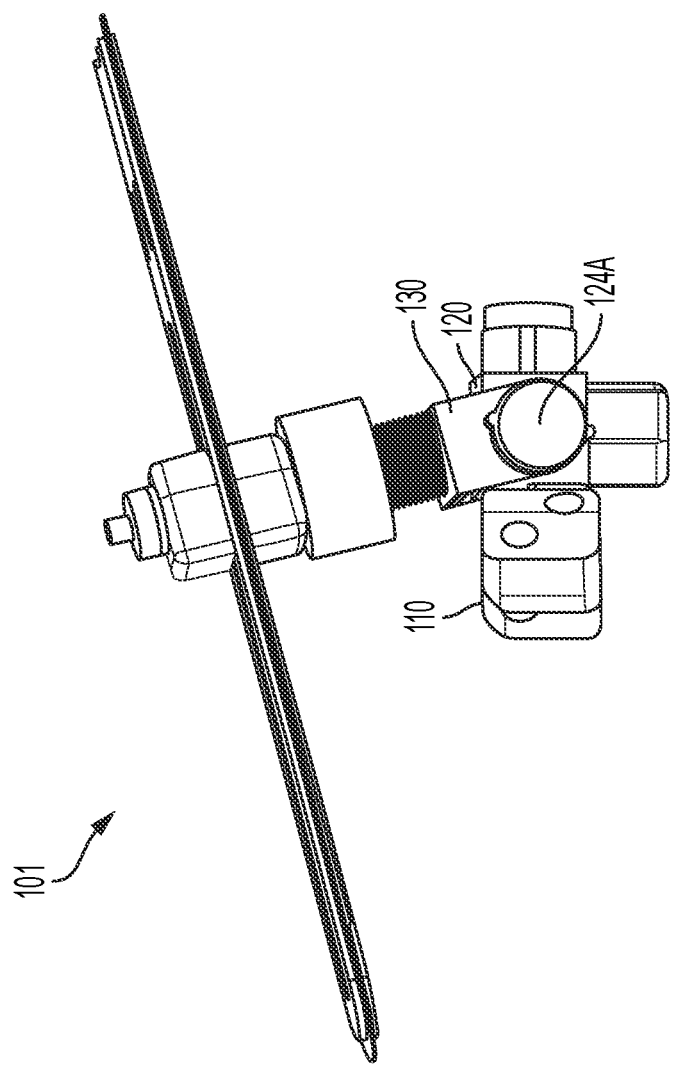
FIG. 12 shows the cutting guide system of FIG. 6, with a second adjusting guide pivoted in a first direction around a second rod axis.

Then, the user can adjust the other adjusting guide. With a mounting as shown in FIG. 15, adjusting the second adjusting guide 130 can adjust the flexion/extension positioning, as shown in FIGS. 12 and 13. The user can evaluate the alignment visually, with or without additional alignment instruments such as alignment rods attachable to the second adjusting guide 130. Once the second adjusting guide 130 is in the desired position, the user can lock its position using the locking mechanism 136, e.g., by tightening the set screw 138. The first adjusting guide 120 may be adjusted before the second adjusting guide 130, or vice versa.

A stylus may be used the measure the desired height adjustment for the amount of bone to be removed. For example, a stylus may be positioned in the place of the saw bar 4A. The saw clamps 152, 154 and/or adjusting nuts 160, 162 may be used with the stylus or removed for the stylus mechanism. With the stylus, the user would have the ability to determine the desired height for the saw. Then the stylus can be removed and the saw put in place with its height adjusted to the desired height, using the saw clamps 152, 154 and the adjusting nuts 160, 162.

In making the various positionings, the user can be guided using, and/or the information can be coordinated with, optical vision systems, preoperative evaluations, x-rays, CAT scans, MRIs, etc. At any point, the user can release a locking mechanism 126, 136, readjust the respective adjusting guide 120, 130, and then deploy the respective locking mechanism 126, 136 to secure the adjusting guide 120, 130. Similarly, the user can readjust the saw bar height by releasing the adjusting nuts 160, 162, adjusting the height, then relocking the saw.

The rotational position of the adjusting guides 120, 130 can be transmitted using the transducers 140 as described above. The user can use the position information to make the positionings and/or adjustments and/or additional cuts. For example, if the user wanted an extra two degrees of cut, the user could reset a first cut position at zero and move the adjusting mechanism two degrees, using the feedback from the transducer 140. As an option, the cutting guide system 101 could have a worm gear or linkage arrangement whereby fine rotating adjustments to the adjusting guides 120, 130 could be made, like a micrometer, to dial in a very specific degree of rotation. As another option, the cutting guide system could be adjusted using one or more motors, such as a stepper motor, for moving the adjusting guide 120 and/or 130.

The cutting guide system 101 isolates the two primary degrees of freedom with the independent adjustability of the first adjusting guide 120 and the second adjusting guide 130. The user can align the cutting guide system 101 in one plane or degree of freedom, lock it into place, and then adjust it in the other plane or degree of freedom. Thus, for example, the user can isolate the varus/valgus adjustment independently from the flexion/extension adjustment.

Figure 16:
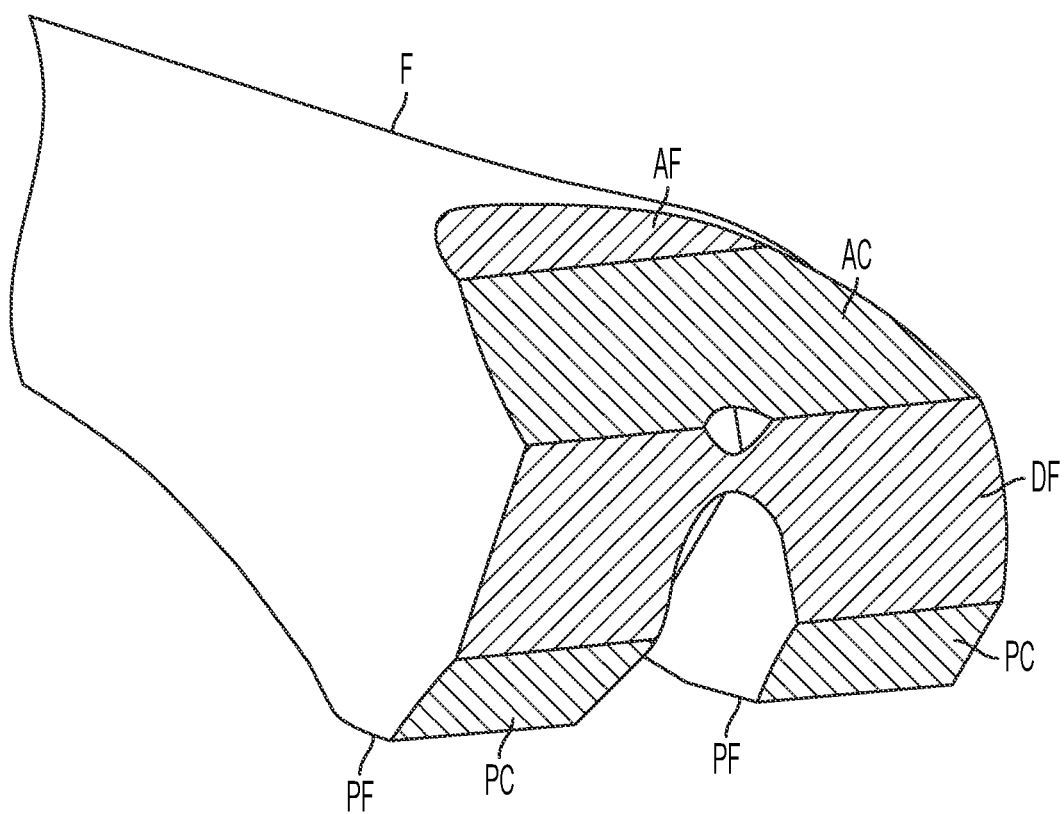
FIG. 16 shows some typical bone cuts made in a femur for knee replacement surgery.

FIG. 16 illustrates some typical bone cuts made in a femur F for knee replacement surgery. FIG. 16 illustrates the distal end of the femur F, i.e., the end facing the knee. The following bone cuts have been made in the femur F shown in FIG. 16: distal femur cut DF, anterior femur cut AF, posterior femur cut(s) PF, anterior chamfer cut AC, and posterior chamfer cut(s) PC.

FIGS. 17 to 45 show another example embodiment of a cutting guide system 201. FIGS. 17 to 45 shows the cutting guide system 201 attached to the distal (lower) end of a femur bone F. These figures illustrate an example use of the cutting guide system 201 to make a distal femur cut DF, anterior femur cut AF, posterior femur cut(s) PF, anterior chamfer cut AC, and posterior chamfer cut(s) PC.

Figure 17:
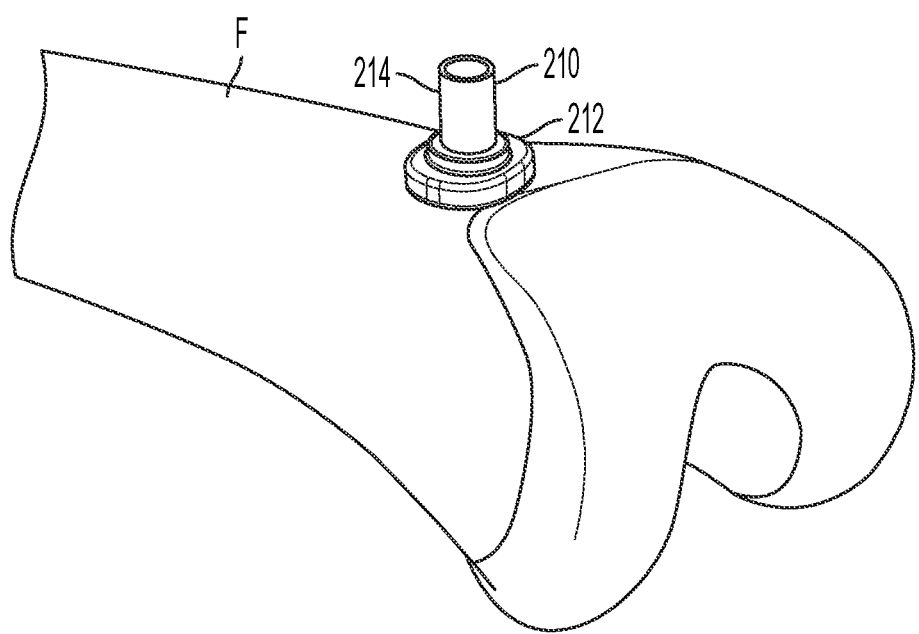
FIG. 17 shows an example of a support mount for a cutting guide system in accordance with the disclosure.
Figure 18:
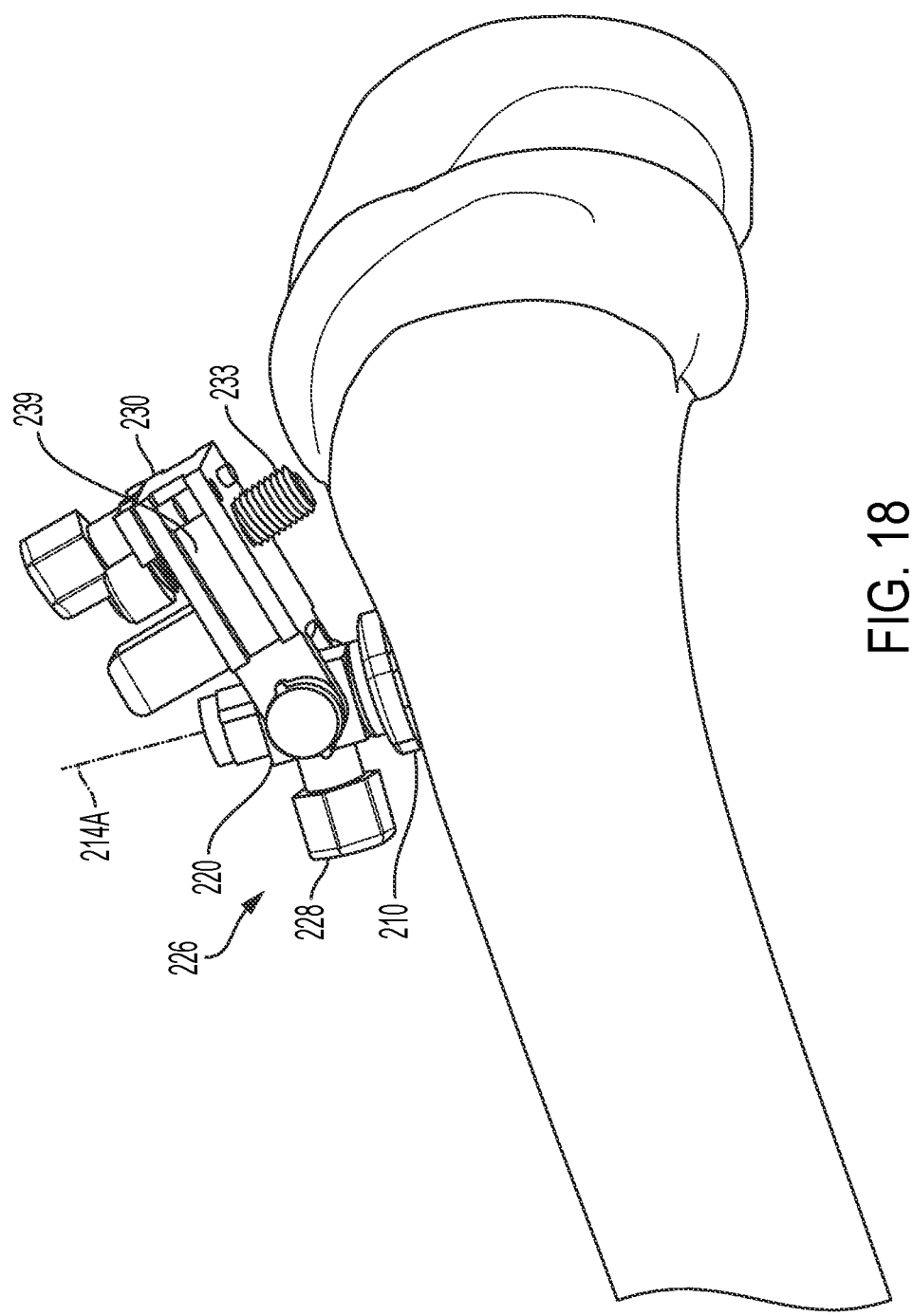
FIG. 18 shows an assembly of components of another example of a cutting guide system in accordance with the disclosure, including the support mount of FIG. 17.
Figure 24:
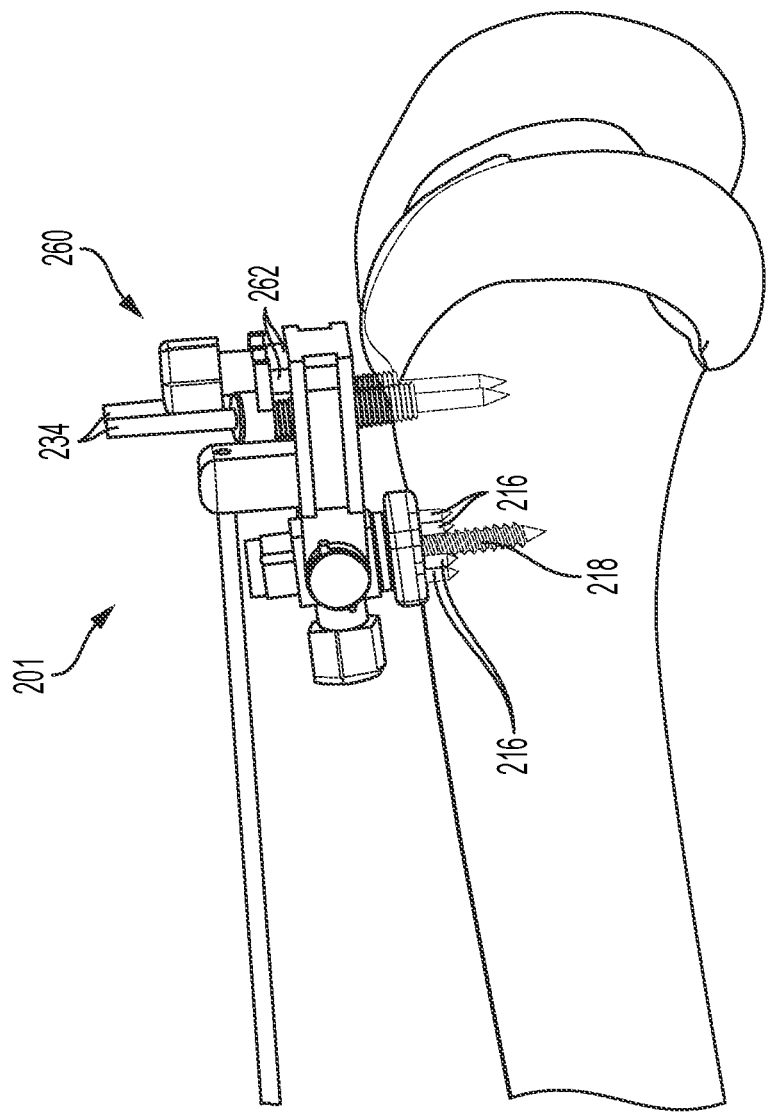
FIG. 24 shows another view of the assembly of FIG. 18 with the alignment rod attached to it.

The cutting guide system 201 includes a support mount 210 that is attachable to a bone, such as the anterior distal femur F shown in FIG. 17 or another suitable bone. The support mount 210 may be attached to the bone in a conventional manner. For example, the support mount 210 may be attached to the bone by one or more fasteners that fit through one or more holes in the support mount 210 and penetrate into the bone. The fasteners may be conventional fixation pins, trocar tipped pins, screws, and/or other fasteners. Additionally or alternatively, spikes may be located on the contacting face of the support mount 210 and may be driven into the bone to attach the support mount 210 to the bone and/or to aid in the stability and rigidity of the support mount 210 with respect to the bone. In the illustrated example, as can be seen in FIG. 24, the example support mount 210 has spikes 216 that can be driven into the bone, and a threaded fastener 218 may also be used to attach the support mount 210 to the bone. The support mount 210 is attachable in a fixed relation with respect to the bone or other object to be cut by the cutting instrument either directly or through one or more other components As shown in FIG. 17, the illustrated support mount 210 has a base 212, and a first rod 214 extends from the base 212 such that the first rod 214 extends away from the bone when the support mount 210 is attached to the bone. The spikes 216 may extend from the base 212 toward the bone. The fastener 218 may fit inside a hollow central area of the first rod 214 to extend through a hole in the base 212 to be driven into the bone.

As with the previous embodiments described herein, when the support mount 210 is attached to the bone, the specific position as far as location and rotational orientation of the support mount 210 with respect to the bone is not critical. The user can locate the support mount 210 on an area of the bone that will facilitate the stability of the support mount 210.

The support mount 210 may be attached to the bone either by itself or with one or more other components of the cutting guide system 201 attached. In one example, after the support mount 210 is attached to the bone, an assembly of the other components illustrated in FIG. 18 may be mounted on the support mount 210. Alternatively, the support mount 210 may be assembled to the other components illustrated in FIG. 18 prior to attaching the support mount 210 to the bone.

The cutting guide system 201 further comprises a first adjusting guide 220 and a second adjusting guide 230. The first adjusting guide 220 is mounted on the first rod 214 for rotation about the first rod 214 and the first rod axis 214A. The first adjusting guide 220 has an opening (recess or hole) in which the first rod 214 is positioned for relative rotational movement, allowing the first adjusting guide 220 to rotate about the first rod 214 and the first rod axis 214A. In an alternative arrangement, the first rod may be part of, or rigidly attached to, the first adjusting guide 220, and the support mount 210 may have a corresponding opening (recess or hole) for receiving the first rod. In this alternative arrangement, the first rod rotates with the first adjusting guide 220 (i.e., the first rod rotates within the opening in the support mount 210). In either arrangement, the first adjusting guide 220 is mounted for rotation with respect to the support mount 210 around the first rod axis 214A.

A second rod 224 may be a part of, or rigidly attached to, the first adjusting guide 220, extending laterally therefrom. The axis 224A of the second rod is labeled in FIG. 21. The second adjusting guide 230 is mounted on the second rod for rotation about the second rod and the second rod axis 224A. The second adjusting guide 230 has an opening (recess or hole) in which the second rod is positioned for relative rotational movement, allowing the second adjusting guide 230 to rotate about the second rod and the second rod axis 224A. In an alternative arrangement, the second rod may be part of, or rigidly attached to, the second adjusting guide 230, and the first adjusting guide 220 may have a corresponding opening (recess or hole) for receiving the second rod. In this alternative arrangement, the second rod rotates with the second adjusting guide 230 (i.e., the second rod rotates within the opening in the first adjusting guide 220). In either arrangement, the second adjusting guide 230 is mounted for rotation with respect to the first adjusting guide 220 around the second rod axis 224A.

The first rod and/or the second rod need not extend continuously through the part with which it is associated. For example, the second rod may comprise two rod portions extending from either side of the first adjusting guide 220 or one rod portion extending from one side of the first adjusting guide 220. The first rod and the corresponding opening in which it is positioned for relative rotation together form a first hinge, allowing the first adjusting guide 220 to pivot about the first axis 214A. The second rod and the corresponding opening in which it is positioned for relative rotation together form a second hinge, allowing the second adjusting guide 230 to pivot about the second axis 224A. In this example, the joint for positioning the cutting instrument comprises the first hinge and the second hinge. Thus, as examples of permitted directions of movement, the joint allows the cutting instrument support to be pivoted to the right and left, around the first axis 214A, and toward and away from the object to be cut (e.g., the bone), around the second axis 224A.

A locking mechanism 226 is associated with the first adjusting guide 220 for selectively allowing the first adjusting guide 220 to rotate about the first rod axis 214A or preventing the first adjusting guide 220 from rotating about the first rod axis 214A. In the illustrated embodiment, the locking mechanism 226 comprises a set screw 228 that can be turned to securely engage the first rod, thereby locking the first adjusting guide 220 against rotation, or turned in the opposite direction to release the first rod, thereby allowing the first adjusting guide 220 to rotate about the first rod axis 214A. Similarly, a locking mechanism 236 is associated with the second adjusting guide 230 for selectively allowing the second adjusting guide 230 to rotate about the second rod axis 224A or preventing the second adjusting guide 230 from rotating about the second rod axis 224A. In the illustrated embodiment, the locking mechanism 236 comprises a set screw 238 that can be turned to securely engage the second rod, thereby locking the second adjusting guide 230 against rotation, or turned in the opposite direction to release the second rod, thereby allowing the second adjusting guide 230 to rotate about the second rod axis 224A. Other locking (fastening, clamping, or securing) mechanisms may be used for the locking mechanisms 226 and 236.

The first adjusting guide 220 and the second adjusting guide 230 may have transducers 140 associated with them, as described above and as shown in FIG. 14B. The transducers 140 are adapted to detect an amount of rotation of the adjusting guides 220, 230 about their respective axes of rotation 214A, 224A. The transducers 140 convert the rotational movement of the adjusting guides 220, 230 into an electrical signal so that the user can get an accurate measurement of the angular positions of the adjusting guides 220, 230.

As described above, the transducer 140 includes a stator 142 and a rotor 144. The stator 142 is adapted to remain rotationally fixed while the rotor 144 is adapted to rotate with the adjusting guide 220 or 230 as the adjusting guide 220 or 230 rotates about its respective rod axis 214A or 224A. The stator 142 may be coupled to the rod. The rotor 144 may be coupled to the adjusting guide 220 or 230 so that the rotor 144 rotates with the adjusting guide 120 or 130. Other components of the transducer 140 and its operation are similar as described above with respect to cutting guide system 101.

Figure 19:
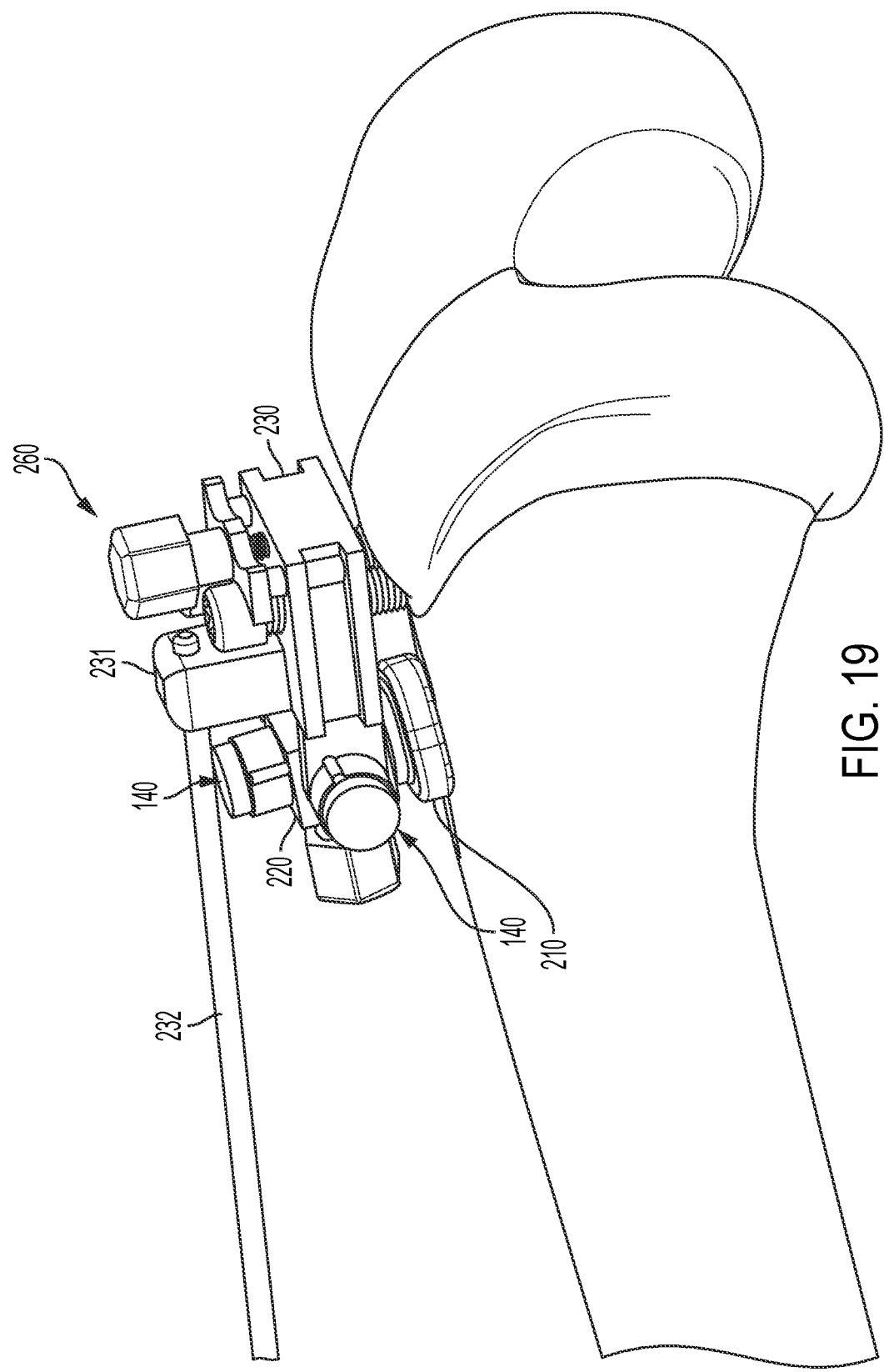
FIG. 19 shows the assembly FIG. 18 with an alignment rod attached to it.
Figure 20:
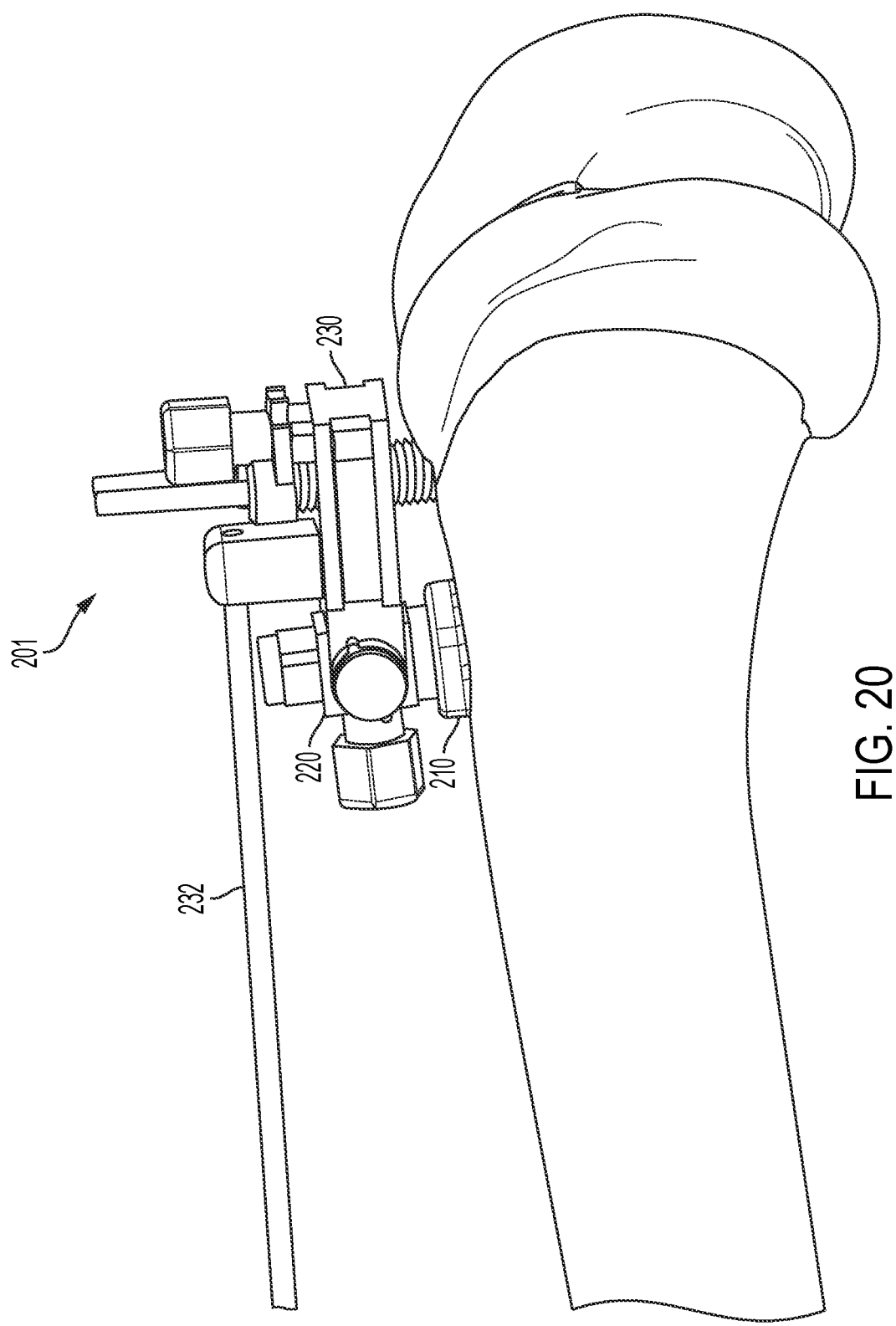
FIG. 20 shows another view of the assembly of FIG. 18 with the alignment rod attached to it.
Figure 21:
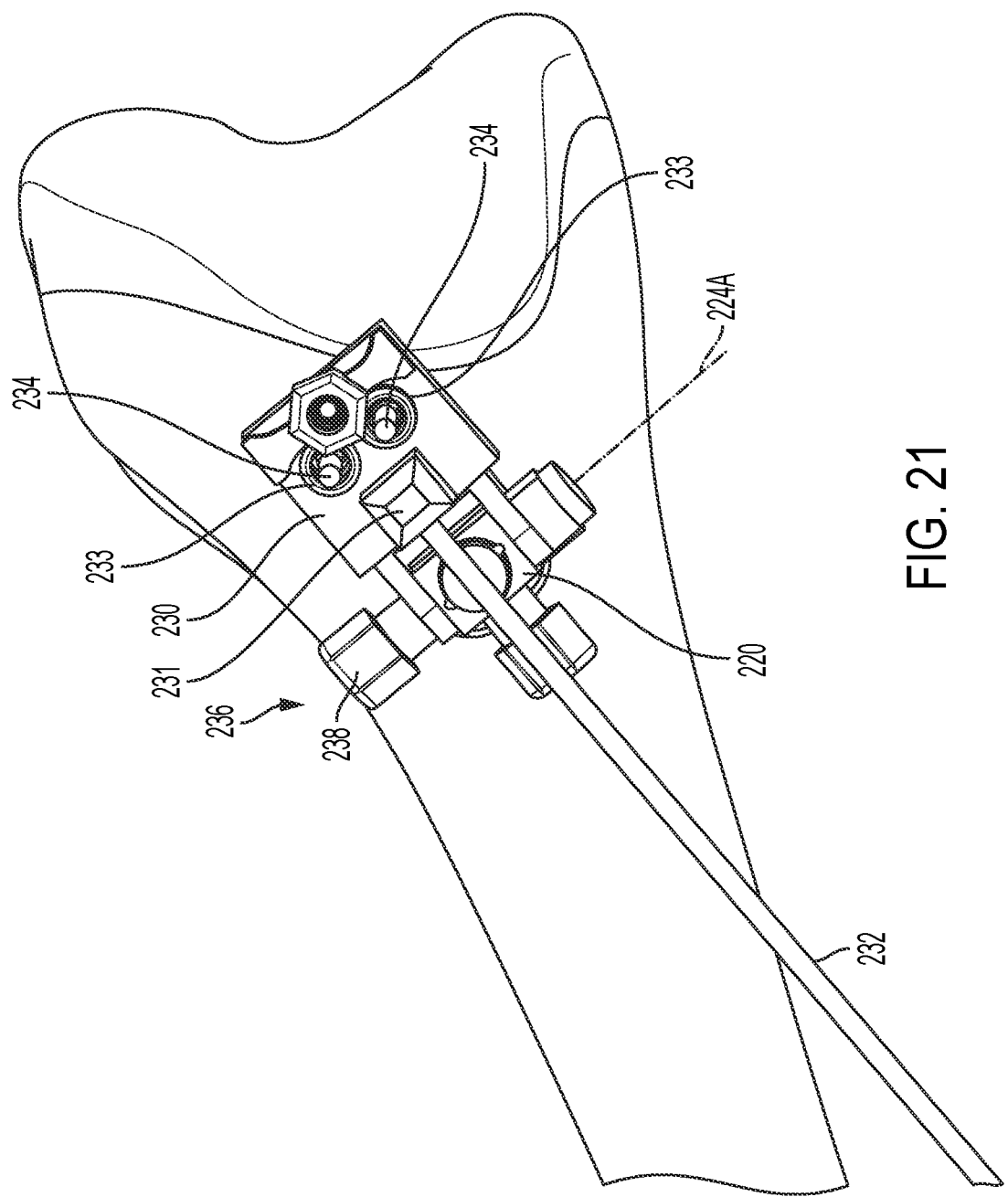
FIG. 21 shows the assembly FIG. 18 with the alignment rod attached to it, with a first adjusting guide pivoted in a first direction around a first rod axis.
Figure 22:
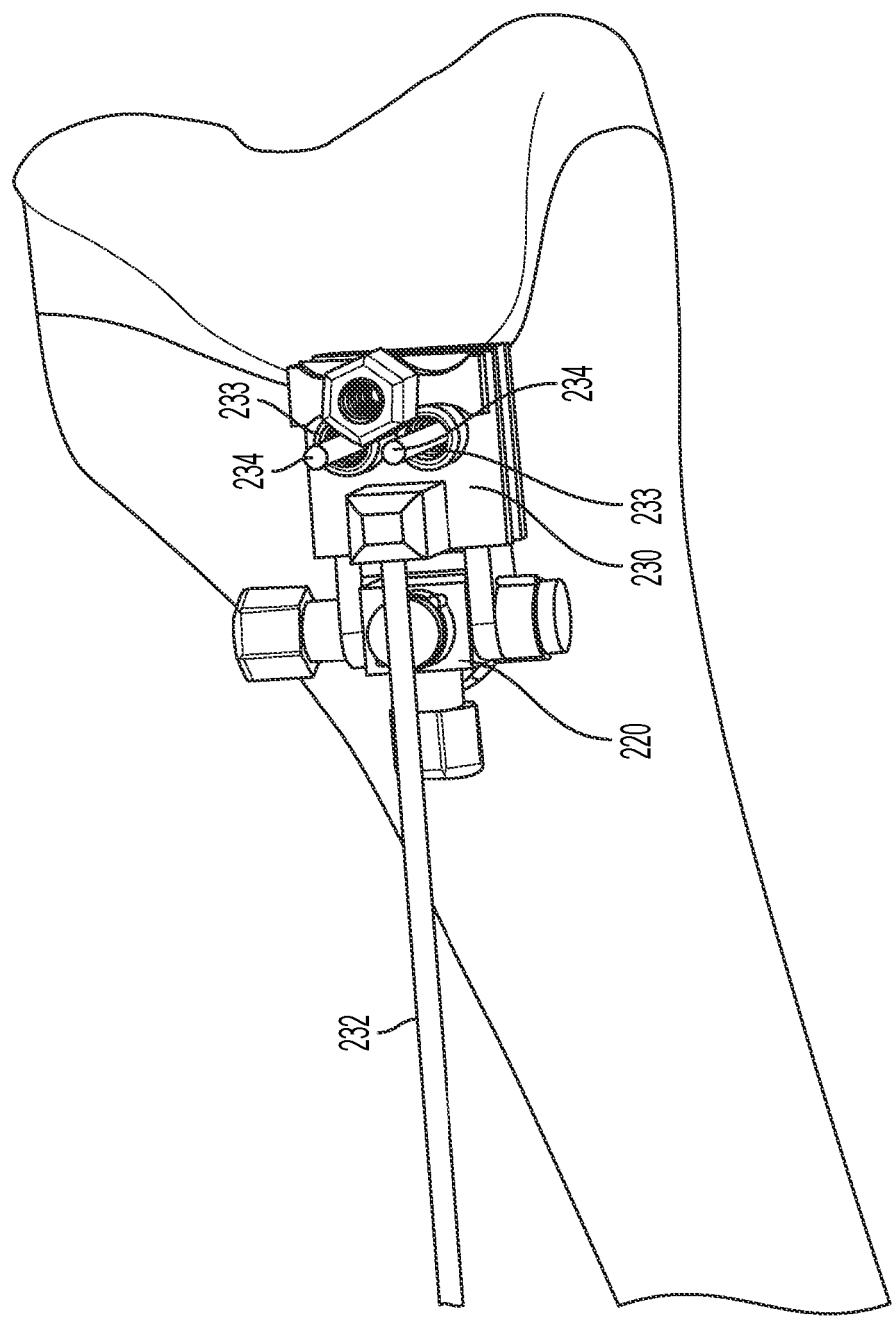
FIG. 22 shows the assembly FIG. 18 with the alignment rod attached to it, with the first adjusting guide pivoted in a second direction around the first rod axis.
Figure 23:
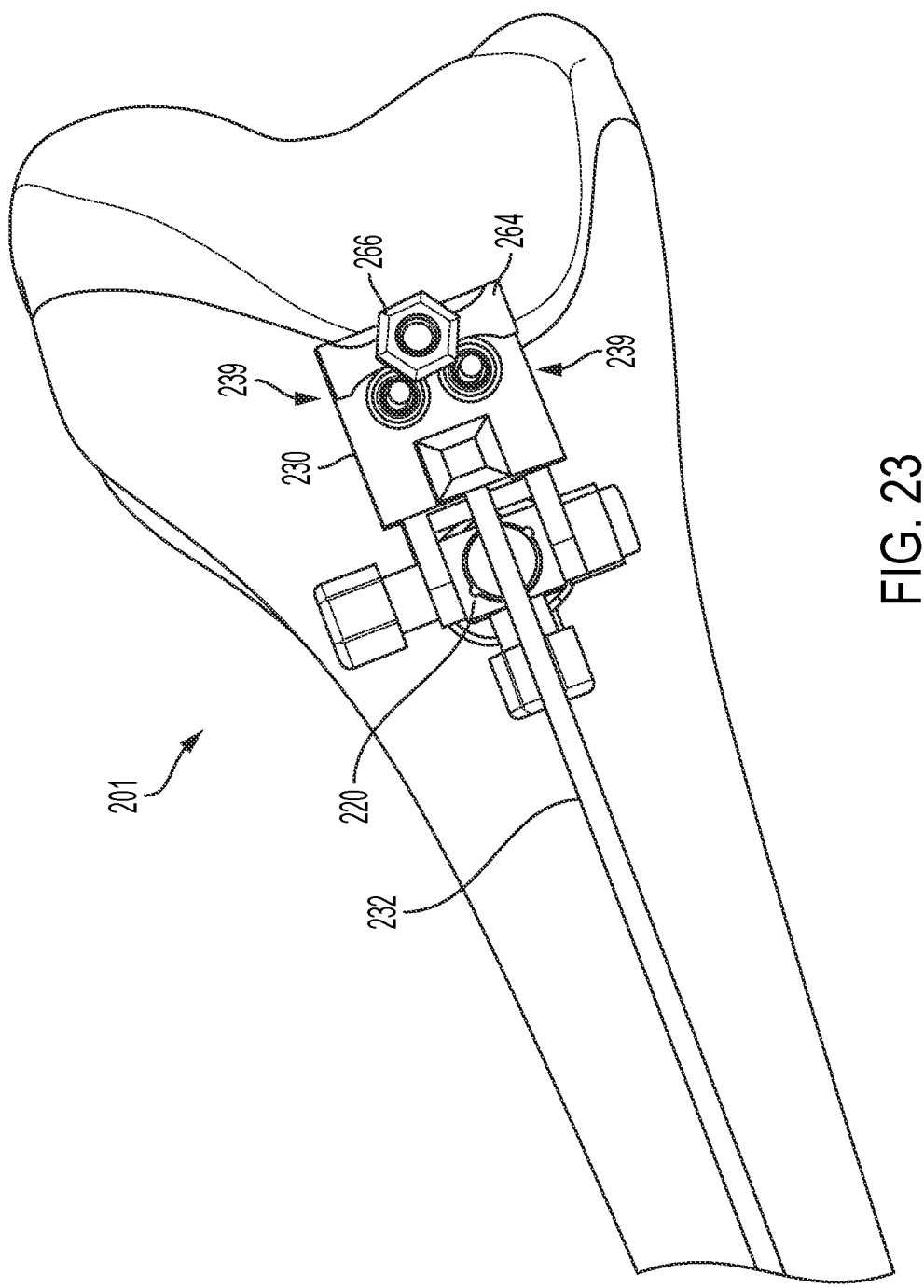
FIG. 23 shows another view of the assembly of FIG. 18 with the alignment rod attached to it.

The first adjusting guide 220 and/or the second adjusting guide 230 may have one or more features, parts, or components associated with it to assist the user with adjusting the alignment. For example, the second adjusting guide 230 may have a projection 231 extending from it for receiving an alignment rod 232. The alignment rod 232 may be connected to the projection 231 (for example, inserted into a hole in the projection 231 and retained by a friction fit or in other ways) after the components of FIG. 18 have been attached to the bone. FIG. 19 shows the assembly of FIG. 18 with the alignment rod 232 attached to it. Similarly, the first adjusting guide 220 may have one or more holes for receiving one or more alignment rods. The alignment rod(s) (e.g., the alignment rod 232 and/or other alignment rods connected to the first adjusting guide 220 and/or the second adjusting guide 230) allows the user to visualize the positioning better, to assist with aligning the cutting guide system 201.

One or more threaded adjustment screws 233 may extend through threaded holes in the second adjusting guide 230 to assist with its positioning and/or with maintaining its position. The threaded adjustment screws 233 can be rotated so that their distal ends contact the bone. After the distal end of a threaded adjustment screw 233 is in contact with the bone, rotating it further will cause the second adjusting guide 230 to rotate away from the bone, thereby allowing fine positioning adjustment.

Each of the threaded adjustment screws 233 can be cannulated, i.e., can have a hollow bore, allowing a fastener (e.g., pin such as a trocar tipped pin) 234 to extend through the adjustment screw 233. Once the user has the cutting guide system 201 in the desired position, the fastener(s) 234 can be advanced into the bone to keep the cutting guide system 201 in position, as shown in FIG. 24.

The second adjusting guide 230 has one or more recesses 239 for receiving a corresponding arm 256 of a saw mount 250. The saw mount 250 includes an adjustment base 255 that has one or more arms 256 for mating with the recess(es) 239. The saw mount 250 may further include a stem 251 that is connected to or integral with the adjustment base 255. In the illustrated example, the stem 251 extends from the top of the adjustment base 255.

Figure 25:
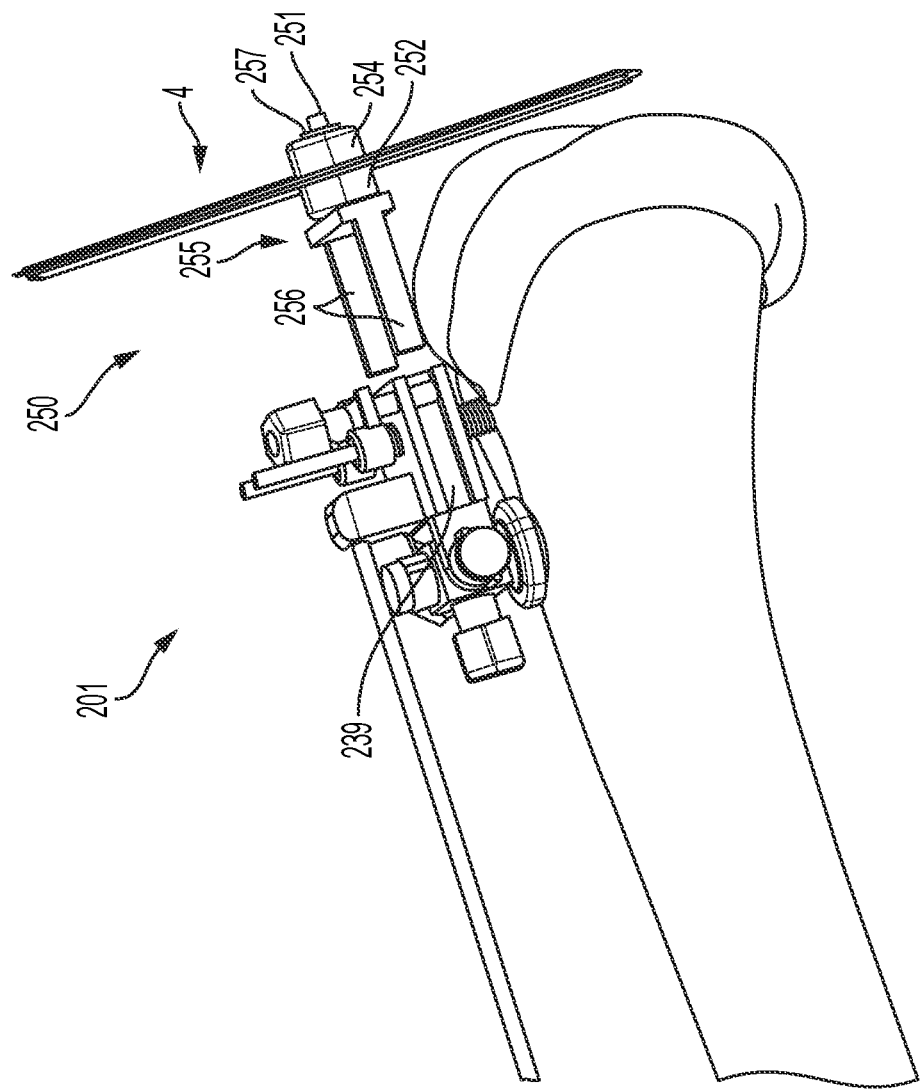
FIG. 25 shows an example of a cutting guide system in accordance with the disclosure, showing a saw mount being connected with the assembly of components of FIG. 18.
Figure 26:
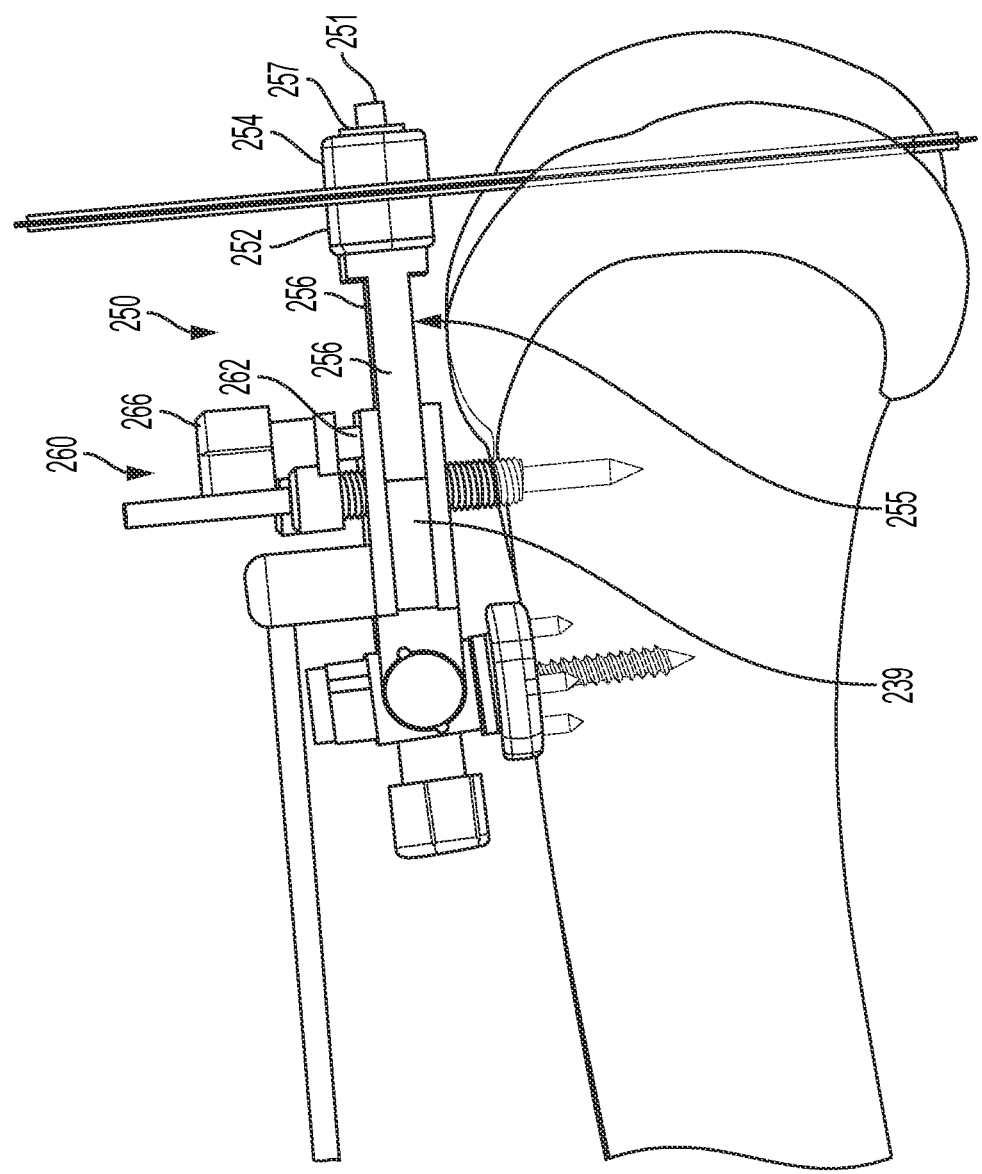
FIG. 26 shows the cutting guide system of FIG. 25, showing another stage in the connection of the saw mount to the assembly of components of FIG. 18.

In the illustrated embodiment, the adjustment base 255 has two arms 256, one on each side of the adjustment base 255. The second adjustment guide 230 has two recesses 239 sized and positioned to receive the arms 256. To connect the saw mount 250 to the assembly of FIG. 24, the user positions the arms 256 relative to the recesses 239 and slides the arms 256 into the recesses 239, as shown in FIGS. 25 and 26.

The user can adjust how far the arms 256 extend into the recesses 239 in order to position the saw mount 250 to the desired height relative to the bone. Once the saw mount 250 is at the desired height, the user can lock the position of the saw mount 250 using a locking mechanism 260. In the illustrated embodiment, the locking mechanism 260 is a clamp. The clamp comprises a pin 262 for each arm 256. The pins 262 are integral with or connected to a bar 264. A knob 266 is connected to or abuts the bar 264. The knob 266 turns a first threaded element (not shown) that is threadedly engaged with a second threaded element (not shown) that is attached to or integral with the second adjusting guide 230. In one version, the knob 266 turns an externally threaded element that engages with an internally threaded element that is integral with or connected to the second adjusting guide 230. In an alternative version, the knob 266 turns an internally threaded element that engages with an externally threaded element that is integral with or connected to the second adjusting guide 230. Turning the knob 266 causes the bar 264 and the pins 262 to move forward or backward, depending on the direction of turning the knob 266. When the arms 256 are in the recesses 239, the knob 266 can be turned to press the pins 262 against the arms 256 to lock the saw mount 250 in place. Turning the knob 266 in the other direction releases the pins 262 from engagement with the arms 256, allowing the position of the saw mount 250 to be adjusted or for the saw mount 250 to be removed. Other locking (fastening, clamping, or securing) mechanisms may be used for the locking mechanism 260.

The cutting guide system 201 further comprises a lower saw clamp 252 and an upper saw clamp 254 for securing opposite sides of a saw 4. In this example, the saw mount 250 (either alone or in conjunction with the lower saw clamp 252 and upper saw clamp 254) forms a cutting instrument support for supporting the saw 4 or other cutting instrument. The stem 251 may extend through a slot 4E in the cutting instrument (e.g., saw 4), such that the cutting instrument is pivotable with respect to the stem 251, and such that the cutting instrument may be movable back and forth in a longitudinal direction with respect to the stem 251. The saw clamps 252, 254 have through-holes for accommodating the stem 251 so that the stem 251 extends through the through-holes of both saw clamps 252, 254. The positioning of the saw clamps 252, 254 along the longitudinal length of the stem 251 may be fixed or adjustable. For example, the saw clamps 252, 254 may be sized so that, with the saw 4 in position, they fit between the adjustment base 255 and an upper nut 257 on the stem 251, preventing movement of the saw clamps 252, 254 along the longitudinal length of the stem.

When assembled, the lower saw clamp 252 and the upper saw clamp 254 are secured on opposite sides of the saw 4, with the stem 251 extending through the slot 4E in the saw bar 4A. In this embodiment, the saw 4 is a chain saw assembly comprising a saw bar 4A, a chain, and a drive cog assembly. The illustrated chain saw assembly may be attached to and driven by a handpiece (not shown). While a chain saw is illustrated, other types of saws may be secured by the cutting guide system 201.

The saw clamp 252 and/or the saw clamp 254 may have a ridge on its side that faces the saw, wherein the ridge fits within the slot 4E of the saw bar. The ridge or ridges help guide the longitudinal movement of the saw.

Figure 27:
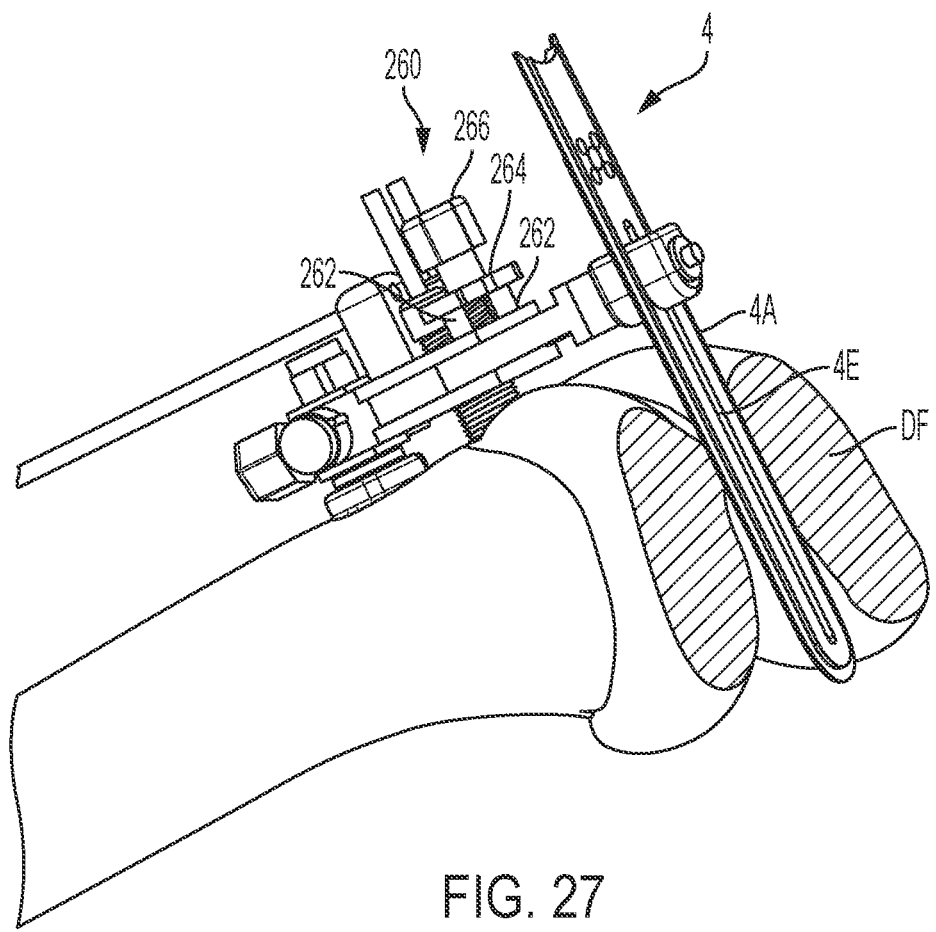
FIG. 27 shows the cutting guide system of FIG. 25, securing a saw for making a distal femur cut.
Figure 28:
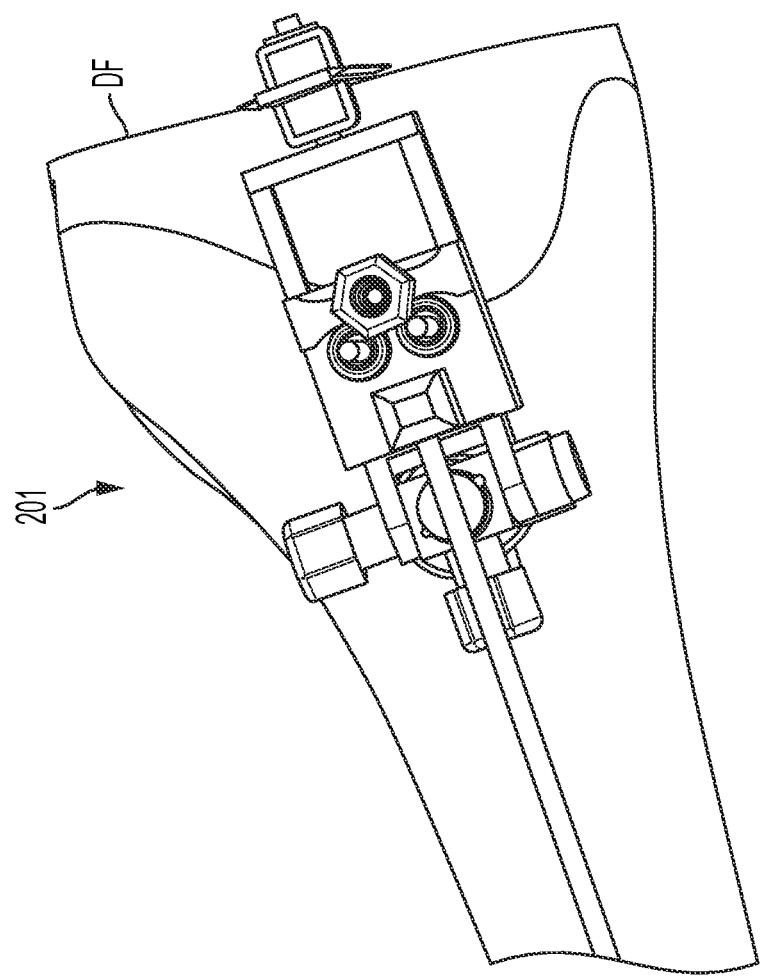
FIG. 28 shows another view of the cutting guide system of FIG. 25, securing a saw being used to make a distal femur cut.

The securement of the saw between the saw clamps 252, 254 prevents the saw from moving up or down the stem 251, while still allowing the saw bar 4A to move in a direction parallel to the length of the saw bar slot 4E, by advancing forward or pulling back. In the example of FIGS. 26-28, advancing the saw bar 4A forward with respect to the support mount 210 comprises moving the saw bar 4A posteriorly, while pulling the saw bar 4A back comprises moving the saw bar 4A anteriorly.

In some embodiments, the saw clamps 252, 254 may be rotatable around the stem 251. In this arrangement, the saw can rotate in a plane about the stem 251, wherein the axis of the stem 251 is the axis of rotation. This allows the user to move the saw not only in the forward and back direction but also rotationally in a plane about the axis of the stem 251.

When assembling the saw mount 250 to the assembly of FIG. 24, it may be advantageous that, instead of the saw 4, the saw mount 250 may first carry a stylus (not shown) that can be used to measure the desired cutting height. For example, the stem 251 can carry a stylus between the adjustment base 255 and the upper nut 257 on the stem 251, preventing movement of the stylus along the longitudinal length of the stem 251. The saw clamps 252, 254 may optionally be used to secure the stylus. Using the stylus, the user can determine the desired height of the cut, to be used in positioning the saw. The arms 256 and the second adjusting guide 230 may have indicia to indicate the height measured by the stylus. Then, the stylus can be removed and replaced by the saw 4 and optionally the saw clamps 252, 254. Using the measured height, e.g., as indicated by the indicia, the user can position the saw mount 250 to the desired height for the cut.

FIGS. 27 and 28 illustrate use of the saw 4 to make a distal femur cut DF. The position of the saw 4 is determined by the positioning and locking of the first adjusting guide 220, the second adjusting guide 230, and the saw mount 250, as described above.

Figure 29:
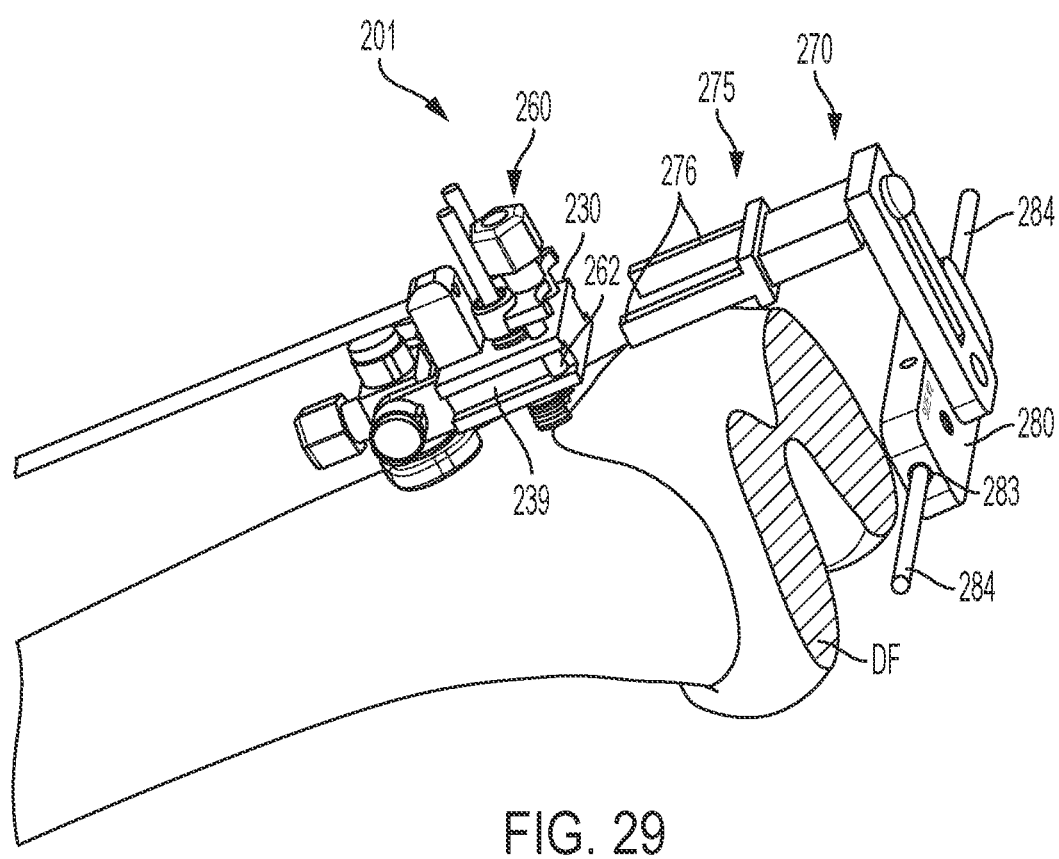
FIG. 29 shows the cutting guide system of FIG. 25, showing a guide mount being connected with the assembly of components of FIG. 18, in order to position a cut mount block.

After the distal femur cut DF has been made, the saw mount 250 and saw 4 may be removed. Then, as illustrated in FIG. 29, a guide mount 270 may be connected to the assembly of FIG. 24, in order to position a cut mount block 280. The size of the cut mount block 280 may be selected based on the size of the implant (e.g., Size #2, as indicated in the illustrations).

Figure 30:
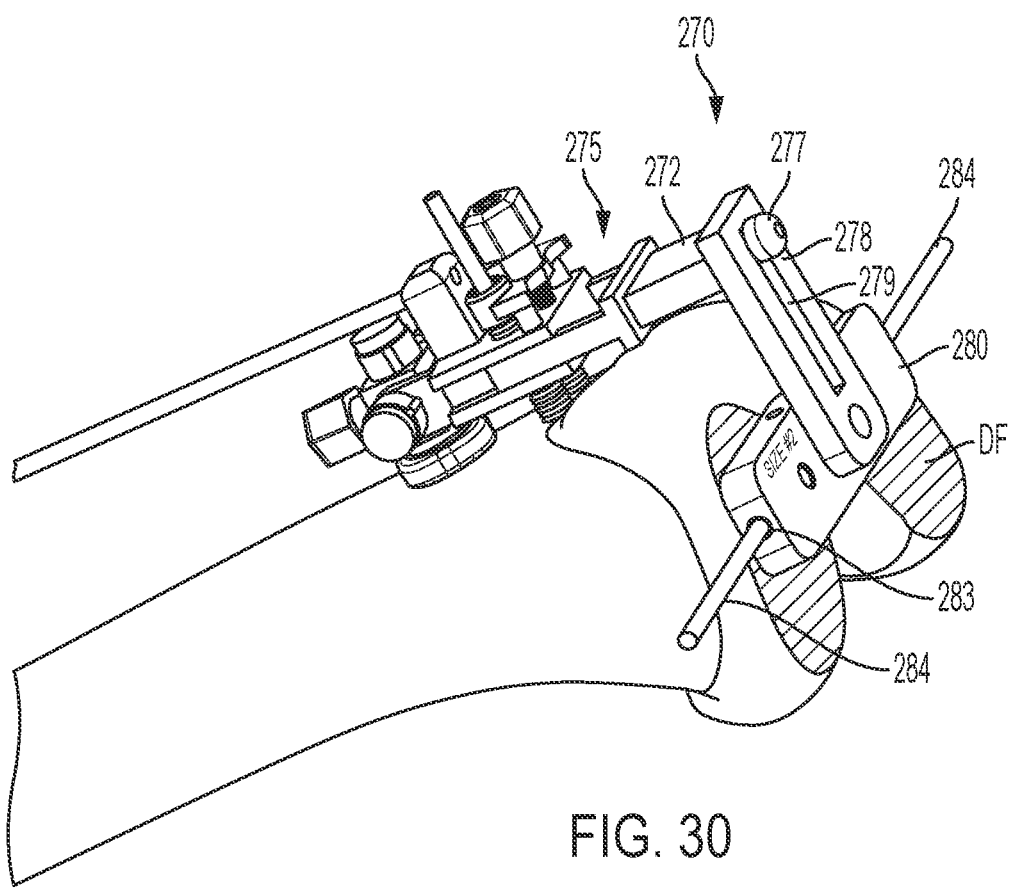
FIG. 30 shows the cutting guide system of FIG. 25, showing another stage in the connection of the guide mount to the assembly of components of FIG. 18, in order to position the cut mount block.

The guide mount 270 connects to the assembly of FIG. 24 in a similar manner as the saw mount 250. In the illustrated embodiment, the guide mount 270 has a guide mount adjustment base 275 with two arms 276, one on each side of the guide mount adjustment base 275. The arms 276 are sized and positioned like the arms 256, to be received by the recesses 239 of the second adjustment guide 230. To connect the guide mount 270 to the assembly of FIG. 24, the user positions the arms 276 relative to the recesses 239 and slides the arms 276 into the recesses 239, as shown in FIGS. 29 and 30.

The user can adjust how far the arms 276 extend into the recesses 239, similar to the positioning of the saw mount 250, as described above. Once the guide mount 270 is at the desired height, the user can lock the position of the saw mount 250 using the locking mechanism 260. That is, the arms 276 can be locked by the locking mechanism 260 in the same manner as described above with respect to the arms 256.

The guide mount 270 further includes a body 272 connected to or integral with the guide mount adjusting base 275 as well as a stem 271 extending from the body 272 and an upper nut 277 that threadedly engages the stem 271. The guide mount 270 further comprises an adjusting bar 278 with a slot 279 in it. When assembled, the stem 271 extends through the slot 279. The nut 277 can be loosened to allow the adjusting bar 278 to be moved forward or backward, as well as in some embodiments to pivot about the stem 271. The nut 277 can be tightened to lock the position of the adjusting bar 278.

The guide mount 270 carries the cut mount block 280. In the illustrated embodiment, the cut mount block 280 is releasably attached to the adjusting bar 278, for example by a fastener threadedly engaged with a threaded hole 282 in the cut mount block 280. Optionally, alignment rods 284 may be used to help align the cut mount block 280. The alignment rods 284 may engage by a friction or other fit with holes 283 in the cut mount block 280.

Figure 31:
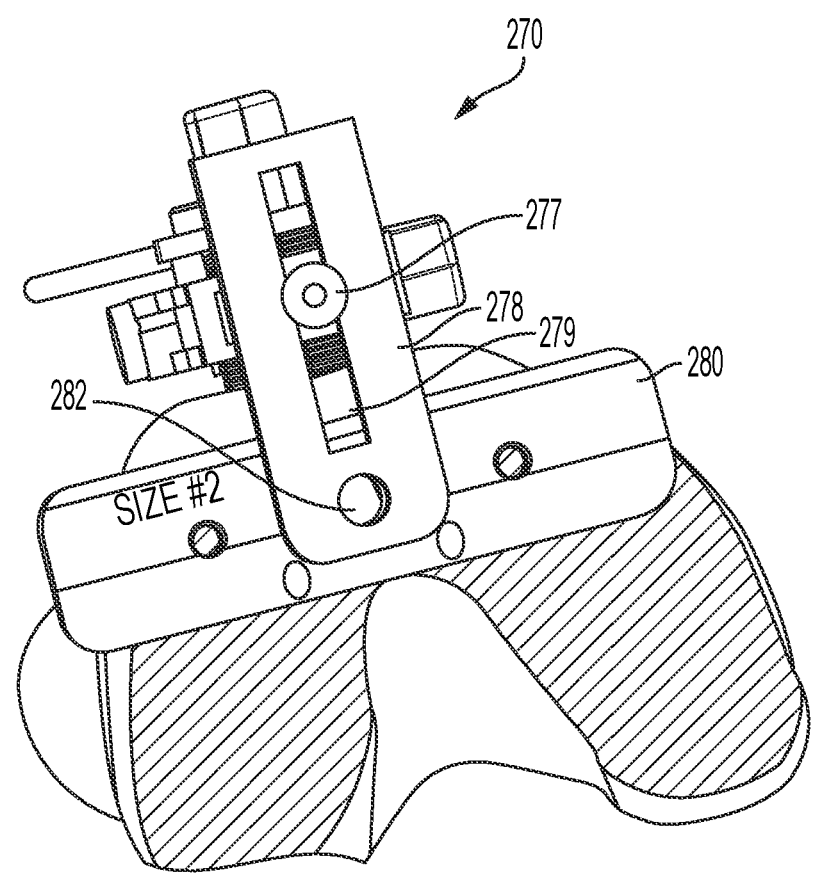
FIG. 31 shows the cutting guide system of FIG. 25, showing a mechanism for adjusting the forward-backward (anterior-posterior) position of the cut mount block.
Figure 32:
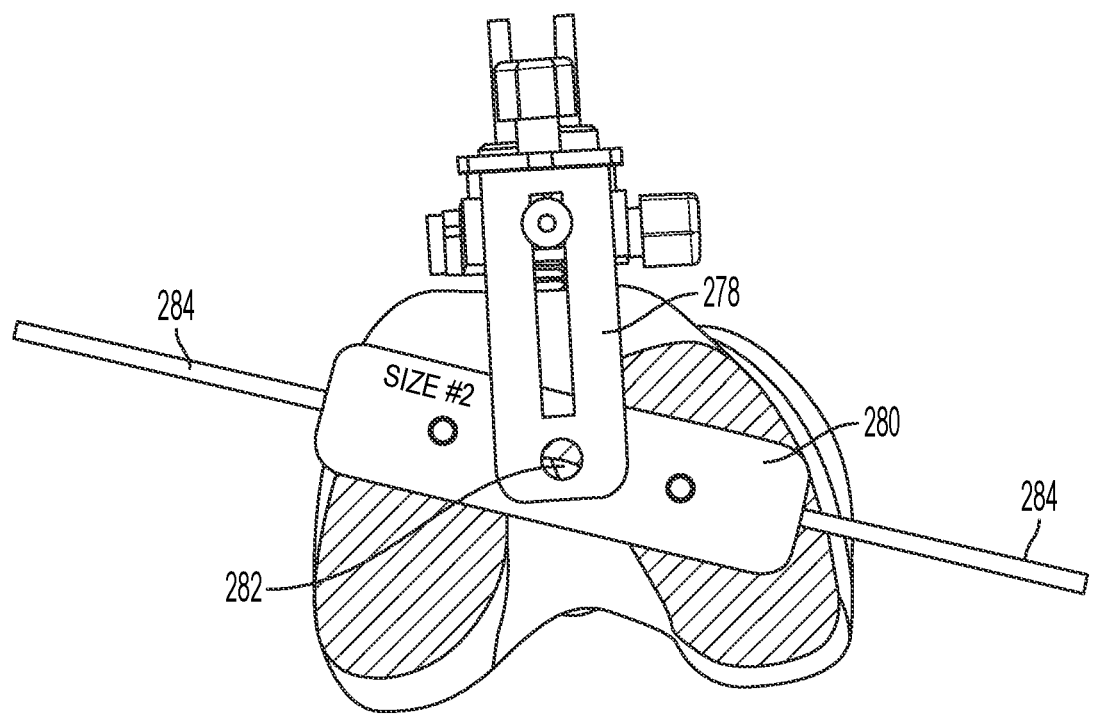
FIG. 32 shows the cutting guide system of FIG. 25, showing an angular position of the cut mount block being adjusted in a first direction.
Figure 33:
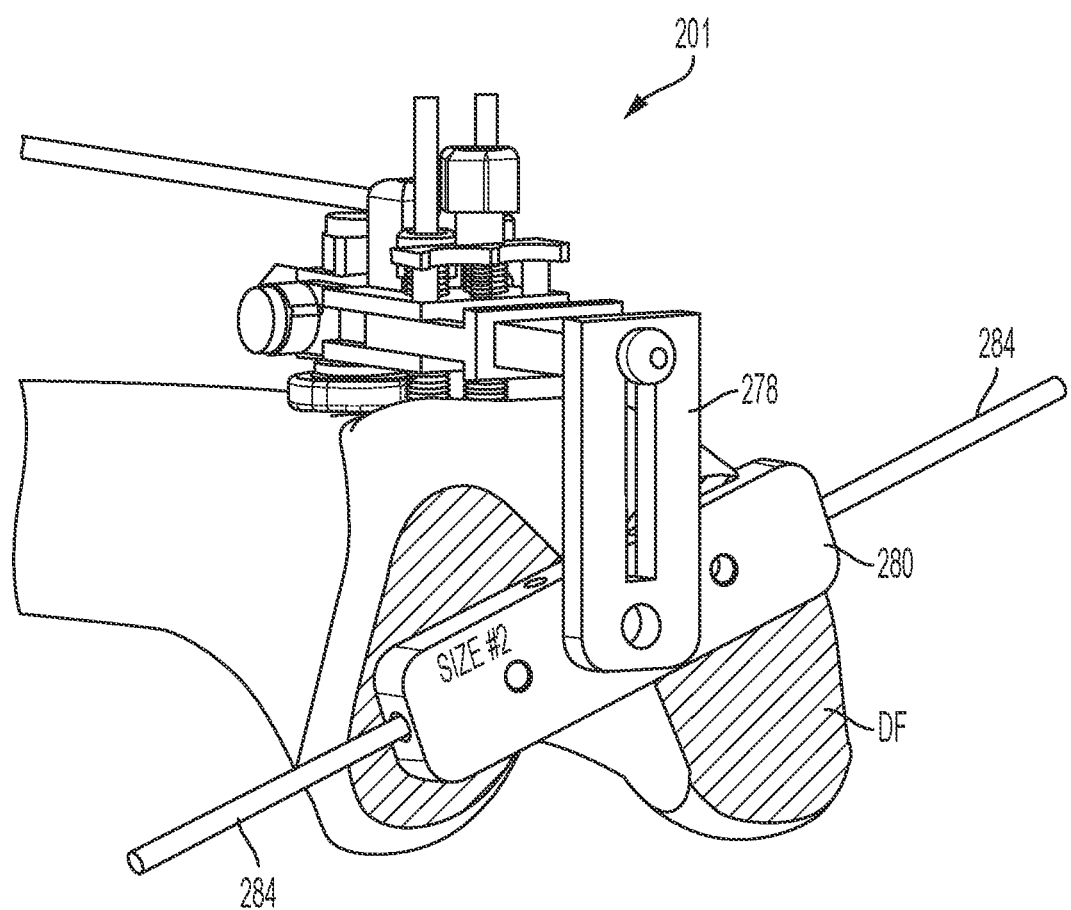
FIG. 33 shows the cutting guide system of FIG. 25, showing an angular position of the cut mount block being adjusted in a second direction.

The user can adjust the positioning of the cut mount block 280 to its desired position. The height of the cut mount block 280 can be adjusted by the amount the arms 276 extend into the recesses 239, locked in place by the locking mechanism 260. In some embodiments, it is desirable to adjust the height so that a planar surface on the bottom of the cut mount block 280 abuts and is flush against the planar surface of the distal femur cut DF. The forward-backward (anterior-posterior) position of the cut mount block 280 can be adjusted by loosening the upper nut 277 and adjusting the position of the adjusting bar 278, as shown in FIG. 31. The position of the adjusting bar 278 can be locked by tightening the upper nut 277. The angular position of the cut mount block 280 can be adjusted by rotating it about an axis of its connection with the adjusting bar 278, as shown in FIGS. 32 and 33. If at any point the user wants to use a different size cut mount block 280, the user can make the desired substitution.

Figure 34:
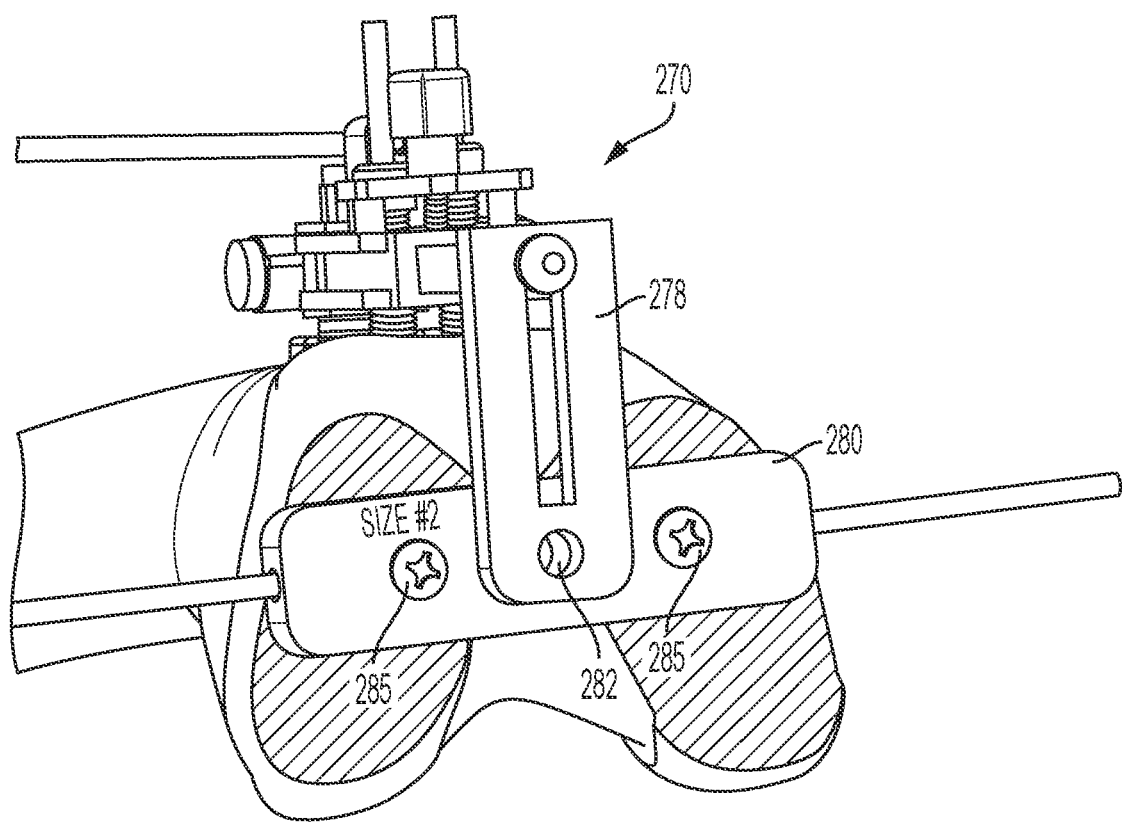
FIG. 34 shows another view of the cutting guide system of FIG. 25, showing a position of the cut mount block.
Figure 35:
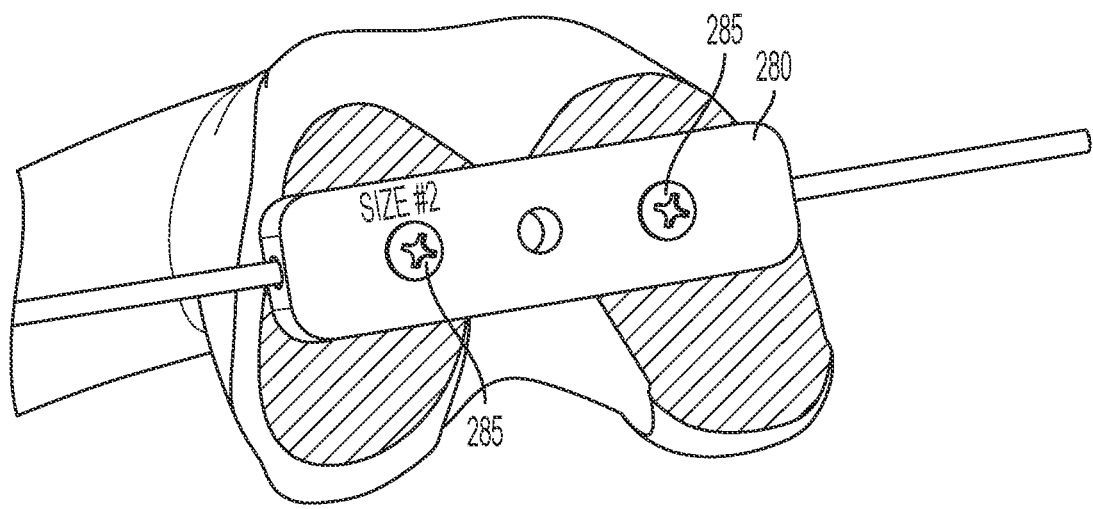
FIG. 35 shows the cut mount block of FIGS. 29-34 attached to a bone.

Once the cut mount block 280 is in the desired position, it can be attached to the bone, for example by one or more fasteners 285, as shown in FIG. 34. Then, the guide mount 270 can be removed from the cut mount block 280, for example by releasing the fastener (not shown) that had been engaged with the threaded hole 282 in the cut mount block 280. The assembly of FIG. 24 can also be removed, leaving only the attached cut mount block 280 (and any fastener(s) for it), as shown in FIG. 35.

Figure 36:
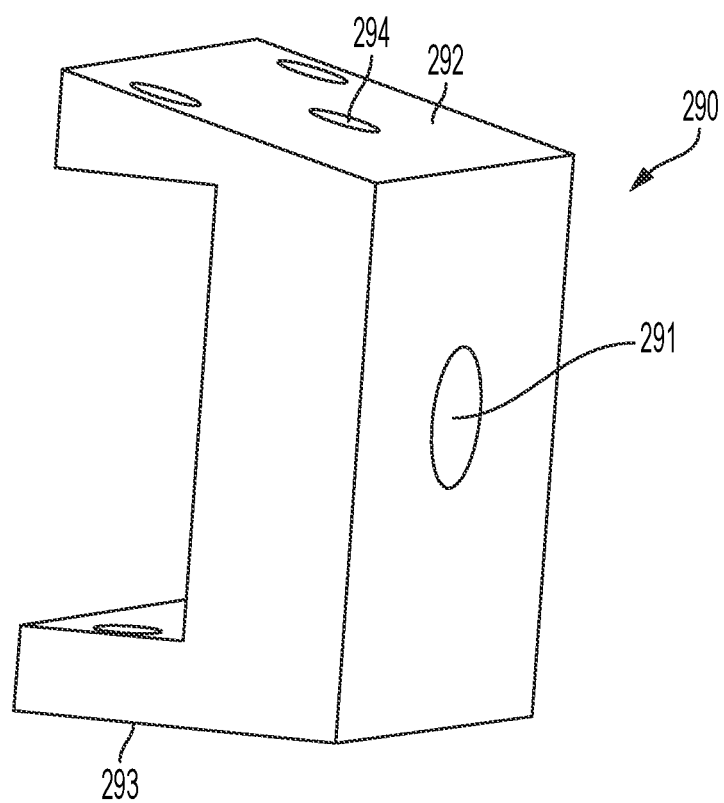
FIG. 36 shows a first adapter configured to connect to the cut mount block of FIGS. 29-35.
Figure 37:
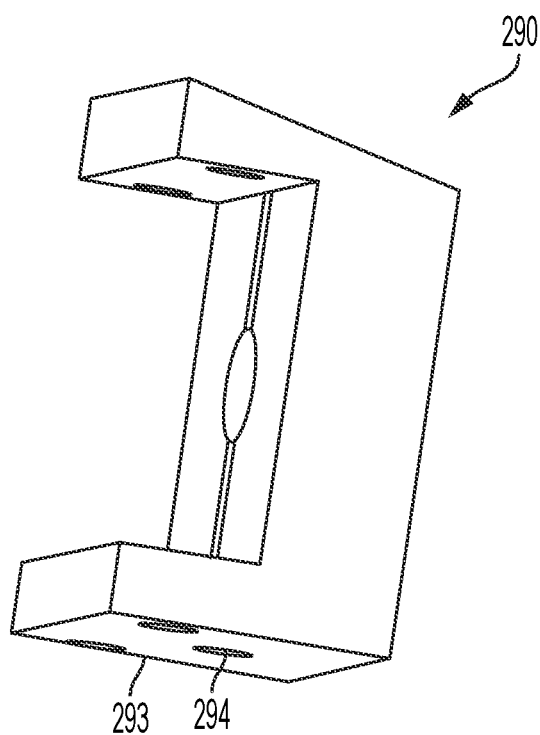
FIG. 37 shows another view of the first adapter of FIG. 36.
Figure 38:
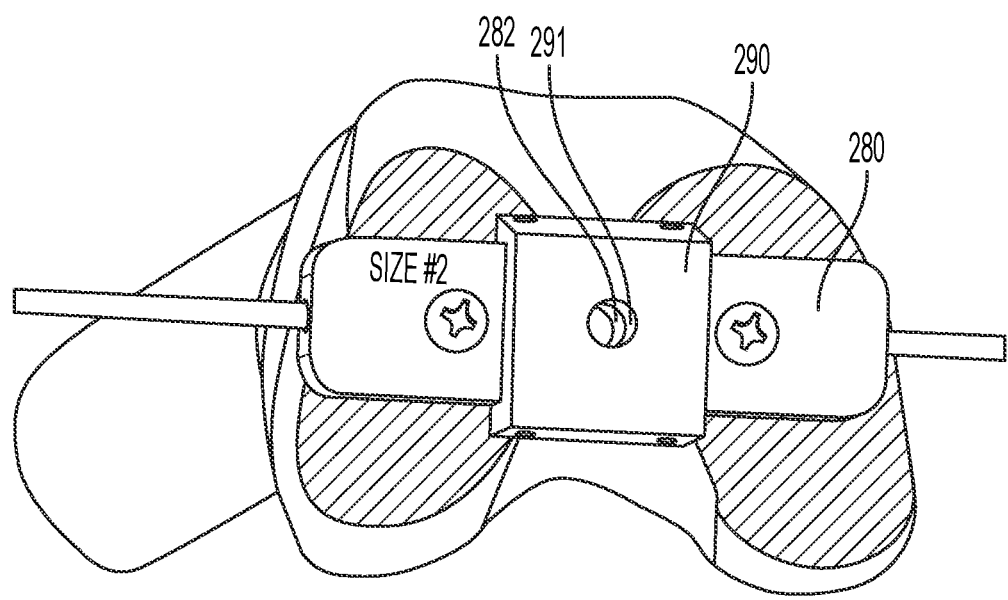
FIG. 38 shows the first adapter of FIG. 36 positioned over the cut mount block of FIGS. 29-35.

A first adapter 290, as shown in FIGS. 36 and 37, is sized and shaped to connect to the cut mount block 280 for positioning a saw 4 for making the anterior femur cut AF and/or the posterior femur cut(s) PF. The underside of the adapter 290 may be shaped to fit over the cut mount block 280. The adapter 290 may be connected to the cut mount block 280 by a fastener by way of the hole 291 in the adapter 290 and the hole 282 in the cut mount block 280. FIG. 38 shows the first adapter 290 positioned over the cut mount block 280.

Figure 39:
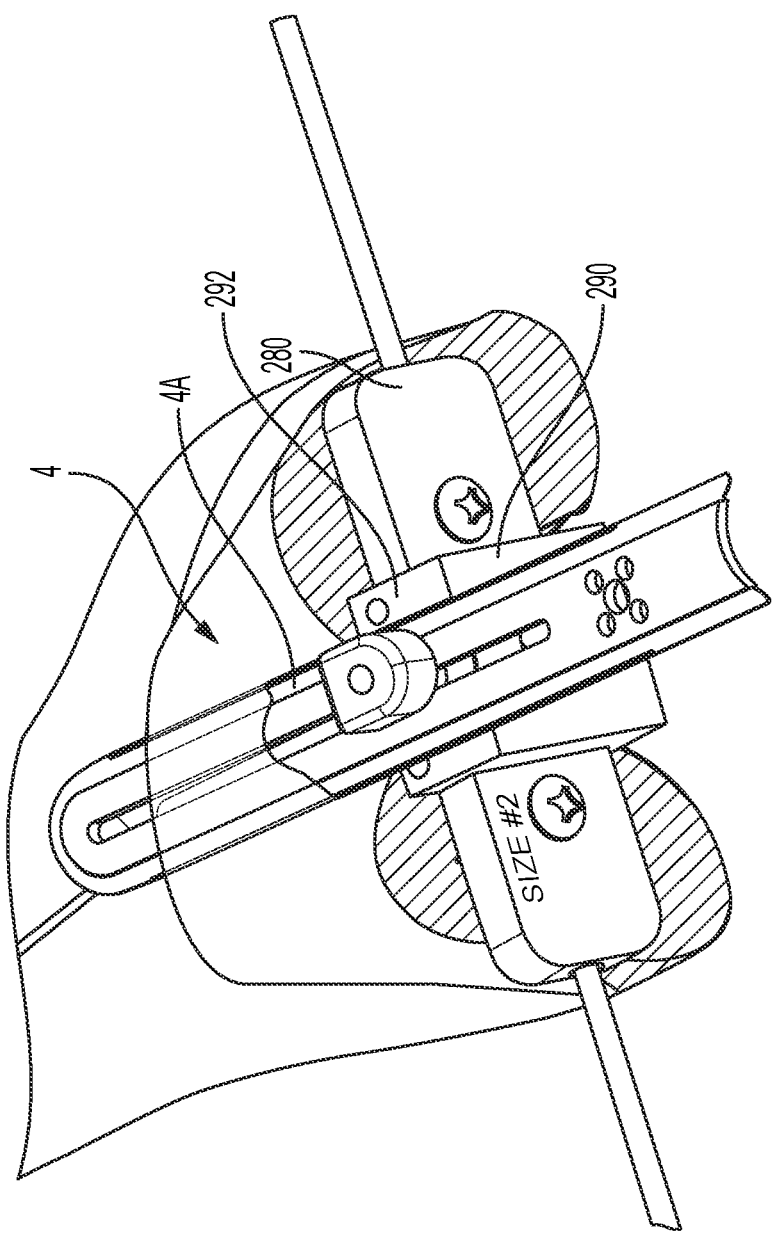
FIG. 39 shows a saw attached to an anterior surface of the first adapter of FIG. 36, while the first adapter of FIG. 36 is positioned over the cut mount block of FIGS. 29-35, securing the saw for making an anterior femur cut.
Figure 40:
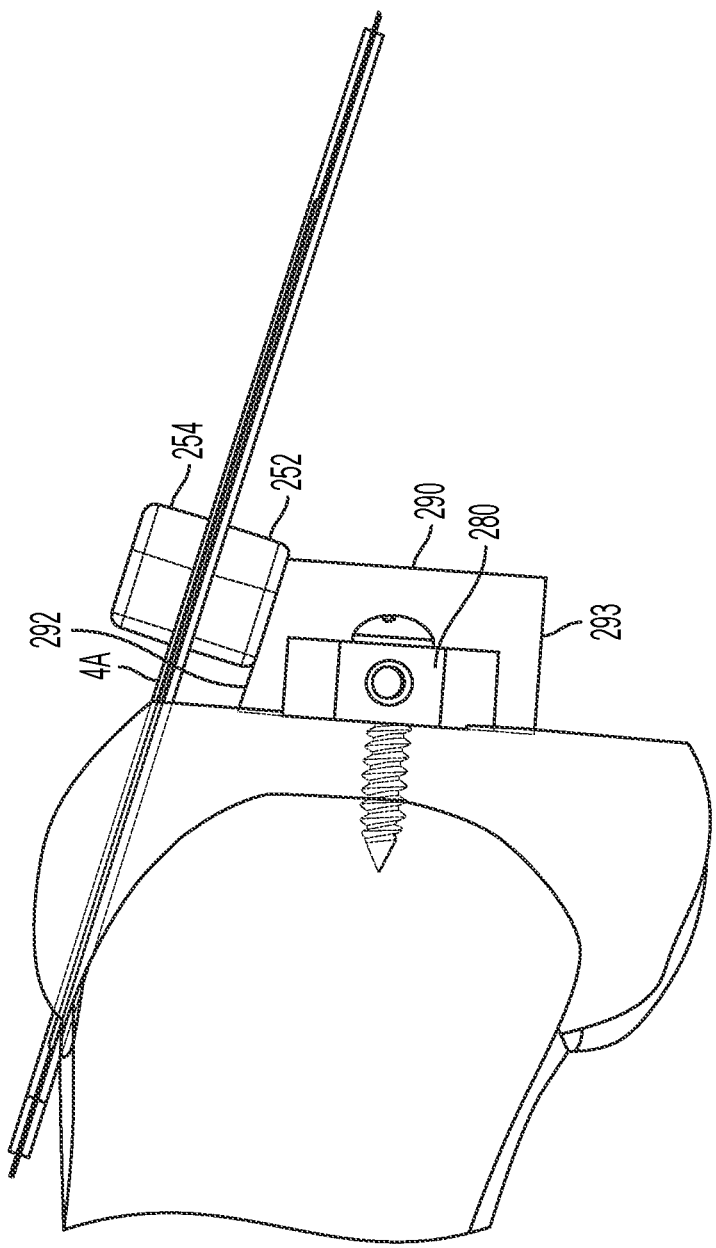
FIG. 40 shows another view of the saw attached to an anterior surface of the first adapter of FIG. 36, while the first adapter of FIG. 36 is positioned over the cut mount block of FIGS. 29-35, securing the saw for making an anterior femur cut.

Once the first adapter 290 is in place, a saw 4 may be attached to it. For example, FIG. 39 shows a saw 4 attached to an anterior surface 292 of the first adapter 290. The anterior surface 292 may be shaped, e.g., sloped, to position the saw 4 for making the anterior femur cut AF. The anterior surface 292 may have a hole 294 for receiving a stem on which a lower saw clamp 252 and upper saw clamp 254 can be mounted, with the saw bar 4A between them, in a manner similar to that described above. In an alternative arrangement, the stem is integral with the first adapter 290, extending from the anterior surface 292 at the location of the hole 294. The mounting of the saw bar 4A on the stem allows the saw bar 4A to be advanced forward, to be retracted, and to pivot around the stem, in a manner similar to that described above. Once positioned on the anterior surface 292, the saw 4 can be used to make the anterior femur cut AF, as shown in FIGS. 39 and 40.

Figure 41:
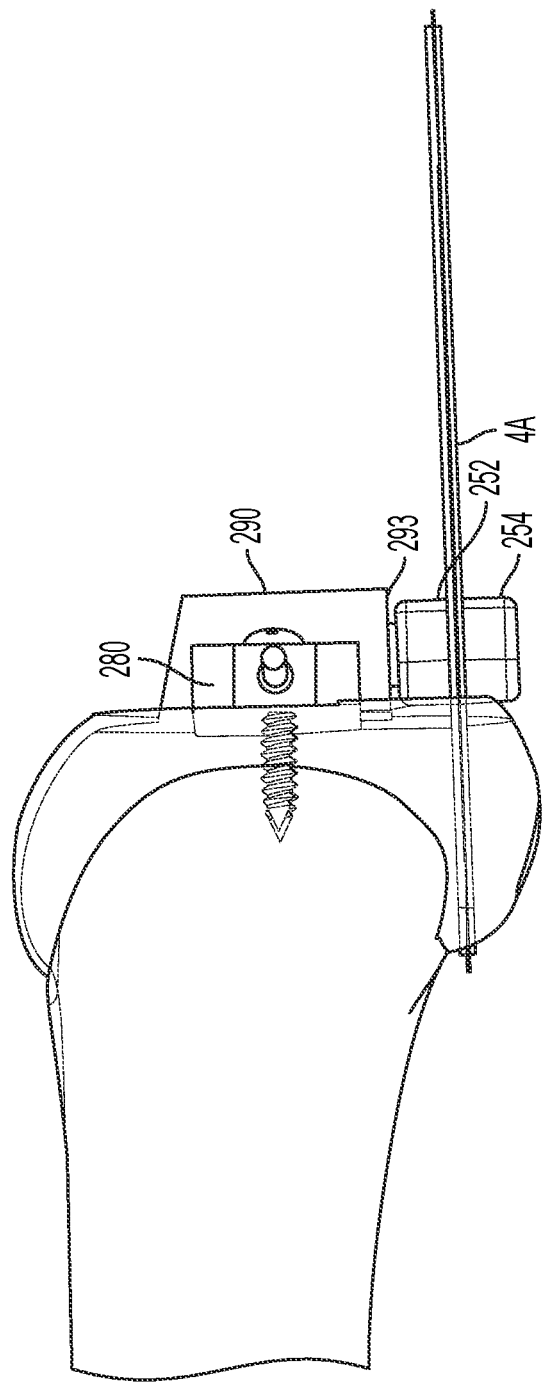
FIG. 41 shows a saw attached to a posterior surface of the first adapter of FIG. 36, while the first adapter of FIG. 36 is positioned over the cut mount block of FIGS. 29-35, securing the saw for making a posterior femur cut.
Figure 42:
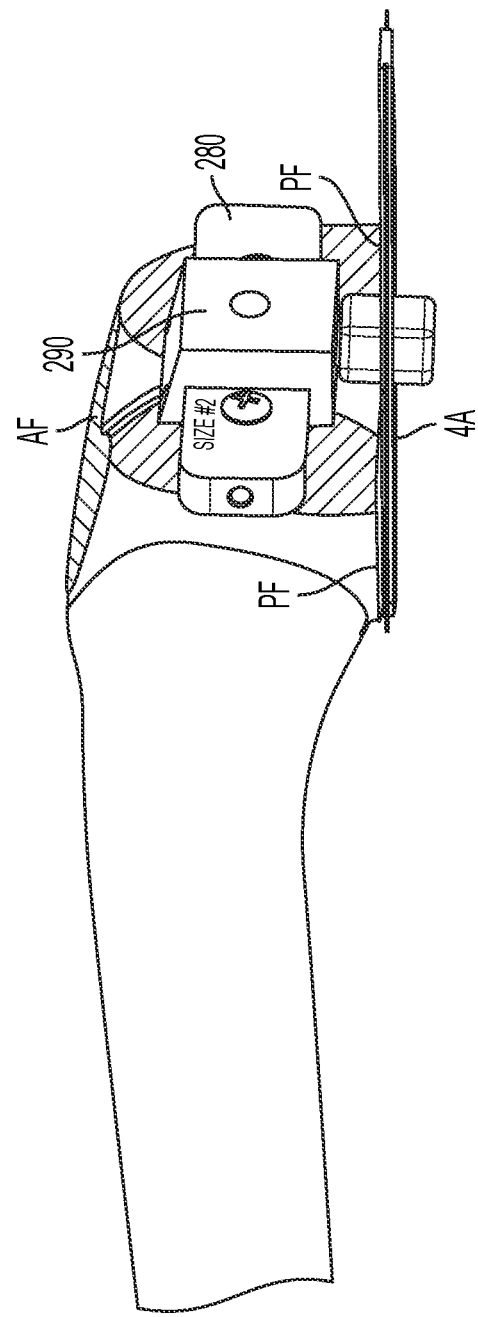
FIG. 42 shows another view of the saw attached to a posterior surface of the first adapter of FIG. 36, while the first adapter of FIG. 36 is positioned over the cut mount block of FIGS. 29-35, securing the saw for making a posterior femur cut.

FIG. 41 shows a saw 4 attached to a posterior surface 293 of the first adapter 290. Like the anterior surface 292, the posterior surface 293 may be shaped, e.g., sloped, to position the saw 4 for making the posterior femur cut PF. The posterior surface 293 may have a hole 294 for receiving a stem on which a lower saw clamp 252 and upper saw clamp 254 can be mounted, with the saw bar 4A between them, in a manner similar to that described above. In an alternative arrangement, the stem is integral with the first adapter 290, extending from the posterior surface 293 in the location of the hole 294. The mounting of the saw bar 4A on the stem allows the saw bar 4A to be advanced forward, to be retracted, and to pivot around the stem, in a manner similar to that described above. Once positioned on the posterior surface 293, the saw 4 can be used to make the posterior femur cut(s) PF, as shown in FIGS. 41 and 42.

Figure 43:
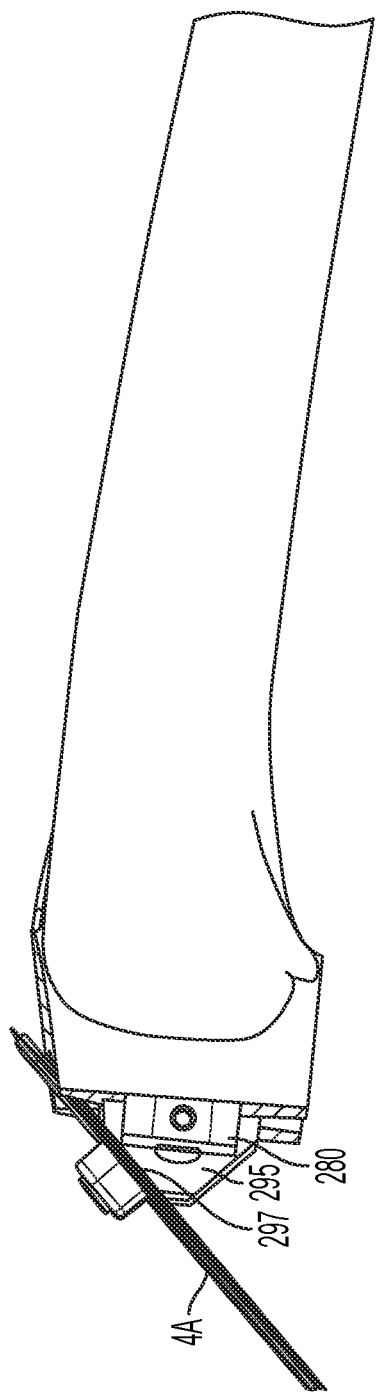
FIG. 43 shows a second adapter positioned over the cut mount block of FIGS. 29-35, securing a saw for making an anterior chamfer cut.
Figure 44:
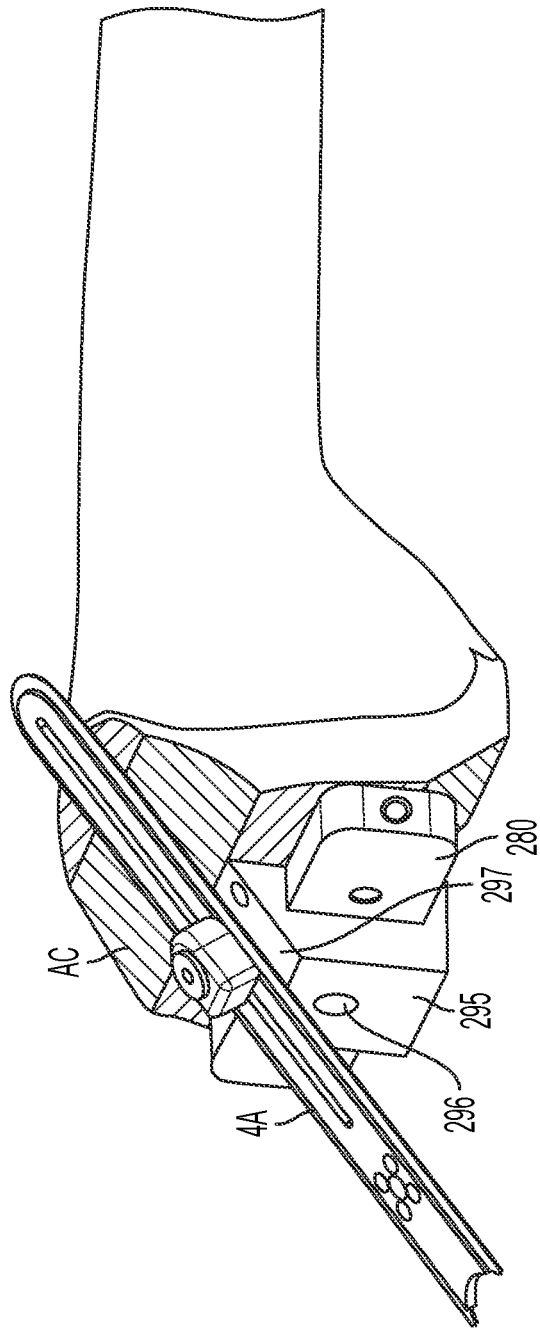
FIG. 44 shows another view of the second adapter positioned over the cut mount block of FIGS. 29-35, securing a saw for making an anterior chamfer cut.
Figure 45:
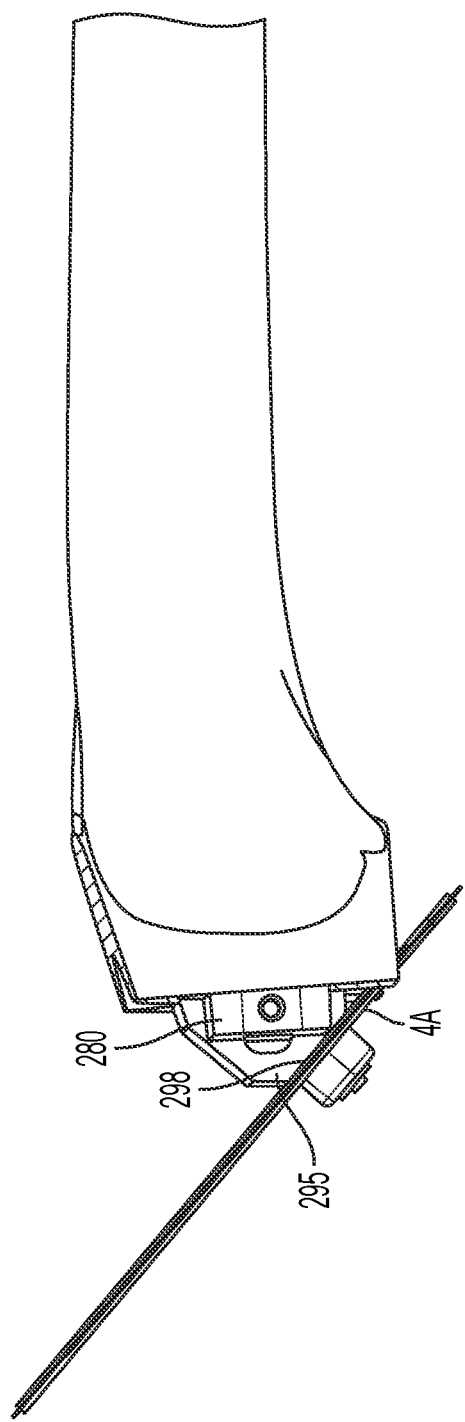
FIG. 45 shows the second adapter positioned over the cut mount block of FIGS. 29-35, securing a saw for making a posterior chamfer cut.

A second adapter 295, as shown in FIGS. 43-45, is sized and shaped to connect to the cut mount block 280 for positioning a saw 4 for making the anterior chamfer cut AC and/or the posterior chamfer cut(s) PC. Like the first adapter 290, the underside of the second adapter 295 may be shaped to fit over the cut mount block 280. The second adapter 295 may be connected to the cut mount block 280 by a fastener by way of the hole 296 in the adapter 295 and the hole 282 in the cut mount block 280.

Once the second adapter 295 is in place, a saw 4 may be attached to it. For example, FIGS. 43 and 44 show a saw 4 attached to an anterior surface 297 of the second adapter 295. The anterior surface 297 may be shaped, e.g., sloped, to position the saw 4 for making the anterior chamfer cut AC. The anterior surface 297 may have a hole for receiving a stem on which a lower saw clamp 252 and upper saw clamp 254 can be mounted, with the saw bar 4A between them, in a manner similar to that described above. In an alternative arrangement, the stem is integral with the second adapter 295, extending from the anterior surface 297 in the location of the hole. The mounting of the saw bar 4A on the stem allows the saw bar 4A to be advanced forward, to be retracted, and to pivot around the stem, in a manner similar to that described above. Once positioned on the anterior surface 297, the saw 4 can be used to make the anterior chamfer cut AC, as shown in FIGS. 43 and 44.

FIG. 45 shows a saw 4 attached to a posterior surface 298 of the second adapter 295. Like the anterior surface 297, the posterior surface 298 may be shaped, e.g., sloped, to position the saw 4 for making the posterior chamfer cut PC. The posterior surface 298 may have a hole for receiving a stem on which a lower saw clamp 252 and upper saw clamp 254 can be mounted, with the saw bar 4A between them, in a manner similar to that described above. In an alternative arrangement, the stem is integral with the second adapter 295, extending from the posterior surface 298 in the location of the hole. The mounting of the saw bar 4A on the stem allows the saw bar 4A to be advanced forward, to be retracted, and to pivot around the stem, in a manner similar to that described above. Once positioned on the posterior surface 298, the saw 4 can be used to make the posterior chamfer cut(s) PC, as shown in FIG. 45.

In alternative embodiments, one or more of the mounting surfaces for the anterior femur cut AF, posterior femur cut(s) PF, anterior chamfer cut AC, and/or posterior chamfer cut(s) PC may be part of the cut mount block 280, such that one or more of the separate adapters 290, 295 may not be needed. For example, FIG. 31 shows a version of the cut mount block 280 with surfaces for making one or more of these cuts.

An example of using the cutting guide system 201 is as follows. First, the user secures the support mount 210 to the bone. The assembly of FIG. 18 may be attached with the support mount 210 or subsequently connected to it. Next, the user may rotate the first adjusting guide 220 and/or the second adjusting guide 230 into a desired position. With a mounting as shown in FIGS. 18-23, adjusting the first adjusting guide 220 can adjust the valgus/varus positioning, and adjusting the second adjusting guide 230 can adjust the flexion/extension positioning. The user can evaluate the alignment visually, with or without additional alignment instruments such as alignment rods attachable to the first adjusting guide 220 and/or the second adjusting guide 230, with reference to anatomical landmarks. Once the first adjusting guide 220 and/or the second adjusting guide 230 is in the desired position, the user can lock its position using the locking mechanism 226 and/or 236, e.g., by tightening the set screw 228 and/or 238. The first adjusting guide 220 may be adjusted before the second adjusting guide 230, or vice versa, and they each can be readjusted after the other is adjusted.

The saw mount 250 can be attached to the assembly of FIGS. 18-24, as described above. A stylus may be used the measure the desired height adjustment for the amount of bone to be removed, as described above. For example, a stylus may be positioned in the place of the saw bar 4A. The saw clamps 252, 254 may be used with the stylus or removed for the stylus mechanism. Alternatively, a stylus mount may be used in place of the saw mount 250. With the stylus, the user would have the ability to determine the desired height for the saw. Then the stylus can be removed and the saw put in place with its height adjusted to the desired height, using the saw mount 250. The saw mount 250 can be locked in position using the locking mechanism 260.

In making the various positionings, the user can be guided using, and/or the information can be coordinated with, optical vision systems, preoperative evaluations, x-rays, CAT scans, MRIs, etc. At any point, the user can release a locking mechanism 226, 236, readjust the respective adjusting guide 220, 230, and then deploy the respective locking mechanism 226, 236 to secure the adjusting guide 220, 230. Similarly, the user can readjust the saw bar height by releasing the locking mechanism 260, adjusting the height, then relocking the saw mount 250 using locking mechanism 260.

The rotational position of the adjusting guides 220, 230 can be transmitted using the transducers 140 as described above. The user can use the position information to make the positionings and/or adjustments and/or additional cuts. As an option, the cutting guide system 201 could have a worm gear or linkage arrangement whereby fine rotating adjustments to the adjusting guides 220, 230 could be made, like a micrometer, to dial in a very specific degree of rotation. As another option, the cutting guide system could be adjusted using one or more motors, such as a stepper motor, for moving the adjusting guide 220 and/or 230.

The cutting guide system 201 isolates the two primary degrees of freedom with the independent adjustability of the first adjusting guide 220 and the second adjusting guide 230. The user can align the cutting guide system 201 in one plane or degree of freedom, lock it into place, and then adjust it in the other plane or degree of freedom. Thus, for example, the user can isolate the varus/valgus adjustment independently from the flexion/extension adjustment.

The cutting guide system 201 may be used to make a distal femur cut DF, as shown in FIGS. 27 and 28. After the distal femur cut DF has been made, the saw mount 250 and saw 4 may be removed. Then, as illustrated in FIG. 29, a guide mount 270 may be connected to the assembly of FIG. 24. The user can adjust the positioning of the cut mount block 280 to its desired position. The user adjusts the height of the cut mount block 280 by the amount the arms 276 extend into the recesses 239, locked in place by the locking mechanism 260. The user adjusts the forward-backward (anterior-posterior) position of the cut mount block 280 by adjusting the position of the adjusting bar 278, as shown in FIG. 31. The user adjusts the angular position of the cut mount block 280 by rotating it about an axis of its connection with the adjusting bar 278, as shown in FIGS. 32 and 33.

Once the cut mount block 280 is in the desired position, the user attaches it to the bone, for example by one or more fasteners 285, as shown in FIG. 34. Then, the guide mount 270 can be removed from the cut mount block 280, for example by releasing the fastener (not shown) that had been engaged with the threaded hole 282 in the cut mount block 280. The assembly of FIG. 24 can also be removed, leaving only the attached cut mount block 280 (and any fastener(s) for it), as shown in FIG. 35. The user may use the cut mount block 280, optionally with one or more adapters 290, 295, to make the anterior femur cut AF, the posterior femur cut(s) PF, the anterior chamfer cut AC, and/or the posterior chamfer cut(s) PC.

Some or all of the parts of the cutting guide systems described herein may be reusable or disposable. For example, the support mount 110, 210 and adjusting guides 120, 130, 220, 230 may be made out of surgical stainless steel or anodized aluminum and may be sterilized and reused. The transducers 140 may comprise plastic and may be inexpensive and disposable. Similarly, the saw bar clamps and saw bar may be disposable.

In use, certain embodiments of the cutting guide systems described herein allow for simple securement of the cutting guide system to the bone, simple positioning of the saw with respect to the bone, and simple readjustment of that positioning if needed. Certain embodiments of the cutting guide systems described herein facilitate good visualization by the user. Certain embodiments of the cutting guide systems described herein can be designed to be usable with a range of different implant sizes.

With any of the cutting guide systems described herein, after a cut has been made, the user can evaluate the cut and make one or more additional cuts, if desired. For example, the user can measure the piece of bone that has been cut off and add in the kerf of the saw cut to determine the amount that has been cut. Then the user can evaluate whether to make one or more additional cuts.

After using one or more of the cutting guide systems as described herein to make the desired cuts, the user can put on a trial prosthesis for testing. For example, the user can put on a trial femur prosthesis and a trial tibial prosthesis and put the leg through range of motion. The user in this example may even put the patella back so that the joint is totally enclosed by the skin for a more complete evaluation. The user may evaluate, e.g., overall leg alignment, the valgus-varus positioning, and the amount of flexion-extension, to avoid hyperextension which is poor for instability as well as to avoid too little flexion so that there is a good range of motion. If desired, the user can go back and make additional cuts based on the prior positionings of the cutting guide system(s).

While certain examples described herein have been discussed in relation to the cutting of bone, cutting guide systems as disclosed herein may also be used in other fields, such as construction. For example, cutting guide systems may be adapted and used for stabilizing a cutting instrument for cutting wood, drywall, plastic, and other materials. The support mount may be attachable in a fixed relation with respect to the object to be cut by the cutting instrument. For example, the cutting guide systems may be used for guiding cuts for air registers, sockets, windows, or other areas where cuts are useful. The support mount may be attached to the object to be cut or to an adjacent object that is in a fixed relation with respect to the object to be cut (such as an adjacent beam, panel, support, or other object). In one example, the cutting guide systems may be used for guiding a cutting instrument (e.g., a chain saw, other saw, knife, etc.) to make a plunge cut into material (e.g., drywall, wood, etc.) and/or for guiding the cutting instrument along a desired cutting path (e.g., opening for an air duct, socket, light switch, window, etc.).

As discussed above, systems as described herein may be used manually or used with robotic platforms, wherein the cutting instrument is maneuvered robotically. The cutting guide system may include one or more motive devices, e.g., motors, linear or rotary actuators, stepper motors, etc., to move the cutting guide system and/or the cutting instrument (e.g., pivoting of joints, adjusting height of cutting instrument, plunging/moving cutting instrument, etc.). The movements may be programmed so that a cut along a predetermined path can be made in the object to be cut (e.g., bone cuts, cuts for openings for air ducts, sockets, light switches, windows, etc.).

The cutting guide systems as described herein can achieve one or more advantages over prior systems. One or more of the following advantages may be realized: lower cost, easier use, more precise alignment, more precise cuts, lower cutting time, lower procedure time, lower recovery time, and/or better outcomes.

Persons of ordinary skill in the art will appreciate that the embodiments encompassed by the disclosure are not limited to the particular example embodiments described above. While illustrative embodiments have been shown and described, a wide range of modification, change, and substitution is contemplated in the foregoing disclosure. It is understood that such variations may be made to the foregoing without departing from the scope of the disclosure.

What is claimed is:

1. A cutting guide system for stabilizing a cutting instrument in the form of a chain saw comprising a saw bar and a cutting chain around the saw bar, the cutting guide system comprising:
   a support mount attachable in a fixed relation with respect to an object to be cut by the cutting instrument;
   a joint; and
   a cutting instrument support;
   wherein the joint is adapted to permit the cutting instrument support to be adjusted with respect to the support mount;
   wherein the cutting instrument support comprises a stem;
   wherein the cutting guide system is configured to allow the cutting instrument to be adjusted to a plurality of different positions along a direction of a longitudinal axis of the stem;
   wherein the cutting guide system is configured to allow the cutting instrument to be locked at a selected position along the direction of the longitudinal axis of the stem, such that when the cutting instrument is locked at the selected position along the direction of the longitudinal axis of the stem, the cutting instrument is prevented from moving in the direction of the longitudinal axis of the stem; and
   wherein the cutting guide system is configured such that, when the cutting instrument is locked at the selected position along the direction of the longitudinal axis of the stem, the saw bar of the cutting instrument is locked in a cutting plane, with the saw bar rotatable within said cutting plane about a pivot axis such that a longitudinal axis of the saw bar is movable within said cutting plane to a plurality of angular positions, wherein at each of the plurality of angular positions of the longitudinal axis of the saw bar within said cutting plane the saw bar is movable back and forth linearly within said cutting plane in a direction of the longitudinal axis of the saw bar.

2. The cutting guide system as recited in claim 1, wherein the joint is adapted to permit the cutting instrument support to be rotated about at least two axes.

3. The cutting guide system as recited in claim 1, wherein the joint comprises a ball and socket.

4. The cutting guide system as recited in claim 3, wherein the ball and socket are lockable with respect to each other.

5. The cutting guide system as recited in claim 3, wherein the stem is connected to the ball or the socket.

6. The cutting guide system as recited in claim 1, wherein the joint comprises a first hinge comprising a first rod and a first opening, wherein the first rod is positioned in the first opening for relative rotational movement between the first rod and the first opening, allowing a first adjusting guide to pivot about a first axis with respect to the support mount.

7. The cutting guide system as recited in claim 6, wherein the first adjusting guide and the support mount are lockable with respect to each other.

8. The cutting guide system as recited in claim 6, further comprising a first transducer adapted to detect an amount of rotation of the first adjusting guide about the first axis.

9. The cutting guide system as recited in claim 6, wherein the joint further comprises a second hinge comprising a second rod and a second opening, wherein the second rod is positioned in the second opening for relative rotational movement between the second rod and the second opening, allowing a second adjusting guide to pivot about a second axis with respect to the first adjusting guide.

10. The cutting guide system as recited in claim 9, wherein the second adjusting guide and the first adjusting guide are lockable with respect to each other.

11. The cutting guide system as recited in claim 9, further comprising a second transducer adapted to detect an amount of rotation of the second adjusting guide about the second axis.

12. The cutting guide system as recited in claim 1, wherein the cutting instrument support further comprises a first saw clamp and a second saw clamp.

13. The cutting guide system as recited in claim 1, wherein the cutting instrument support comprises a saw mount, and wherein a position of the saw mount with respect to an adjusting guide is adjustable.

14. The cutting guide system as recited in claim 13, wherein the position of the saw mount with respect to the adjusting guide is lockable.

15. The cutting guide system as recited in claim 1, further comprising a guide mount for positioning a cut mount block, wherein a position of the guide mount with respect to an adjusting guide is adjustable in a longitudinal direction.

16. The cutting guide system as recited in claim 15, wherein the cut mount block is adapted to be fastened to the object cut by the cutting instrument.

17. The cutting guide system as recited in claim 16, further comprising an adapter for mounting the cutting instrument on the cut mount block.

18. The cutting guide system as recited in claim 1, wherein the cutting plane is perpendicular to the longitudinal axis of the stem.

19. The cutting guide system as recited in claim 1, wherein the stem is adapted to extend through a slot in the saw bar of the cutting instrument, such that the cutting instrument is pivotable with respect to the stem, and such that the cutting instrument is movable back and forth in a longitudinal direction with respect to the stem.

20. A cutting guide system for stabilizing a cutting instrument in the form of a chain saw comprising a saw bar and a cutting chain around the saw bar, the cutting guide system comprising:
   a support mount attachable in a fixed relation with respect to an object to be cut by the cutting instrument;
   a joint; and
   a cutting instrument support;
   wherein the joint is adapted to permit the cutting instrument support to be adjusted with respect to the support mount;
   wherein the cutting instrument support comprises a stem; and
   wherein the stem is adapted to extend through a slot in the saw bar of the cutting instrument, such that the cutting instrument is pivotable with respect to the stem, and such that the cutting instrument is movable back and forth in a longitudinal direction with respect to the stem.

21. A cutting guide system for stabilizing a cutting instrument in the form of a chain saw comprising a saw bar and a cutting chain around the saw bar, the cutting guide system comprising:
a support mount attachable in a fixed relation with respect to an object to be cut by the cutting instrument;
a joint; and
a cutting instrument support;
wherein the joint is adapted to permit the cutting instrument support to be adjusted with respect to the support mount;
wherein the cutting guide system is configured to allow the cutting instrument to be adjusted to a plurality of different positions along a direction of a longitudinal axis of the cutting instrument support;
wherein the cutting guide system is configured to allow the cutting instrument to be locked at a selected position along the direction of the longitudinal axis of the cutting instrument support, such that when the cutting instrument is locked at the selected position along the direction of the longitudinal axis of the cutting instrument support, the cutting instrument is prevented from moving in the direction of the longitudinal axis of the cutting instrument support; and
wherein the cutting guide system is configured such that, when the cutting instrument is locked at the selected position along the direction of the longitudinal axis of the cutting instrument support, the saw bar of the cutting instrument is locked in a cutting plane, with the saw bar rotatable within said cutting plane about a pivot axis such that a longitudinal axis of the saw bar is movable within said cutting plane to a plurality of angular positions, wherein at each of the plurality of angular positions of the longitudinal axis of the saw bar within said cutting plane the saw bar is movable back and forth linearly within said cutting plane in a direction of the longitudinal axis of the saw bar.

22. The cutting guide system as recited in claim 21, wherein the cutting instrument support further comprises a first saw clamp and a second saw clamp.

23. The cutting guide system as recited in claim 21, wherein the cutting instrument support comprises a stem, and wherein the position of the cutting instrument along a longitudinal axis of the stem is adjustable.

24. The cutting guide system as recited in claim 23, wherein the position of the cutting instrument along the longitudinal axis of the stem is lockable.

25. The cutting guide system as recited in claim 21, wherein the cutting instrument support comprises a saw mount, and wherein a position of the saw mount with respect to an adjusting guide is adjustable.

26. The cutting guide system as recited in claim 25, wherein the position of the saw mount with respect to the adjusting guide is lockable.

27. The cutting guide system as recited in claim 21, wherein the cutting instrument support and the support mount are lockable with respect to each other.

28. The cutting guide system as recited in claim 21, further comprising an adapter for positioning the cutting instrument for a plurality of different planar cuts.

29. The cutting guide system as recited in claim 28, wherein the adapter comprises a plurality of securing positions for the cutting instrument, each of said plurality of securing positions configured to align the cutting instrument for a different planar cut.

30. The cutting guide system as recited in claim 29, wherein the adapter is configured to be secured to the object cut by the cutting instrument.

31. The cutting guide system as recited in claim 30, wherein the cutting guide system is configured to position the adapter on the object cut by the cutting instrument.

32. The cutting guide system as recited in claim 31, wherein the cutting guide system comprises a cut mount block that is adapted to be fastened to the object cut by the cutting instrument in order to position the adapter on the object cut by the cutting instrument.

33. The cutting guide system as recited in claim 21, wherein the joint comprises a first hinge and a first transducer adapted to detect rotational movement at the first hinge, wherein feedback from the first transducer is adapted to be used to adjust the positioning of the cutting guide system.

34. The cutting guide system as recited in claim 33, wherein the joint comprises a second hinge and a second transducer adapted to detect rotational movement at the second hinge, wherein feedback from the second transducer is adapted to be used to adjust the positioning of the cutting guide system.

35. The cutting guide system as recited in claim 21, wherein the cutting plane is perpendicular to the longitudinal axis of the cutting instrument support.

* * * * *